United States Patent
McDaniel (12)

(10) Patent No.: US 6,663,659 B2
(45) Date of Patent: Dec. 16, 2003

(54) METHOD AND APPARATUS FOR THE PHOTOMODULATION OF LIVING CELLS

(76) Inventor: David H. McDaniel, 3033 Little Haven Rd., Virginia Beach, VA (US) 23452

(*) Notice: Subject to any disclaimer, the term of this patent is extended or adjusted under 35 U.S.C. 154(b) by 0 days.

(21) Appl. No.: 09/894,899

(22) Filed: Jun. 29, 2001

(65) Prior Publication Data

US 2003/0004499 A1 Jan. 2, 2003

Related U.S. Application Data

(63) Continuation-in-part of application No. 09/759,094, filed on Jan. 12, 2001.
(60) Provisional application No. 60/176,175, filed on Jan. 13, 2000.

(51) Int. Cl.$^7$ .............................................. A61N 5/006
(52) U.S. Cl. ............................. 607/88; 607/90; 607/91; 606/3; 606/9; 128/898
(58) Field of Search ................... 606/3, 8–10, 214, 606/215; 607/88–91; 128/898

(56) References Cited

U.S. PATENT DOCUMENTS

| | | | |
|---|---|---|---|
| 4,458,678 A | | 7/1984 | Yannas et al. |
| 4,646,743 A | | 3/1987 | Parris |
| 4,767,402 A | | 8/1988 | Kost et al. |
| 4,836,203 A | | 6/1989 | Muller et al. |
| 4,888,354 A | | 12/1989 | Chang et al. |
| 4,930,504 A | * | 6/1990 | Diamantopoulos et al. . 128/395 |
| 4,969,912 A | | 11/1990 | Kelman et al. |
| 5,021,452 A | | 6/1991 | Labbe et al. |
| 5,037,432 A | | 8/1991 | Molinari |
| 5,198,465 A | | 3/1993 | Dioguardi |
| 5,226,907 A | | 7/1993 | Tankovich |
| 5,231,975 A | | 8/1993 | Bommannan et al. |
| 5,266,480 A | | 11/1993 | Naughton et al. |
| 5,332,802 A | | 7/1994 | Kelman et al. |
| 5,358,503 A | * | 10/1994 | Bertwell et al. ............... 606/27 |
| 5,366,498 A | | 11/1994 | Brannan et al. |
| 5,397,352 A | | 3/1995 | Burres |
| 5,423,803 A | | 6/1995 | Tankovich et al. |
| 5,425,728 A | | 6/1995 | Tankovich |
| 5,445,146 A | | 8/1995 | Bellinger |
| 5,445,634 A | | 8/1995 | Keller |
| 5,460,939 A | | 10/1995 | Hansbrough et al. |
| 5,474,528 A | * | 12/1995 | Meserol ....................... 604/20 |
| 5,591,444 A | | 1/1997 | Boss, Jr. |
| 5,620,478 A | | 4/1997 | Eckhouse |
| 5,643,334 A | | 7/1997 | Eckhouse |
| 5,647,866 A | | 7/1997 | Zaias et al. |
| 6,063,108 A | * | 5/2000 | Salansky et al. .............. 607/89 |
| 6,096,066 A | * | 8/2000 | Chen et al. ................... 607/88 |
| 6,251,127 B1 | * | 6/2001 | Biel ............................. 607/88 |
| 2001/0023363 A1 | | 9/2001 | Harth et al. .................. 607/90 |

FOREIGN PATENT DOCUMENTS

SU        1724269 A1 *  4/1992   ............ A61N/5/06

OTHER PUBLICATIONS

A. K. Gupta et al. "The use of Low Energy Photon Therapy in the Treatment of Leg Ulcers—A Preliminary Study" Journal of Dermatological Treatment, (1997), vol. 8, No. 2, 103–108.*
D. H. McDaniel et al. "Treatment of Stretch Marks with 585 nm Flashlamp–pumped Pulsed Dye Laser" Dermatological Surgery (1996), vol. 22, No. 4, 332–337.*

* cited by examiner

*Primary Examiner*—Linda C. M. Dvorak
*Assistant Examiner*—A. Farah
(74) *Attorney, Agent, or Firm*—Morrison & Foerster LLP

(57) ABSTRACT

The invention is a system and method for the photomodulation of living tissue. When photomodulated, living tissue will exhibit bioactivation or bioinhibition according to the present invention and, when using the disclosed sources of narrowband multichromatic radiation can cause significant dermatologic advantages such as hair removal, hair growth stimulation, wrinkle reduction, acne reduction and scar removal, vitiligo, etc. This invention may be applied to non-dermatological medical treatments including tumor growth inhibition, cell regeneration, the stimulation of tissue in organs, etc.

14 Claims, 36 Drawing Sheets

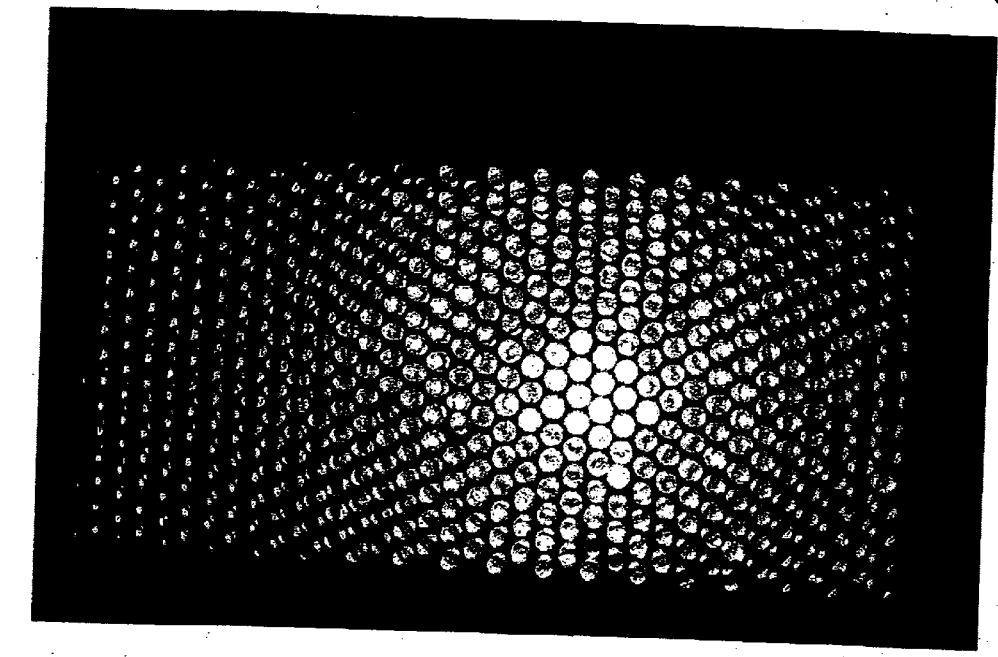
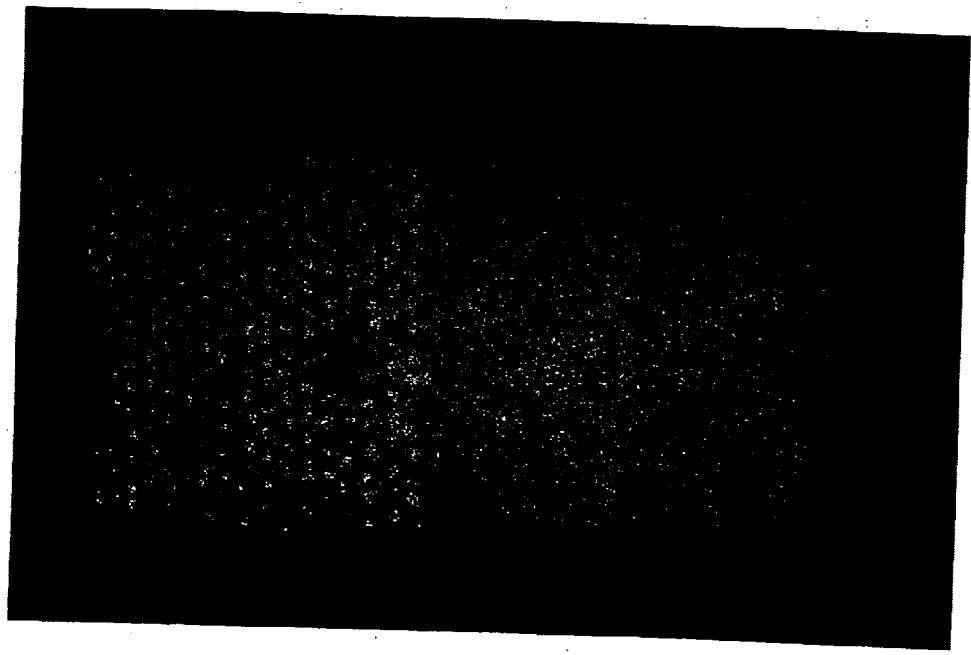
FIG. 3

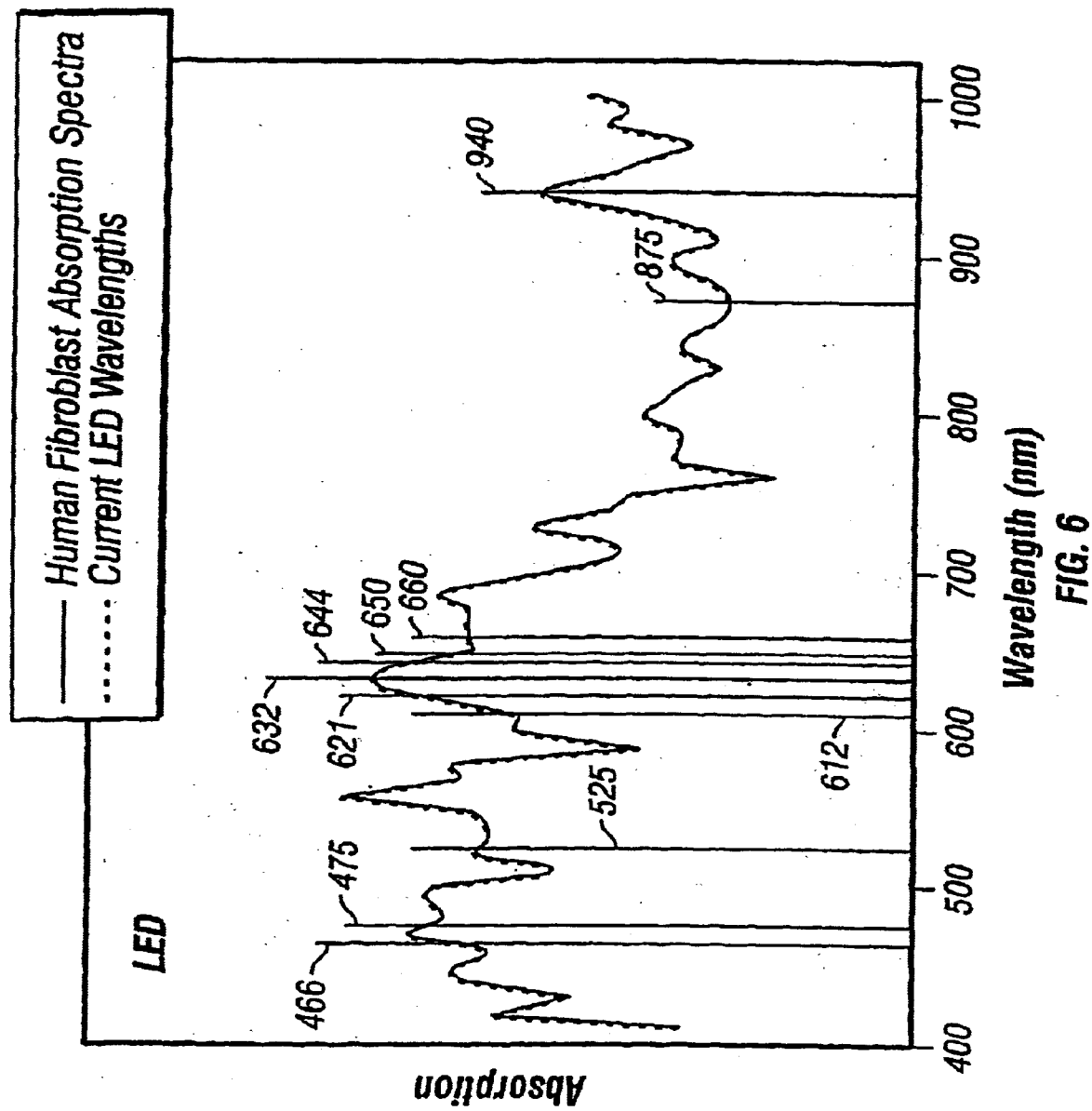

FRONT VIEW LIGHT PANEL

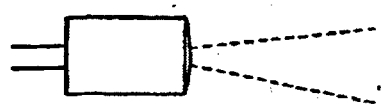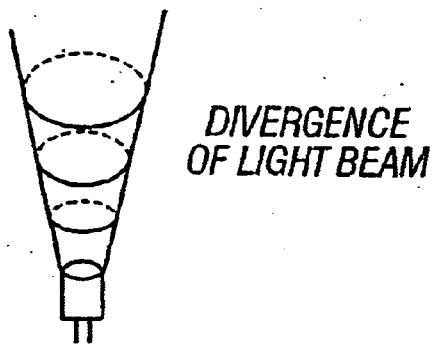
FIG. 17A   FIG. 17B
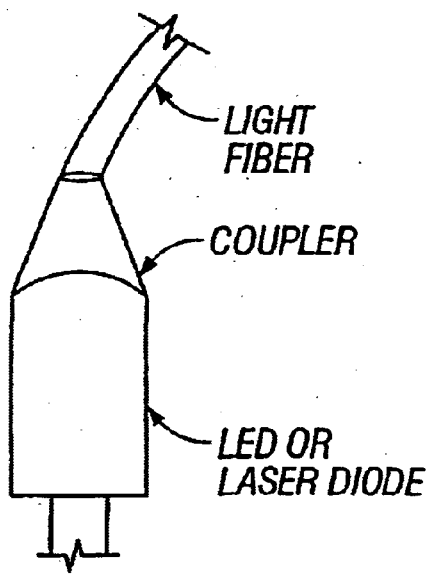
FIG. 17C
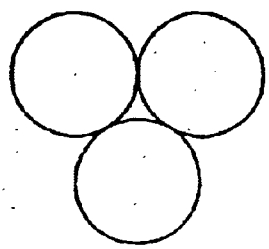 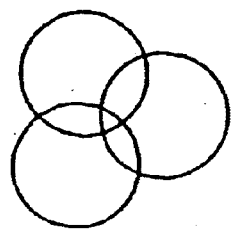 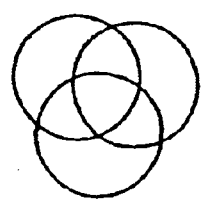
FIG. 18A   FIG. 18B   FIG. 18C

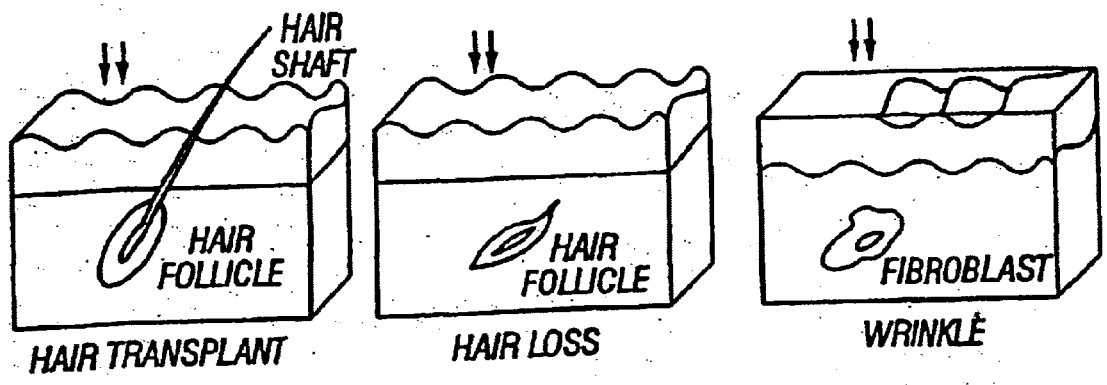
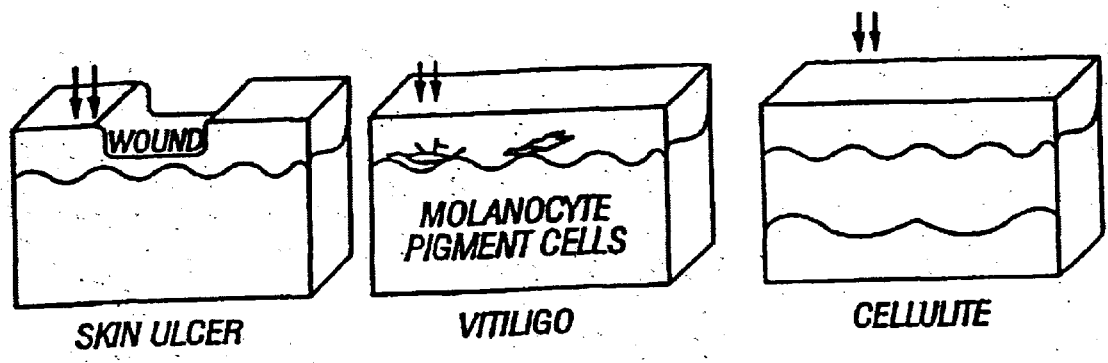
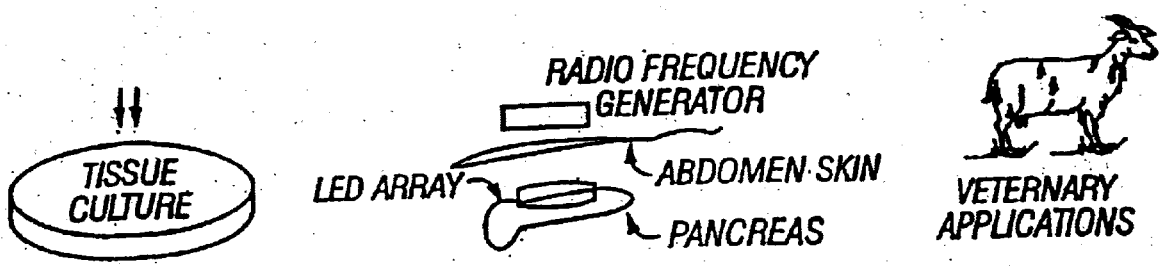
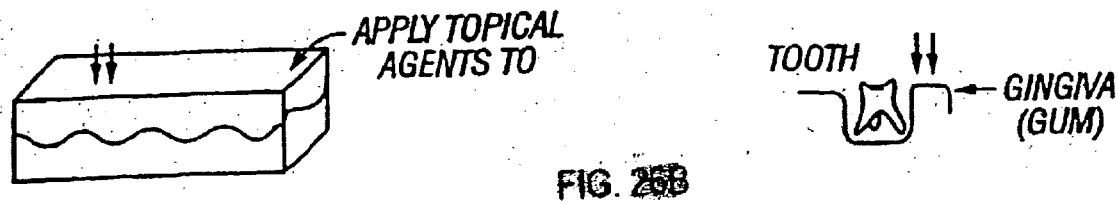
FIG. 26B

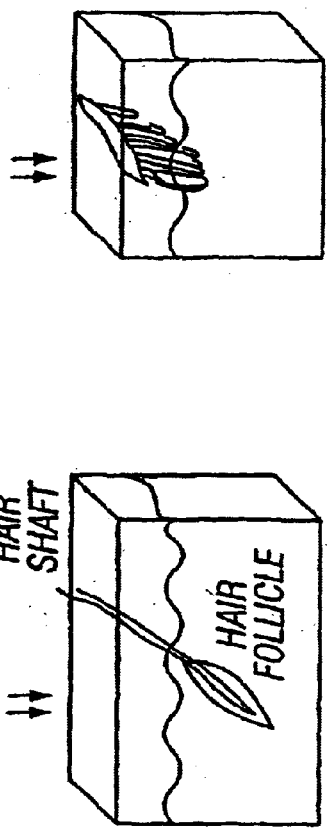
FIG. 27A PSORIASIS
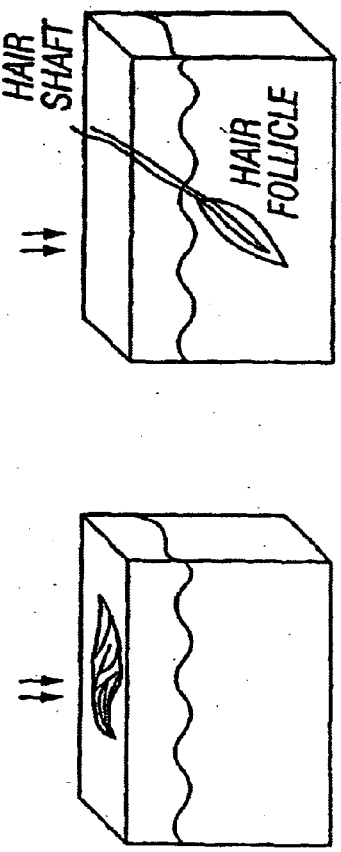
FIG. 27B HAIR GROWTH
FIG. 27C HYPERTROPHIC SCAR
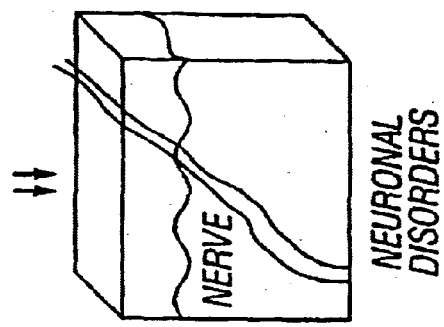
FIG. 27D ACNE
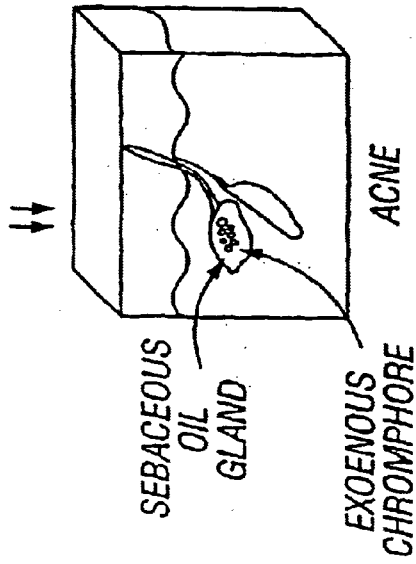
FIG. 27E NEURONAL DISORDERS
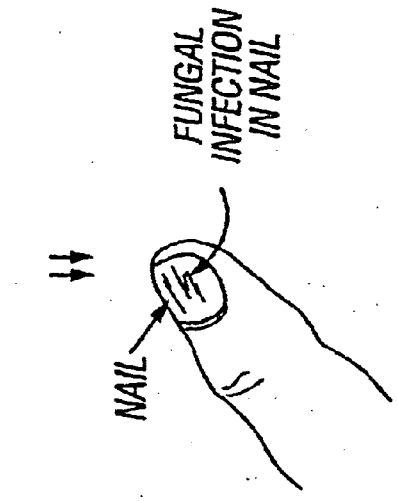
FIG. 27F FUNGAL INFECTION IN NAIL

METHOD AND APPARATUS FOR THE PHOTOMODULATION OF LIVING CELLS

RELATED APPLICATIONS

This application is a continuation-in-part and related to and claims the priority of copending U.S. application Ser. No. 09/759,094 filed Jan. 12, 2001 now abandoned which claims the priority of provisional application serial No. 60/176,175, filed Jan. 13, 2000, both of which are hereby incorporated by reference in their entirety.

FIELD OF THE INVENTION

The present invention relates to a method and apparatus for using a narrowband, multichromatic electromagnetic radiation emitter to photomodulating living tissue and, in particular, human cell-containing tissue. By exposing living tissue to electromagnetic radiation in carefully chosen wavelength-bands of the spectrum either continuously for a period of time or in pulses of a predetermined frequency, cells within living tissue can be stimulated to begin genetically determined routines or regenerative functions or inhibited from these same functions. The novel photomodulation apparatus and method can be used to control, stimulate, or inhibit cell growth to treat conditions caused by undesirable or suboptimal cell growth or cell function.

BACKGROUND OF THE INVENTION

It is traditionally accepted that the coherent nature of laser light (which is one of the properties that sets laser light apart form all other light) is necessary for the current applications of light sources used in medical treatment. This is particularly true for biostimulatory or bioinhibitory effects in living tissue since essentially all of the research is with lasers. Lasers, however, are very expensive devices, require large amounts of power, and can be extremely dangerous unless used under the strict supervision of qualified medical personnel. Further, lasers have long been believed to be essentially the only suitable source of electromagnetic radiation for generating effective biostimulatory or bioinhibitory effects because it was assumed that the light source must be monochromatic, that is of a single pure color or wavelength, i.e., is monchromatic—operating in a narrow spectrum of wavelengths. While other narrowband, multichromatic emissions sources have been known, such as laser diodes and, more generally, light emitting diodes ("LEDs"— devices capable of emitting electromagnetic radiation in a narrow spectrum of wavelengths), LEDs have never been widely accepted as suitable for use in medical treatment due to their limited power output and the low intensity of electromagnetic radiation they are capable of delivering to the living tissue receiving treatment. Moreover, despite the recent emergence of very high brightness LEDs, interest in the use of LEDs as a replacement for lasers in applications such as dermatological treatment, for example, has not become known within the art.

The lack of interest in using LEDs to replace lasers for medical treatment may be because most current lasers have very short pulse duration and also very high peak power. These are both properties that cannot be achieved by current LEDs and might never be. However, new lasers for treating unwanted hair and veins have more recently been developed that are 'long pulsed' and also use much lower peak power. As well, most biostimulatory experiments have used higher energies than those possible with LEDs. The thought of stringing hundreds or thousands of LEDs together has never been considered as it may have been considered to be an optical challenge for some applications.

Most laser technology applied for medical use is adapted from military laser technology and only more recently has the development of laser systems specifically created for medical use become commonplace, so LED systems that could be adapted for living tissue were not pre-existing like the lasers. Almost all laser research is directed at delivering the laser beam through mirror or fiber optics to living tissue. The maximum beam diameter is determined usually by the diameter of the lasing medium laser head. While it is commonplace to 'narrow' the beam diameter from that exiting the laser head, making the beam wider is rarely done as preserving the desired-required treatment parameters laser qualities becomes a significant optical issue and there is insufficient power to cover large areas with these parameters. Simply put, no one has been thinking of trying to cover say a square foot of surface with a laser beam, and currently a square inch is considered quite large for most medical applications. The concept of directly delivering the light from the LED directly to living tissue from the LED source itself is, therefore, contrary to laser design logic and the most likely reasoning why LEDs have never been thoroughly explored as an option for producing electromagnetic emissions for medical use.

Perhaps due to the belief that lasers are the only viable source of light applicable for use in medical treatment, or perhaps due to the belief that effective medical treatment required high energy light sources or high intensity pulsed sources (therefore leading to the widely accepted belief that lasers and similar high-intensity, monochromatic light sources are the only commercially useful sources of light), current clinical treatment regimens have been focused on applying enough energy to living tissue to heat the target molecules (i.e., water, blood, collagen, etc) therein above the minimum threshold needed to produce thermal injury. Thermal injury then occurs prior to wound healing—the phase in which skin begins to repair and regenerate by the formation, among many other things, new collagen fibers. For example, many laser-based treatments cause thermal injury that is believed to have a stimulatory effect by releasing chemicals which signal that the body has been wounded or injured and thus initiates a well defined sequence of events collectively termed wound healing. The end result of the wound healing mechanism may be the production of new collagen, but this occurs as a result of lethal or significant non-lethal damage to many types of cells. In contrast, through direct photoactivation (rather than a treatment regimen in which photothermal injury occurs) the direct bioactivation of a specific cell or subcellular component is triggered without appreciable levels of thermal injury or cell damage. Also, photoactivated biostimulation tends not to produce uncontrolled wound healing or abnormal wound healing (also termed scarring) as can all thermal events. Finally, there is another even higher level of thermal injury that causes protein denaturation and cell destruction and cell death. Such treatments can cause significant patient pain or discomfort and require lengthy recovery times.

Lastly, even the lowest-power lasers available for medical treatment require the supervision of qualified medical personnel. Even low-power lasers can cause at least eye damage or some degree of tissue injuries; and most lasers used for medical treatment have a risk of serious electrical shock or death. None are classified as 'Insignificant Risk Devices', a classification for devices (such as hair dryers, electric toothbrushes, etc.) which are deemed suitable for use without medical supervision due to the minimal risks of harm or injury they pose.

It would, therefore, be desirable to have a device, and a method of using such a device, that can provide the benefits of laser treatment at significantly reduced cost and power requirement while retaining the ability to deliver sufficient intensities of narrowband, multichromatic electromagnetic radiation to living tissue to induce biostimulatory or bioinhibitory effects as part of a regimen of medical treatment. Such a treatment regimen could provide significant dermatological benefits by the photoactivation of cells to induce skin rejuvenation (i.e., the generation of new collagen) without thermally injuring the skin.

It would also be advantageous to have a source of narrowband multichromatic electromagnetic radiation and a method of using such a device to make it capable of inducing beneficial biostimulatory or bioinhibitive effect without the need to heat the tissue above the level of thermal injury, thereby essentially eliminating patient pain, discomfort, and recovery time.

It would also be a significant advancement to the art to have a device and method of using such a device that can induce beneficial bioactivating or bioinhibiting effects in living tissue that does not require medical supervision or, in at least one embodiment, pose a potential risk of eye injury, electric shock, or death.

SUMMARY OF THE INVENTION

In accordance with the present invention, the photomodulation of living tissue is achieved through the use of narrowband, mulichromatic sources of electromagnetic radiation. A preferred embodiment uses at least one light emitting diode. A plurality of these diodes may be arranged in an array to emit a wavelength from about 300 nm to about 1600 nm. Although the wavelength is chosen based on the nature of the treatment desired, preferred wavelengths include 590 nm, 644 nm, or 810 nm with a bandwith of at least +/−5 nm.

An alternate process employs a laser diode alone or in combination with an LED or plurality of LEDs. This method may employ a continuous wave or a pulse of a period of from approximately 1.0 ms to about $1 \times 10^6$ ms, a light intensity of less than 1 watt/cm2, and the temperature of the living tissue not to exceed 60° C. If further stimulation is necessary pulsing may continue from 10 seconds to 1 hour. The preferred wavelengths this process employs are 400 nm, 445 nm, 635 nm, 660 nm, 670 nm, 780 nm, 785 nm, 810 nm, 830 nm, 840 nm, 860 nm, 904 nm, 915 nm, 980 nm, 1015 nm, or 1060 nm.

Another embodiment of the method of present invention the emitter of electromagnetic radiation produces a light intensity of from about 1 nanowatt to less than about 4 watts/cm2.

Dermatological treatment may be carried out using a light emitting diode, laser diode, dye laser, flashlamp, fluorescent, filamentous, incandescent, or other emitter configured by electrical means or mechanical filtering to emit only a narrowband of wavelength centered about a dominant wavelength; and in particular 300 nm, 415 nm, 585 nm, 590 nm, 595 nm, 600 nm, 644 nm, 810 nm, 940 nm, and 1400 nm. The energy level for this process is from about 1 nanowatt/ $cm^2$ to about 4 watts/cm2 or about 200 milliwatts/cm2 to about 1000 milliwatts/cm2, wherein the exposure comprises pulsing the emitter from about 1 ms to about $1 \times 10^6$ ms. The pulse itself may last from about 150 ms to about 850 ms.

Further dermatological treatment suggests applying a topical agent to an area of human skin to enhance the penetration of a wavelength of light chosen for such treatment. This includes exposing the human skin to a source of narrowband, multichromatic electromagnetic radiation with a wavelength from approximately 300 nm to approximately 1600 nm for about 1 millisecond to about 30 minutes. If necessary, re-exposure every 1 to 60 days would last from 1 millisecond to about 30 minutes up to 1000 times with an interpulse interval from about 1 millisecond to about 1000 milliseconds keeping the skin temperature below the threshold at which thermal injury occurs.

Topical agents suitable for use in conjunction with the emitters of the present invention include exogenous chromophores, cosmeceuticals and, in addition, pretreatment including penetration or removal of at least some portion of the stratum corneum layer of the patient's skin may improve treatment efficacy as will the use of an agent topically administered to adjust the absorption spectrum or refractive index of the patient's skin. Further, topical agents applied to enhance or synergistically enhance the treatment process of the present invention may function without exhibiting the characteristics of an exogenous chromophore.

An additional embodiment for dermatological treatment is where abrasion of a segment of the skin to be treated enhances the transmission through the stratum corneum of the narrowband, multichromatic electromagnetic radiation emitter. A wavelength from about 300 nm to about 1600 nm for about 1 millisecond to about 30 minutes is used. If necessary, re-exposure may last from about 1 millisecond to about 30 minutes up to about 1000 times with an impulse interval from about 1 millisecond to about 1000 milliseconds every 1 to 60 days.

BRIEF DESCRIPTION OF THE DRAWINGS

FIG. 3 is an illustration of an embodiment of an LED array of the present invention.

FIG. 6 is a graphical illustration of the absorption spectrum of human fibroblast overlayed with the wavelengths used by narrowband, multichromatic LED emitters of the present invention.

FIG. 7 is a graphical illustration of the absorption spectra of human fibroblast overlayed with the wavelengths used by narrowband, multichromatic LED emitters of the present invention and also the absoprtion spectrum of chlorophyll a.

FIG. 13A shows a block flow diagram of the control system of the present invention.

FIGS. 17A–C illustrate examples of individual LEDs in accordance with the present invention and the angle of divergence of an emitted beam.

FIGS. 18A–C illustrates three different examples of patterns of light energy density on the field of illumination. The irradiation illustrated in FIG. 18B is relatively uniform and homogeneous. The irradiation illustrated in FIG. 18C is relatively uneven and non homogeneous.

FIG. 22A illustrates an example of a pattern enabling illumination of a broad and generally flat surface area.

FIGS. 22B and 22C illustrate examples of focused illumination patterns.

FIG. 26B illustrates alternate configurations for achieving biostimulatory effects, wherein a variety of optical events occur as light intersects the skin surface (or any surface).

FIGS. 27A–F illustrated bioinhibitory effects resulting from treatment according to the present invention.

FIG. 27A illustrates an example of use on skin diseases such as psoriasis (a proliferative skin disorder that is known to respond to ultraviolet light therapy).

FIG. 27B illustrates another application to delay or inhibit hair growth.

FIG. 27C illustrates the treatment of scars or stretch marks is also possible.

FIG. 27D shows the use of LED light in conjunction with an exogenous chromophore to diminish oil gland activity or to reduce acne.

FIG. 27E illustrates an example of illumination by the LED of nerve fibers where nerve injuries need to be stimulated, regenerated, or healed.

FIG. 27F illustrates nail disorders with fungal infection.

FIGS. 31A–F illustrate examples of electron microscopic photographic images of fibroblasts in culture after irradiation with one embodiment of the present invention using very low levels of light energy produced by a 595 nm yellow LED emitting in the millicandela or microwaft range. FIG. 31A and the left half of FIG. 19b show living but altered cells. The right side of FIG. 31B illustrates an example of dead or dying cells (the latter were exposed to much higher energy levels than the former). These cells are seen again in FIG. 31C with cytoskeletal changes reflecting alteration of the cells but not destruction, FIG. 31D illustrates an example of severely damaged cells. Images "e" and "f" are higher magnification of the altered but living cells in "a" and "c".

DETAILED DESCRIPTION OF THE INVENTION

The present invention relates to a method and apparatus for the treatment of living cells or tissue using electromagnetic radiation produced by at least one optoelectronic device. The types of optoelectronic devices used in the present invention may include, for example, light emitting diodes (LED), laser diodes, flashlamps, dye lasers, fluorescent light sources, or filamentous light sources (with or without wavelength filtration). Suitable light sources for use in accordance with the present invention include those disclosed in U.S. Pat. Nos. 6,224,071 and 6,187,029, which are hereby incorporated by reference in their entirety.

More specifically, the present invention is to a treatment and apparatus for photomodulating tissue cells. Photomodulation refers to the process of using light to either activate (photoactivation) or inhibit (photoinhibition) a cell's natural function. For example, wrinkles are removed when new collagen is formed within skin tissue. The process of photoactivation stimulates collagen growth by using an LED at a pulse rate, pulse duration, and intensity to activate human or animal fibroblast cells that produce collagen within the skin. Conversely, photoinhibition is applicable to treatments requiring the inhibition of cells that produce a negative effect, such as those which produce scar tissue (scars are abnormal amounts and structural arrangement of collagen fibers). By the careful selection of the LED wavelength, pulse rate, pulse duration, and intensity, the activity of oil glands and priopionibacterium acnes (the acne bacteria) can be inhibited to reduce acne formation, oil gland activity, pore size, etc. Acne scarring could be treated by the photoactivation of cells which produce collagen in the vicinity of the depressed acne scars while photoinhibition could be used for raised thickened acne scars, thereby reducing their visibility.

In non-dermatological applications, photomodulation can be used to treat a wide variety of medical and veterinary conditions—tumor growth can be inhibited, cells within improperly functioning organs can be stimulated to improve the function of those organs, etc. An embodiment of the invention for internal application, for example, uses miniature arrays or single LEDs implanted in the body adjacent, for example, to a tumorous growth. The device can use a preprogrammed activation scheme or be controlled by a remote transmitter to subject the tumorous growth to a desired wavelength of light operating at a desirable pulse rate, pulse duration, and intensity to produce the photoinhibition of cell growth within the tumor. This could be accomplished with or without the interaction with exogenous target chromophores introduced by any of the methods of drug delivery known to this art.

Figure 1A:
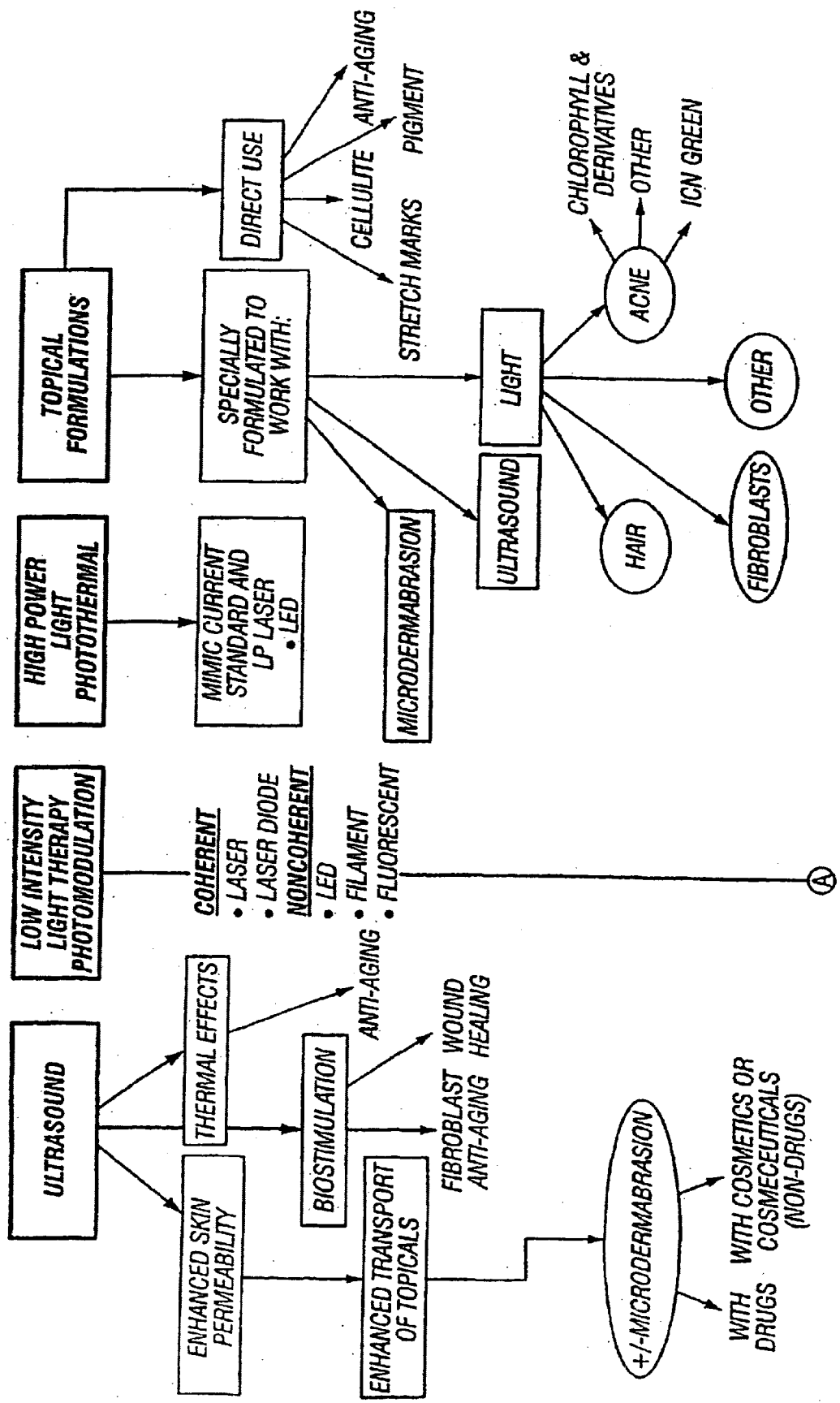
FIG. 1 is a schematical illustration of various treatment regimens, including the low level light method of the present invention which may also incorporate the use of topical formulations.
Figure 1B:
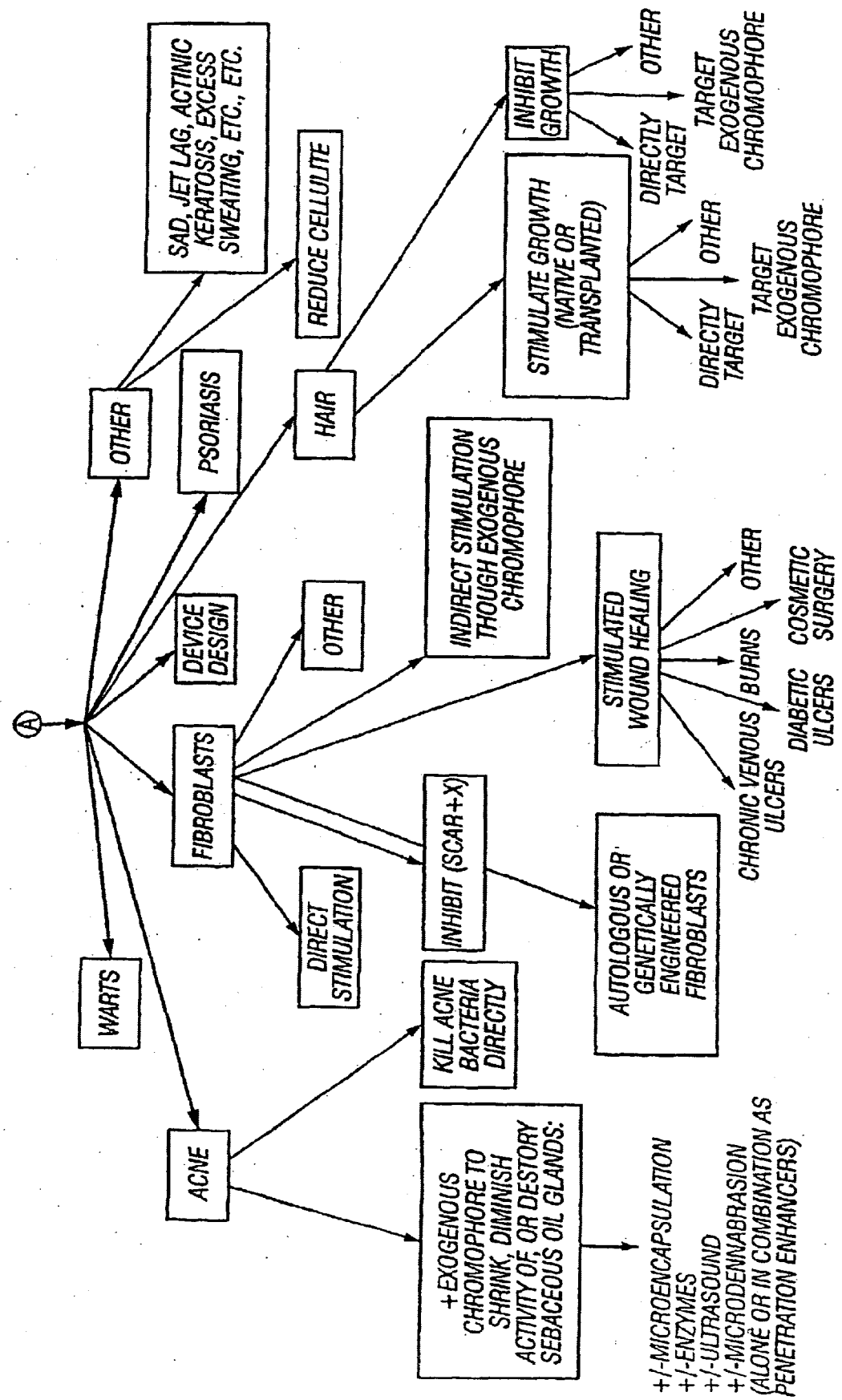
Figure 36:
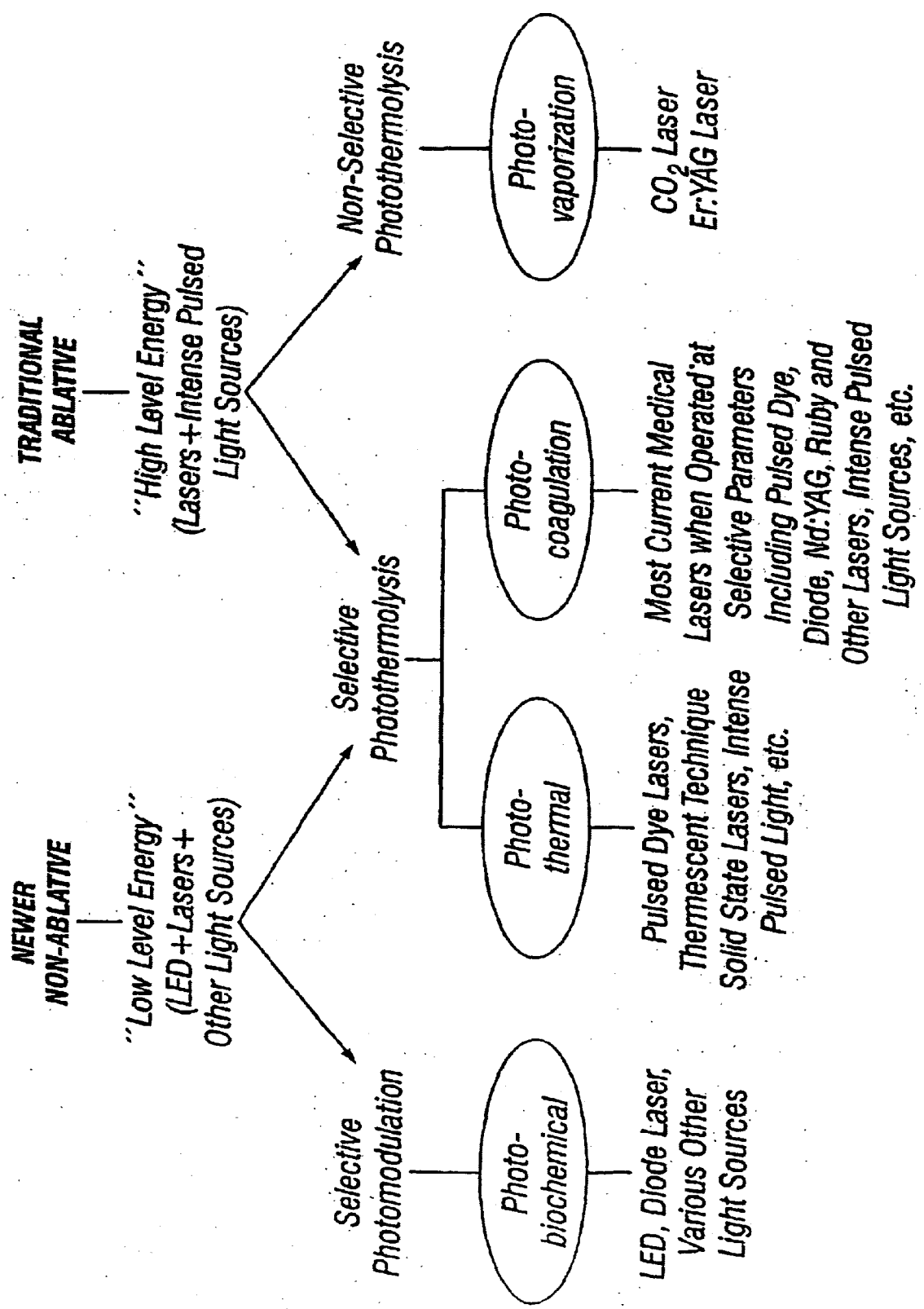
FIG. 36 a block flow diagram overview showing the interrelation of various treatments.

Further, it has been beneficially found that treatment of cells using LEDs does not require heating the cells to the point where thermal injury occurs, as prior art devices required. For example, to heal wounds using laser therapy, the cells had to be heated to the point where thermal injury occurred to trigger the growth of new collagen. Therapy using LEDs, according to the present invention, enables the direct activation of collagen producing cells or any living cells without using thermal injury as a trigger. The method of dermatological treatment without creating an 'open' wound is traditionally called "non-ablative". The prior art method of causing thermal injury which does create an active wound requiring wound care as a trigger for collagen growth and wound healing is called "ablative". Moreover, there are actually two distinct types of "non-ablative" skin rejuvenation: one method which produces thermal injury (the currently practiced methods) and one which does not produce thermal injury (the photomodulation method of the present invention). While the photomodulation treatment method does not require thermal injury to occur to produce wound healing, a minor degree of thermal injury can still occur during treatment according to the present invention, if high intensity LEDs are used and the target cells receive extended exposure. Nevertheless, it is important to distinguish that the critical difference between ablative and non-ablative treatment is the mechanism by which collagen generation is triggered—in the non-ablative method it is by using a specific pattern of light exposure to "turn on" the collagen producing cell, whereas with the ablative method it is by using light with a sufficient intensity to produce thermal injury (cells naturally react to thermal injury by producing collagen to repair the injury.) FIG. 1 illustrates the various treatment regimen according to the present invention and also those using lasers which can be used in conjunction with the non-ablative method of the present invention. FIG. 36 illustrated various treatment regimen which can be conducted in either an ablative or non-ablative manner.

Most preferred according to the present invention are LEDs which can produce a narrowband, multichromatic emission having a bandwidth of 5–20 nm, although a bandwidth up to several thousand nanometers is useful for various treatment regimens. Further preferred light sources are capable of delivery low intensity radiation to a target and operate in a power range of from about 250 nanowatts/cm2 to about 1 watt/cm2. More preferable, the power range of the emitter should be in the range of about 500 nanowatts to about 2000 nanowatts for a LED source having a narrowband (i.e., 5–20 nm bandwidth) emission centered at about 590 nm and 644 nm. These embodiments are preferred for 'non significant risk devices' which do not pose and eye hazard or exposure to high voltage but still produce clinical improvements on a wide range of disorders including wrinkle reduction and wound healing. In order to optimize clinical improvement but utilizing light intensities which and device designs and optoelectronic devices the combination of which may lead to classification at a higher risk level may require treatment regimens, however, will benefit from light intensities as high as 4 J/cm$^2$.

Figure 2A:
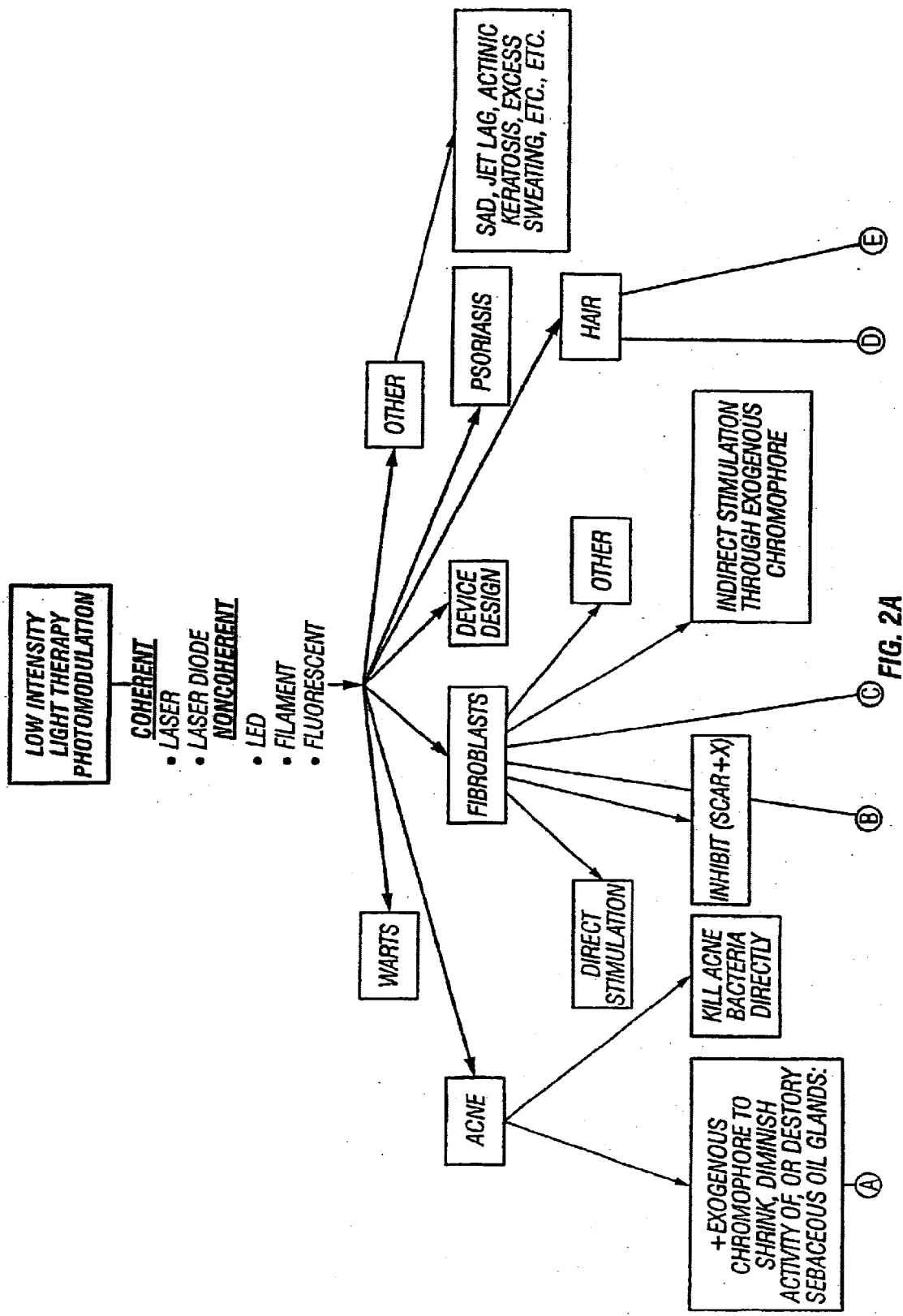
FIG. 2 is a schematical representation of treatment regimens pertaining to the use of low level light according to the present invention.
Figure 2B:
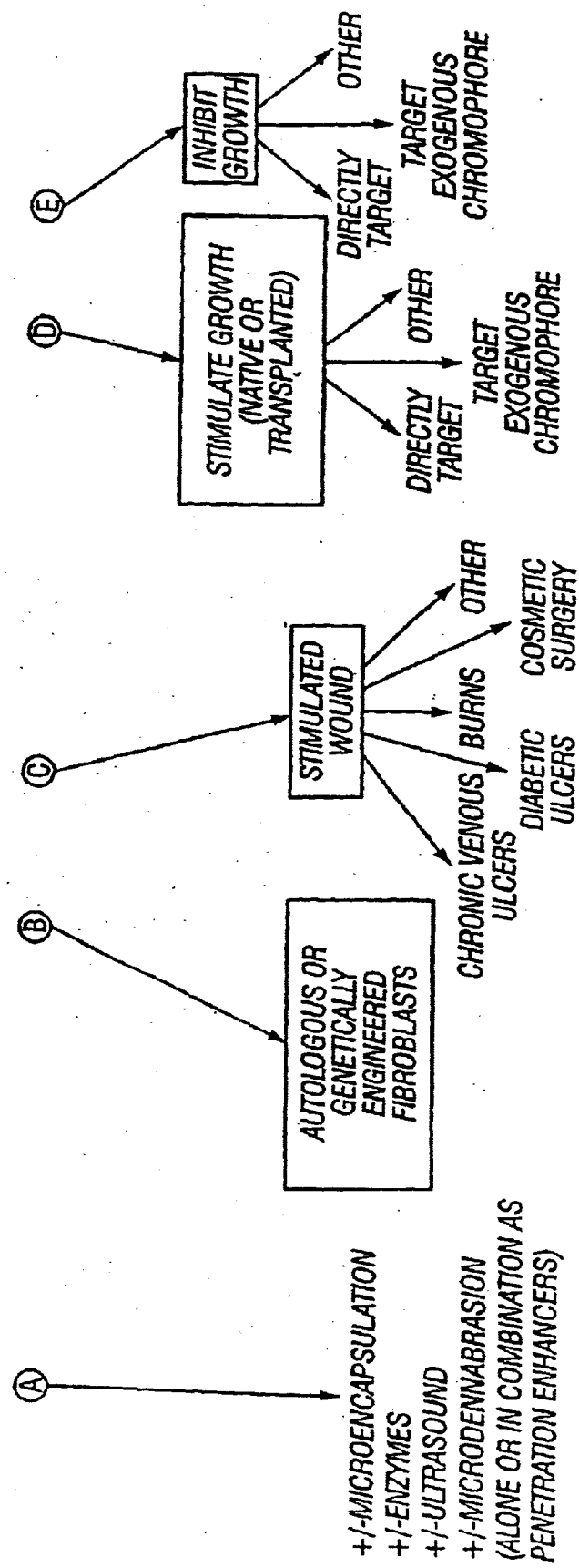
Figure 4:
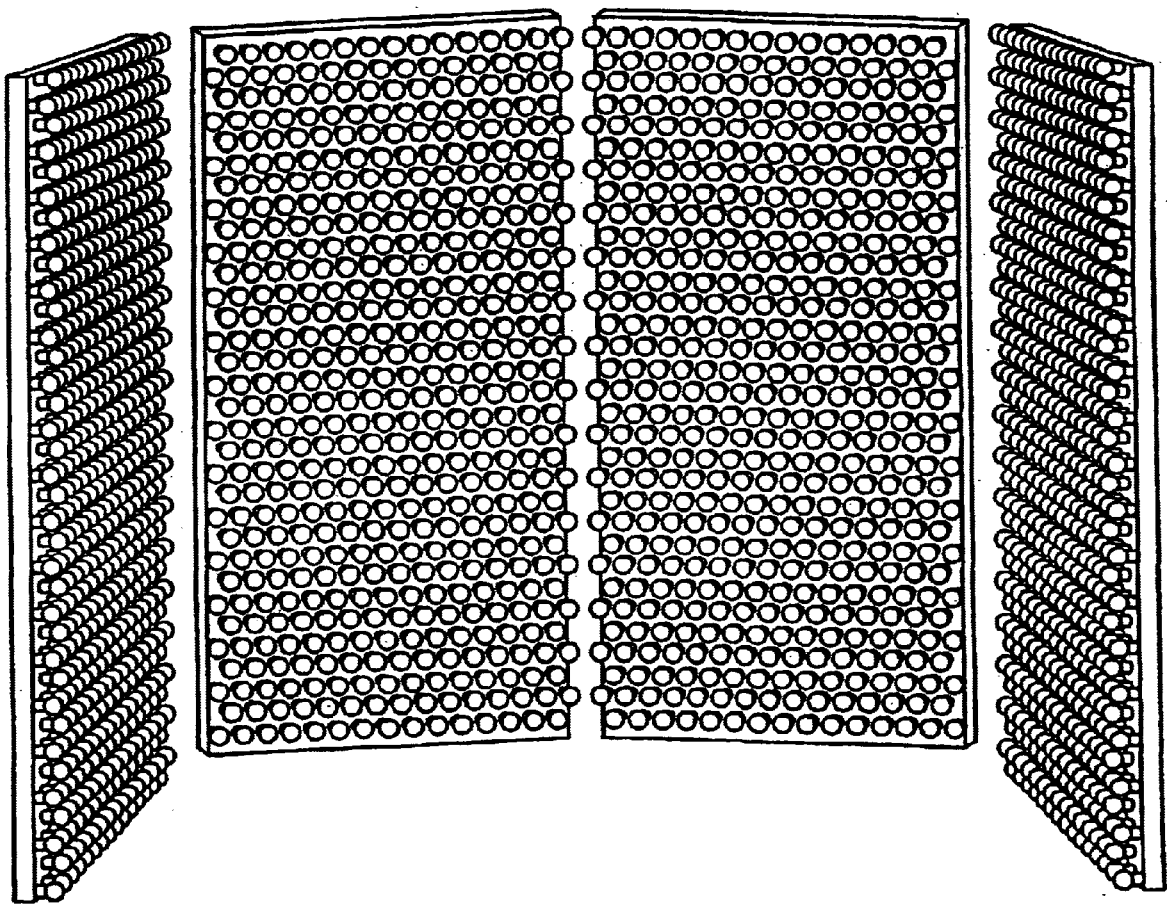
FIG. 4 is an illustration of a embodiment of a panel-style LED array for use according to the present invention.
Figure 35:
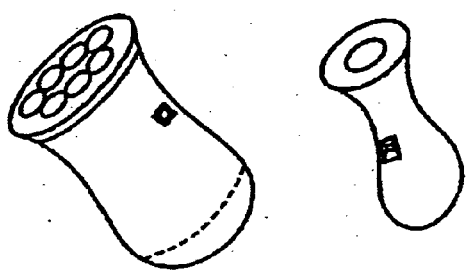
FIG. 35 a depiction of a hand-held battery powered LED device according to the present invention.

The LEDs of the device suitable for use in the present invention are arranged in panels having from about 100 to about 1000 LEDs per panel. In the preferred embodiment for clinical use, 525 LEDs per panel are used and 4 panels per are employed in the treatment system, as illustrated in FIG. 4. FIG. 2 shows an array of LEDs on a single panel. FIG. 3 shows a panel similar to that in FIG. 2 where the array of LEDS is covered by a diffuser to produce smooth, even application of the electromagnetic radiation to the target skin or living tissue to be treated. Another preferred embodiment is shown in FIG. 35 in which a hand-held device for use without clinical supervision that contains as few as 1–6 LEDs or as many as 50—100. Two embodiments are shown in FIG. 35—one with multiple LEDS and one with a single LED. While LEDS are shown in the previously mentioned Figures, one skill in the art will recognize that any of the narrowband, multichromatic emitters discussed herein are suitable for use in the hand-held embodiment and panel arrays.

Figure 5A:
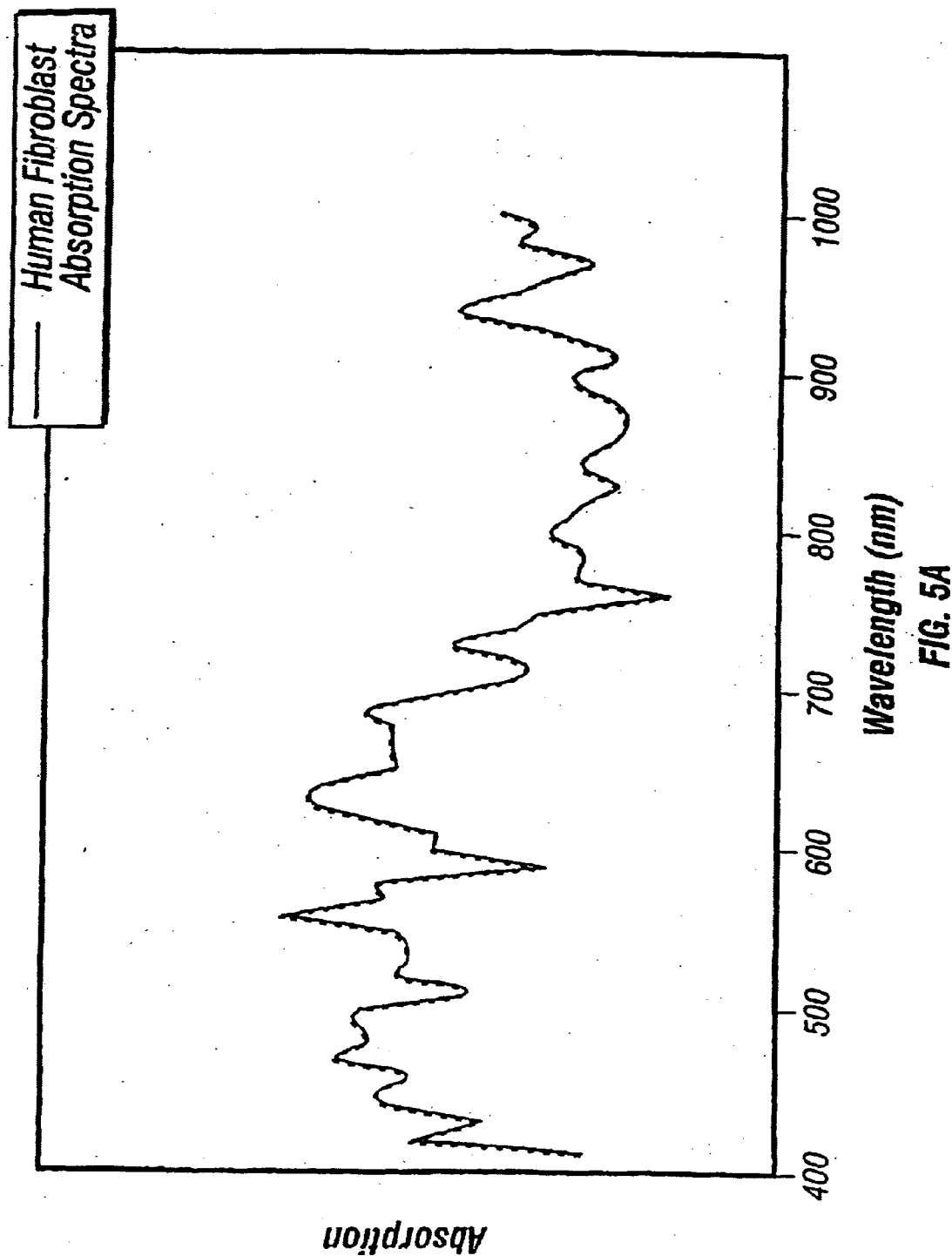
FIG. 5 is a graphical illustration showing the absorption spectrum of human fibroblast cells in a monolayer culture.
Figure 5B:
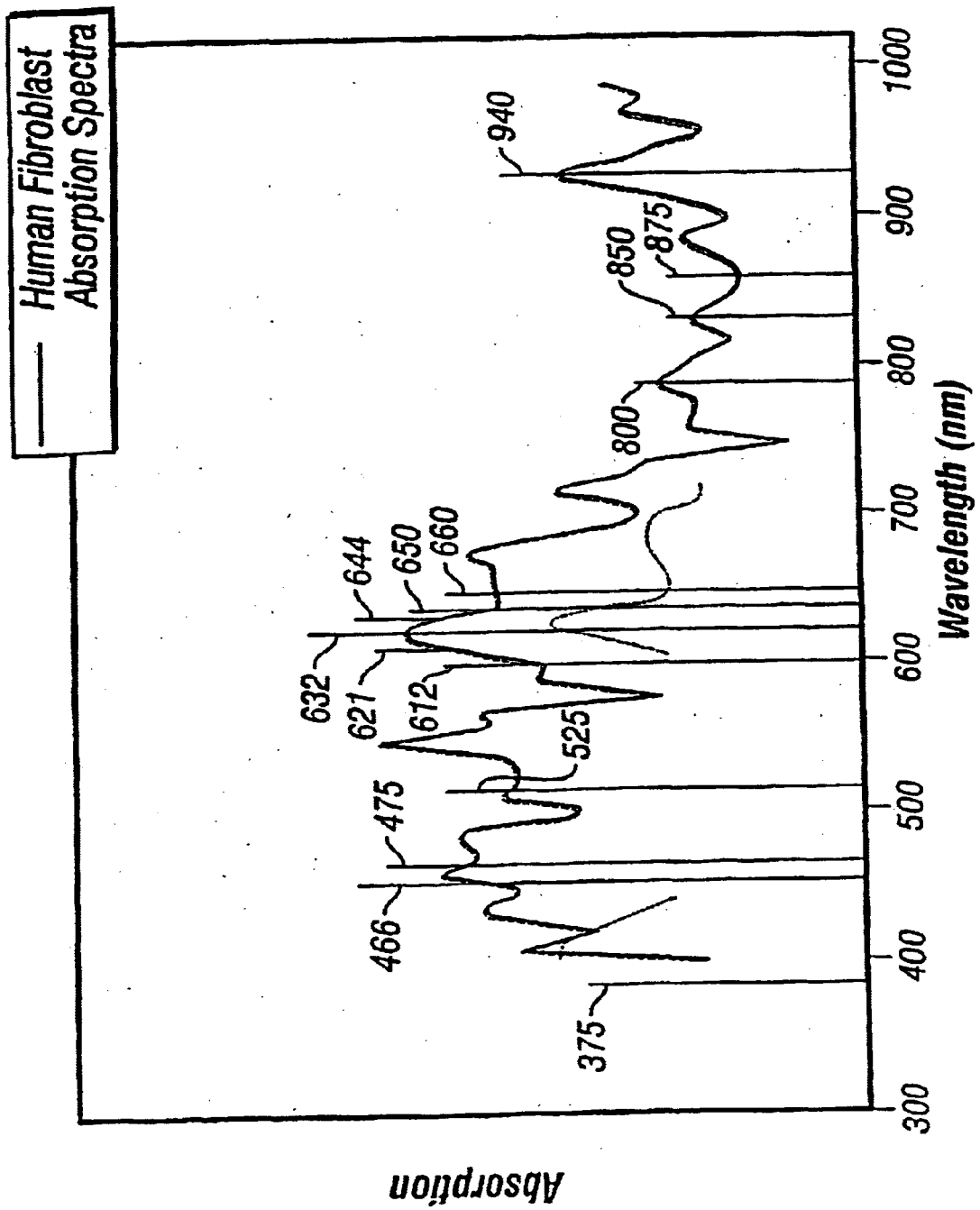
Figure 7:
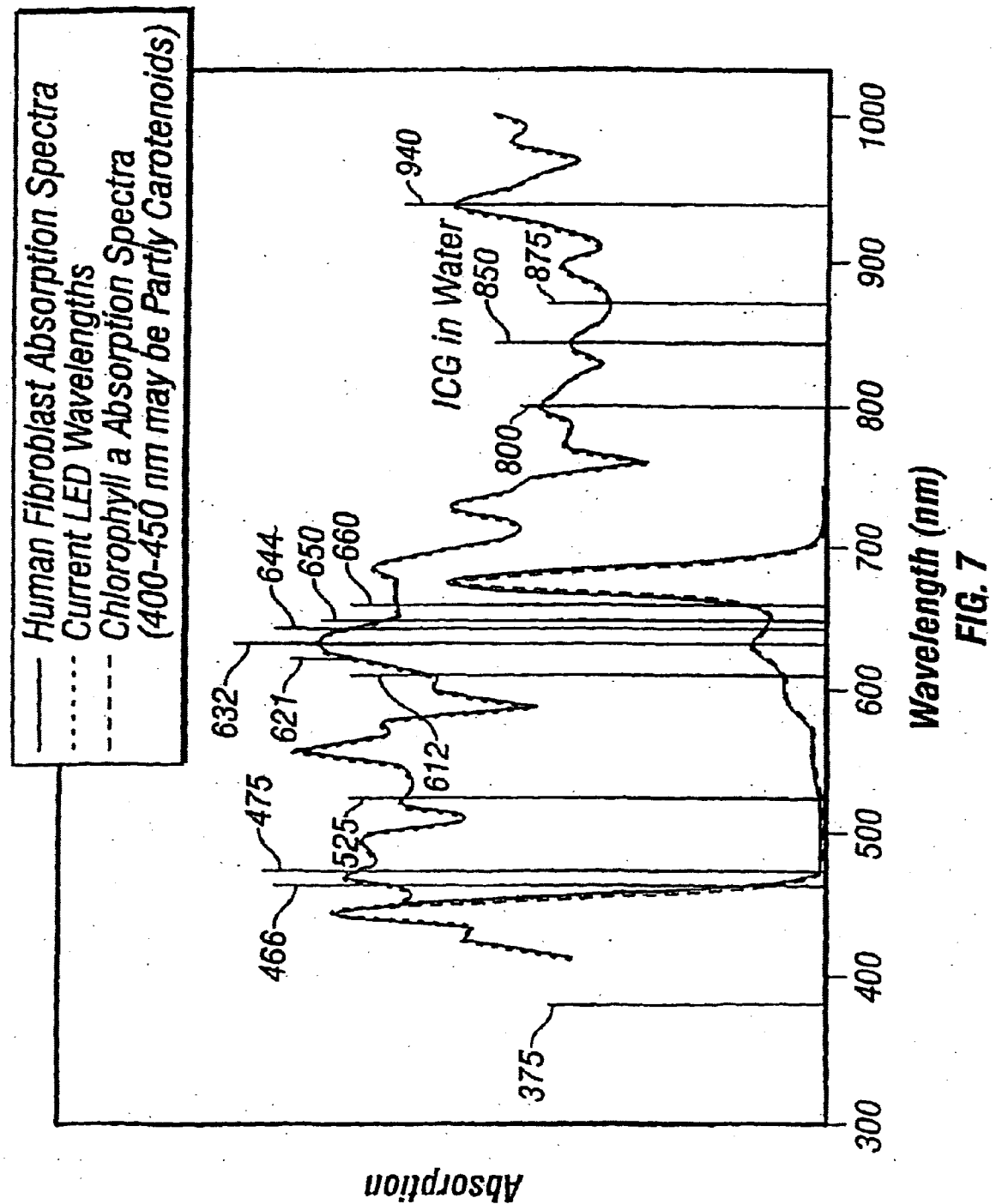
Figure 8:
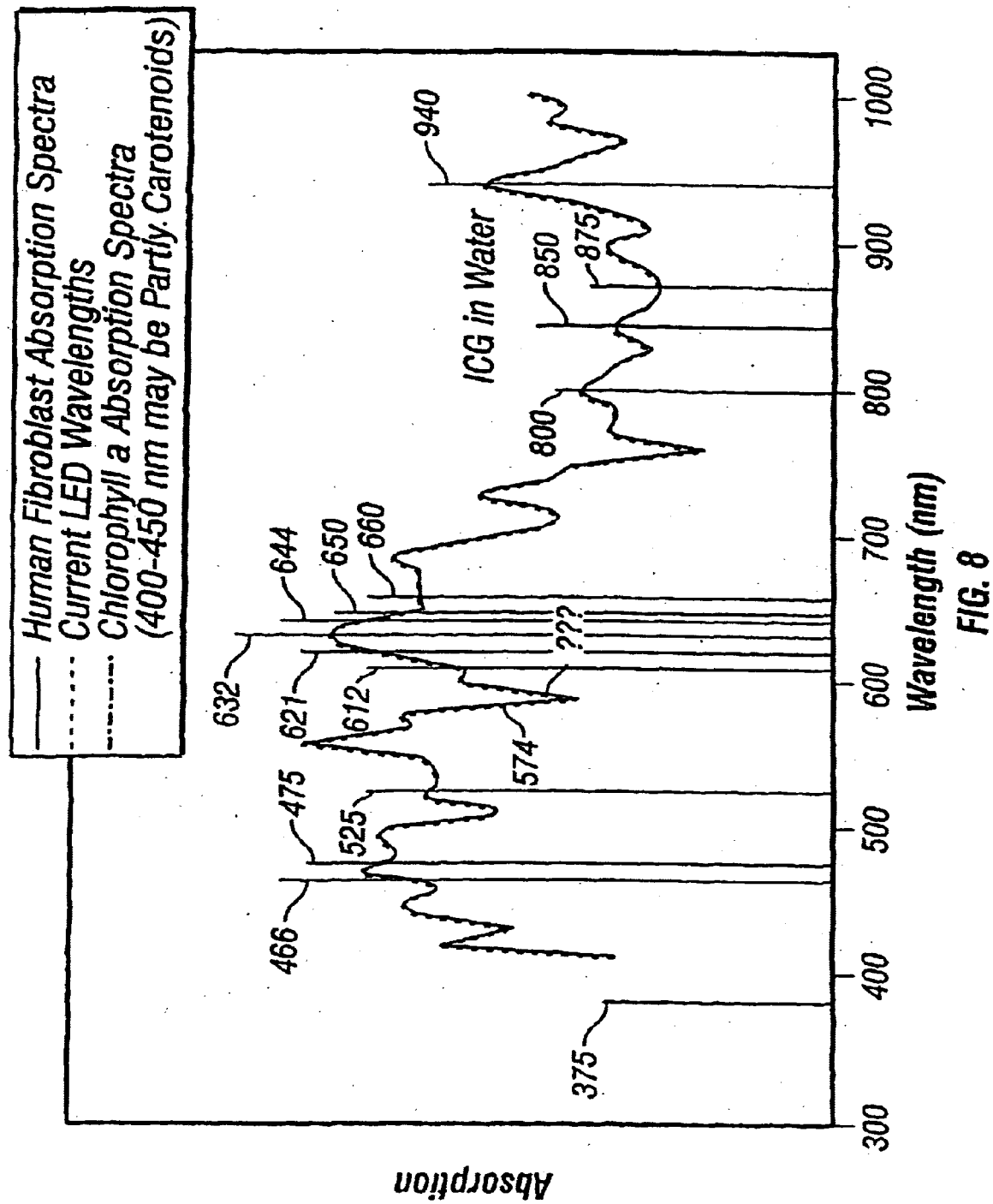
FIG. 8 is a graphical illustration of the absorption spectrum of human fibroblast overlayed with the wavelengths used by narrowband, multichromatic LED emitters of the present invention and also the absorption spectrum of chlorophyll B.
Figure 9:
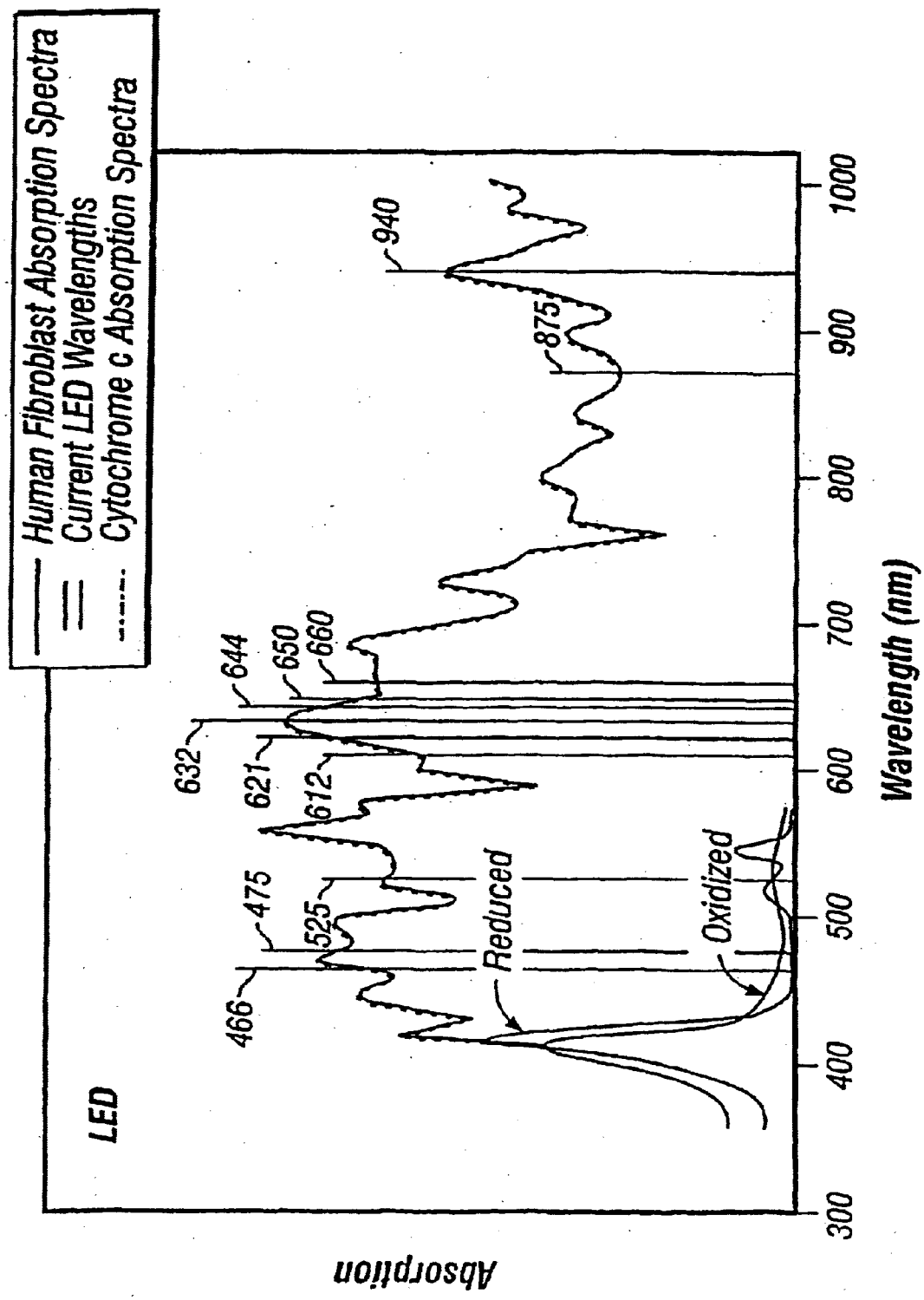
FIG. 9 is a graphical illustration of the absorption spectrum of human fibroblast overlayed with the wavelengths used by narrowband, multichromatic LED emitters of the present invention and also the absorption spectra of both reduced and oxidized cytochrome C.
Figure 10:
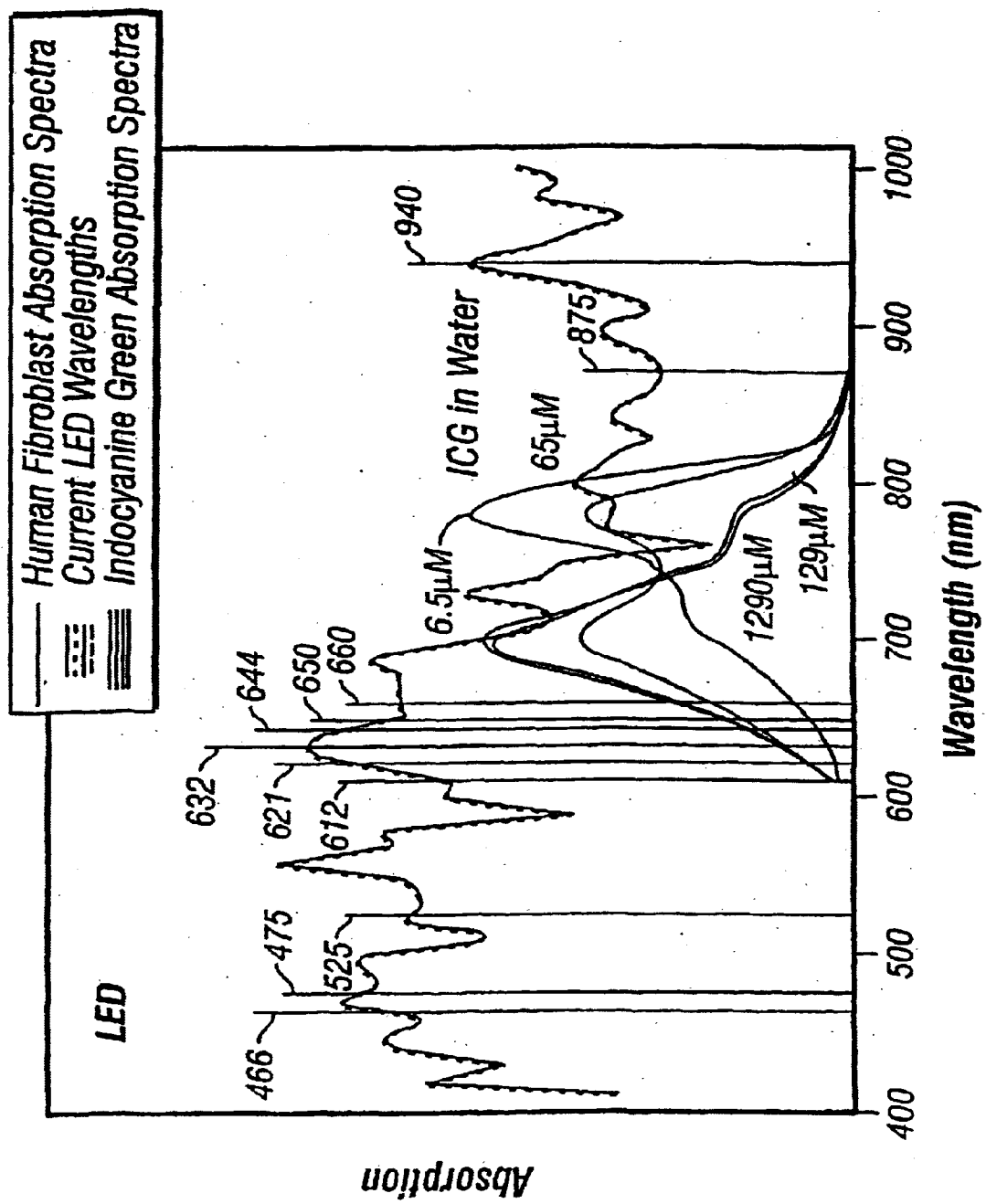
FIG. 10 is a graphical illustration of the absorption spectrum of human fibroblast overlayed with the wavelengths used by narrowband, multichromatic LED emitters of the present invention and also the absorption spectrum of indocyanine green.
Figure 11:
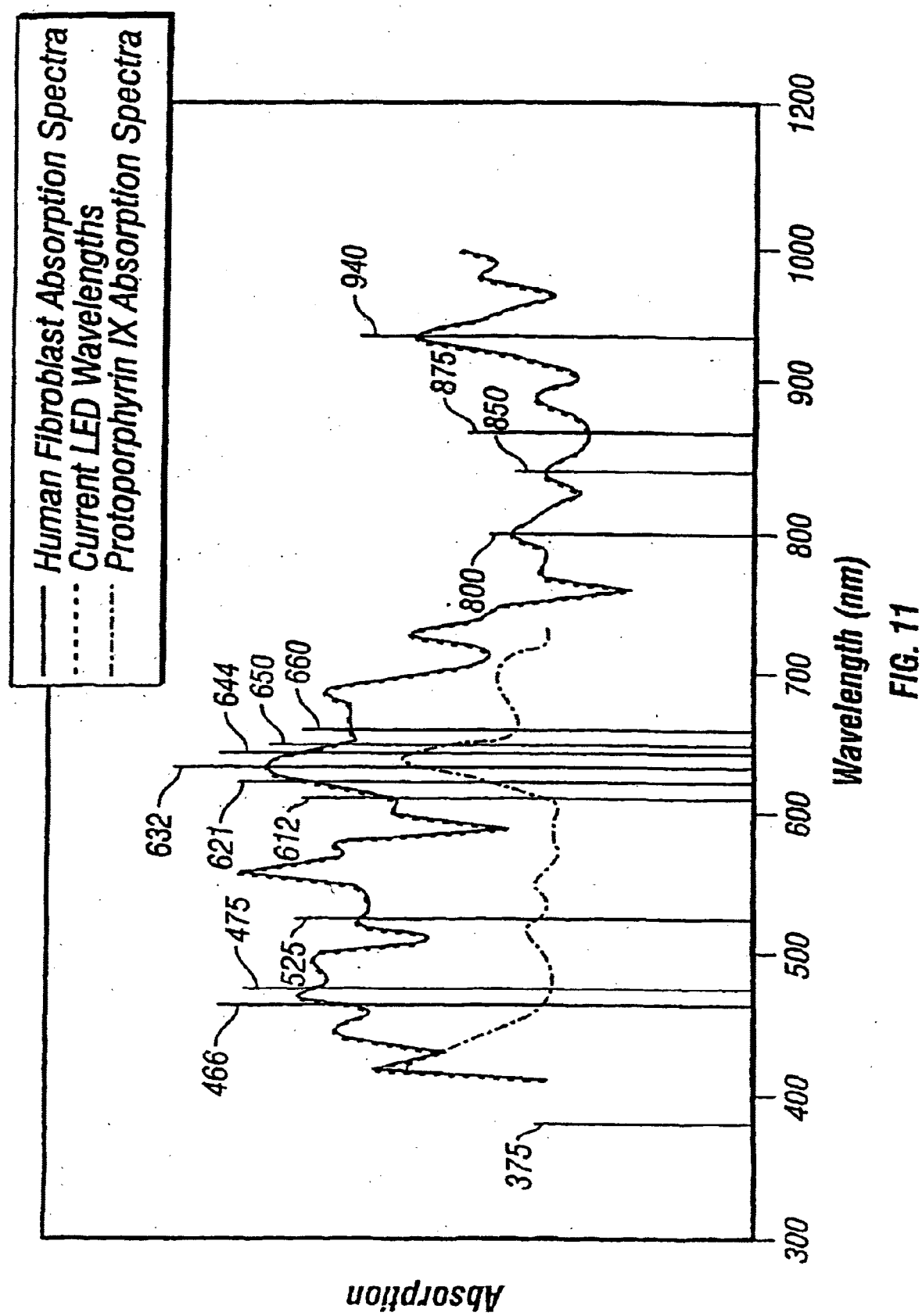
FIG. 11 is a graphical illustration of the absorption spectrum of human fibroblast overlayed with the wavelengths used by narrowband, multichromatic LED emitters of the present invention and also the absorption spectrum of protophorphyrin IX, one of the active chromophores in acne bacteria.
Figure 12:
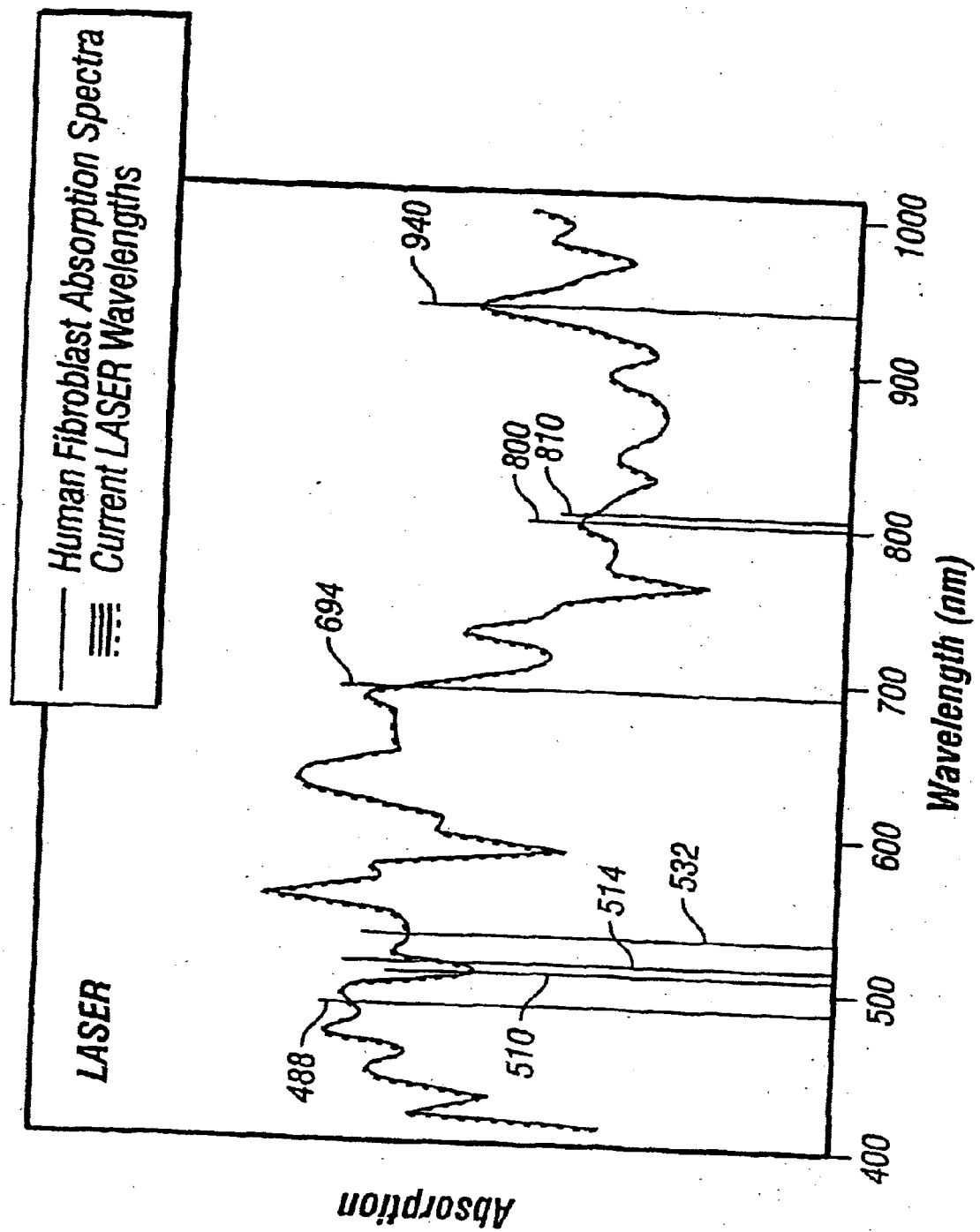
FIG. 12 is a graphical illustration of the absorption spectrum of human fibroblast overlayed with the wavelengths used by laser emitters.
Figure 33A:
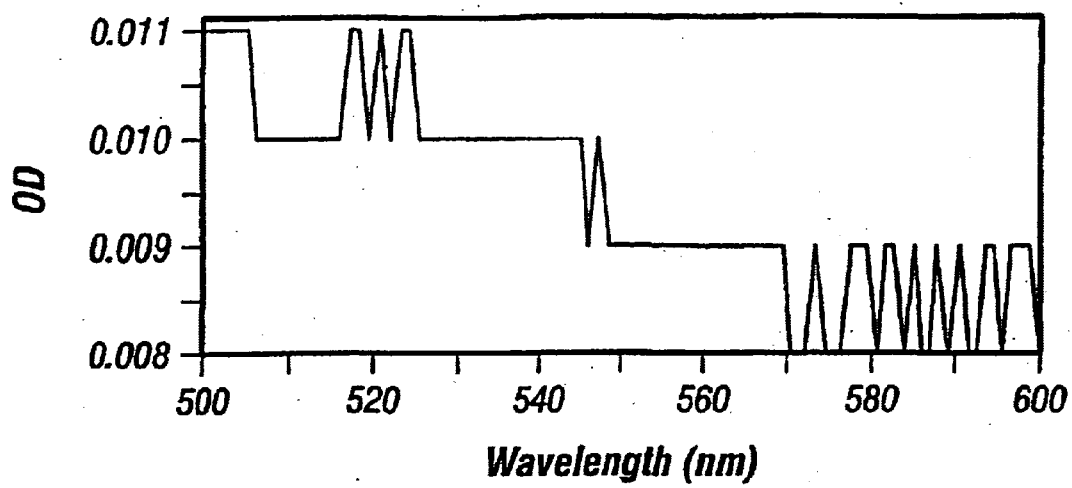
FIG. 33 shows absorption spectra of human fibroblast cells in monolayer tissue culture from 3 different patients to illustrate the natural variation in absorption maxima.
Figure 33B:
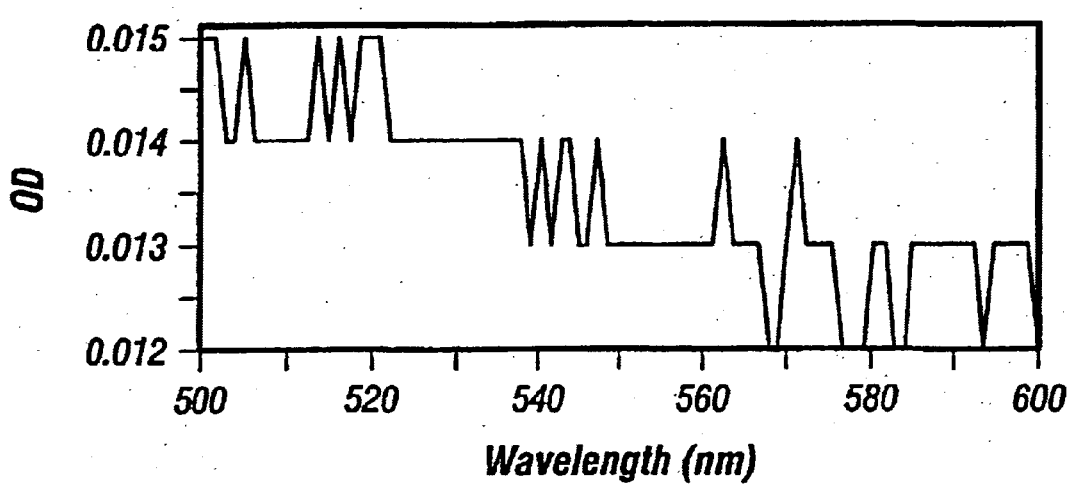
Figure 33C:
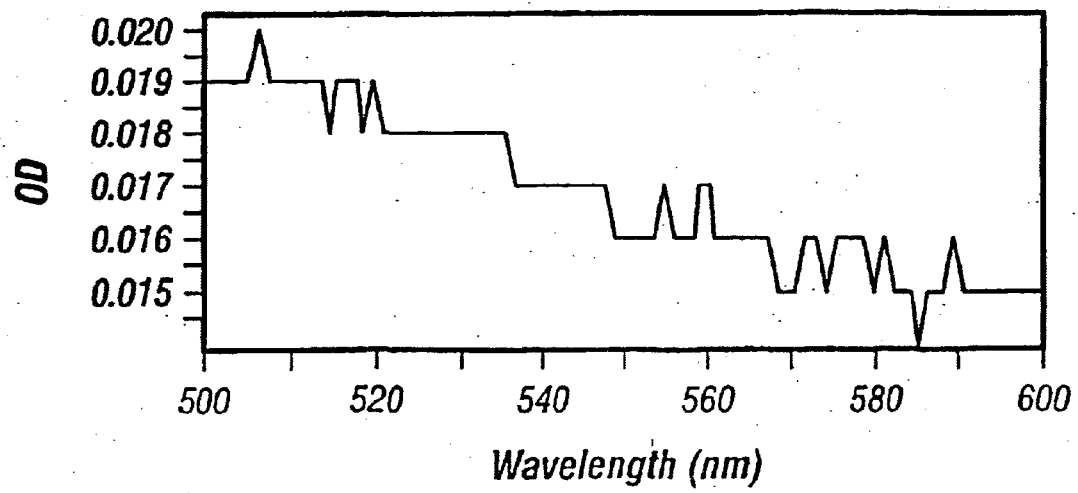

The hand held device of the present invention could be battery powered and permit treatment without the need for the patient to make an office visit. Such a device is particularly well-suited for the treatment of acne, hair removal, hair growth stimulation, vitiligo, psoriasis, stretch marks, herpes fever blisters, cuts, skin abrasions, bruises, dark under eye circles, liver spots, wrinkle removal, and other dermatological conditions. While many wavelengths can be used according to the present invention, depending on the type of treatment administered, preferred wavelengths for LEDs include 375 nm, 466 nm, 473 nm, 535 nm, 574 nm, 590 nm, 612 nm, 621 nm, 630 nm, 644 nm, 650 nm, 875 nm, 880 nm, 940 nm, etc. which can be used individually or in combination. Drawing FIG. 5 shows the absorption spectrum for human fibroblast cells in monolayer tissue culture. For treatments where photomodulation (i.e., photoactivation or photoinhibition of cells) of fibroblast cells is desired, preferred light sources will be able to emit wavelengths where the fibroblast absorption is high, i.e., the local maxima along the absorption curve. FIG. 6 illustrates the absorption spectra for human fibroblast in a monolayer culture along with the wavelengths of commonly available commercial LED devices superimposed thereon. FIGS. 7–11 show the absorption spectra of human fibroblast in a monolayer culture superimposed with the absorption spectra of various exogenous chromophores. FIG. 12, for comparison, shows the absorption spectra of human fibroblast in a monolayer culture superimposed with the wavelengths of common, commercially available laser devices. FIG. 33 shows the absorption spectra for 3 different human fibroblast cell lines and illustrates the variations among them. When using a monochromatic light source, only a single wavelength of light is produce. If this wavelength does not correspond well with the fibroblast spectra of the patient, that patient may not respond well to treatment. Using a narrowband, multichromatic light source, however, will permit effective treatment for a much larger group of patients because it is not necessary that the aborption peaks and minima of the patients' fibroblast correspond exactly to the dominant wavelength of the light source. Since LEDs and other narrowband emitters of the present invention emit light in a narrow spectrum around the dominant band, minor fluctuations and variations of the absorption of the target tissue of various patients will not reduce their ability to reduce to treatment.

Figure 13A:
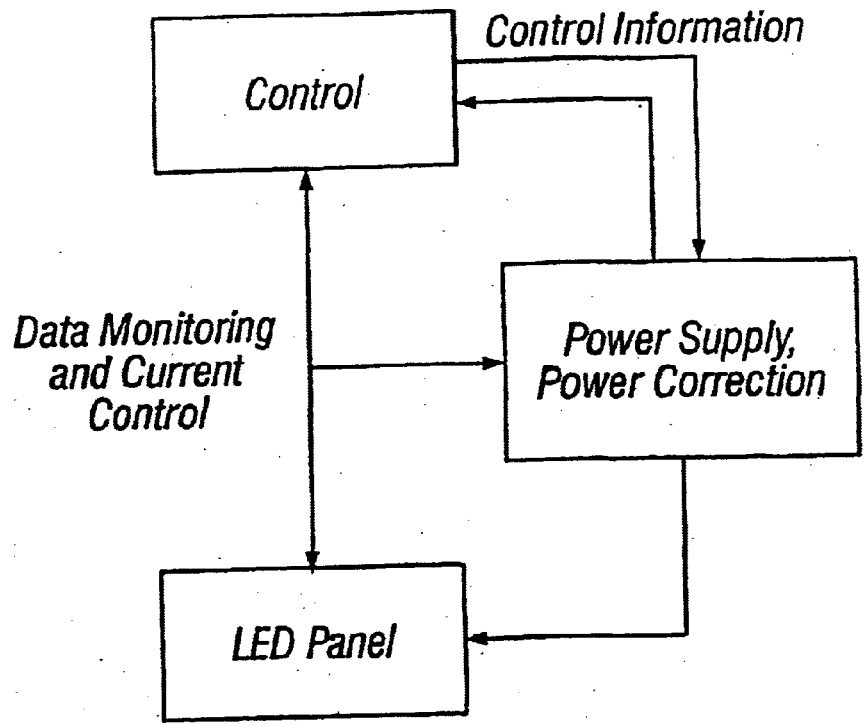
FIGS. 13A and B illustrates a plurality of individual optoelectronic devices connected in series and in parallel.
Figure 13B:
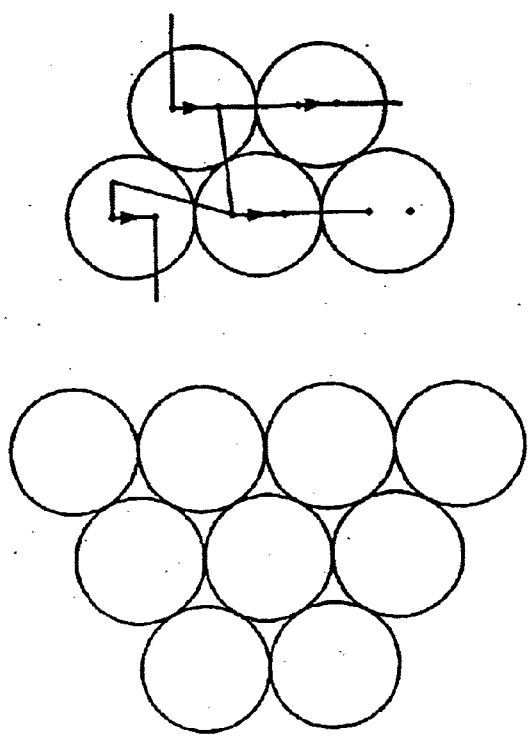
FIG. 13B is a schematic representation of an example of combined serial (from left to right across the row) and parallel wiring (top and bottom across the row); and a top plan view of an arrangement of LEDS in a close packed array of the present invention.

Although those skilled in the art of using such devices will be readily able to assemble and operate the light emission device of the present invention, as illustrated in block diagram form in FIG. 13a the preferred device includes a control box unit for providing power to the emitters and varying the intensity of the light they produce; at least one panel of LED emitters connected to the control box unit; a pulse generator unit for setting the frequency and duration of pulses emitted by the LED emitters; and ancillary power cords and cables to permit operation. FIG. 13b illustrates the wiring connection between LEDs arranged in an array and also a view of the close packed LEDs, without wiring, in the array.

The medical treatment regimen of the present invention relates to a method of stimulating or inhibiting the biological activity or growth of living cells, subcellular components, living tissue and/or organs. As previously mentioned, the present invention may be used, for example, to stimulate or inhibit the biological activity or growth of human or animal fibroblasts. Such fibroblasts may include native fibroblasts, autologous fibroblasts, and/or genetically modified fibroblasts.

Effects on living cells or living tissue may be produced directly or indirectly through interaction with another substance which, after irradiation, produces such effects on living cells or living tissue.

Pretreatment regimens can include light alone, light in combination with exogenous chromophores, and the use of exogenous chromophores alone, depending on the nature of the treatment desired. Exogenous chromophores may includes hormones, growth factors, catalysts, cofactors or other needed agents for the appropriate biochemical and metabolic pathways, some of which may include metalloproteinase inhibitors (for example one of these is useful in reducing the degradation of collagen by the matrix metalloproteinase formerly called collagenase). Commercially available topical compositions particularly contemplated for use according to the present invention include Appligraf, Dermologen, Isolagen, Zyderm and Zyplast. Suitable active agents for use in topical compositions applied to the skin in accordance with the present invention include one or more of Vitamin C, Vitamin E, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, an antioxidant, a phytoanthocyanin, a phytonutrient, a botanical product, a herbaceous product, a hormone, an enzyme, a mineral, a genetically engineered substance, a cofactor, a catalyst, an antiaging substance, insulin, trace elements (including ionic calcium, magnesium, etc), minerals, Rogaine, a hair growth stimulating substance, a hair growth inhibiting substance, a dye, a natural or synthetic melanin, a metalloproteinase inhibitor, proline, hydroxyproline, an anesthetic substance, chlorophyll, copper chlorophyllin, carotenoids, and derivatives and analogs of the above items both natural and synthetic.

Figure 14:
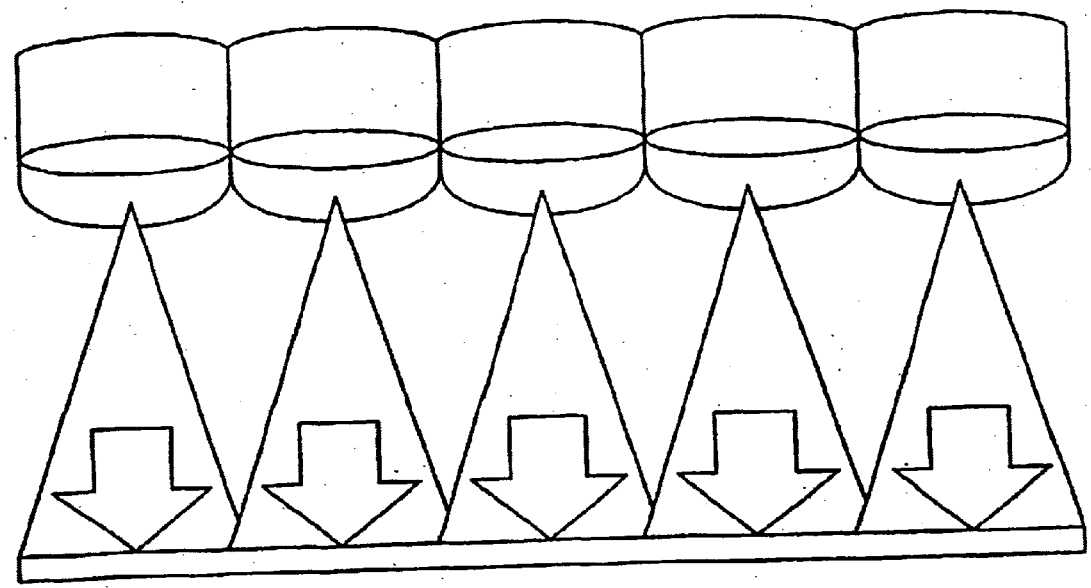
FIG. 14 illustrates in perspective the spacing of the optoelectronic devices of the present invention in close packed spacing in one dimension.
Figure 15A:
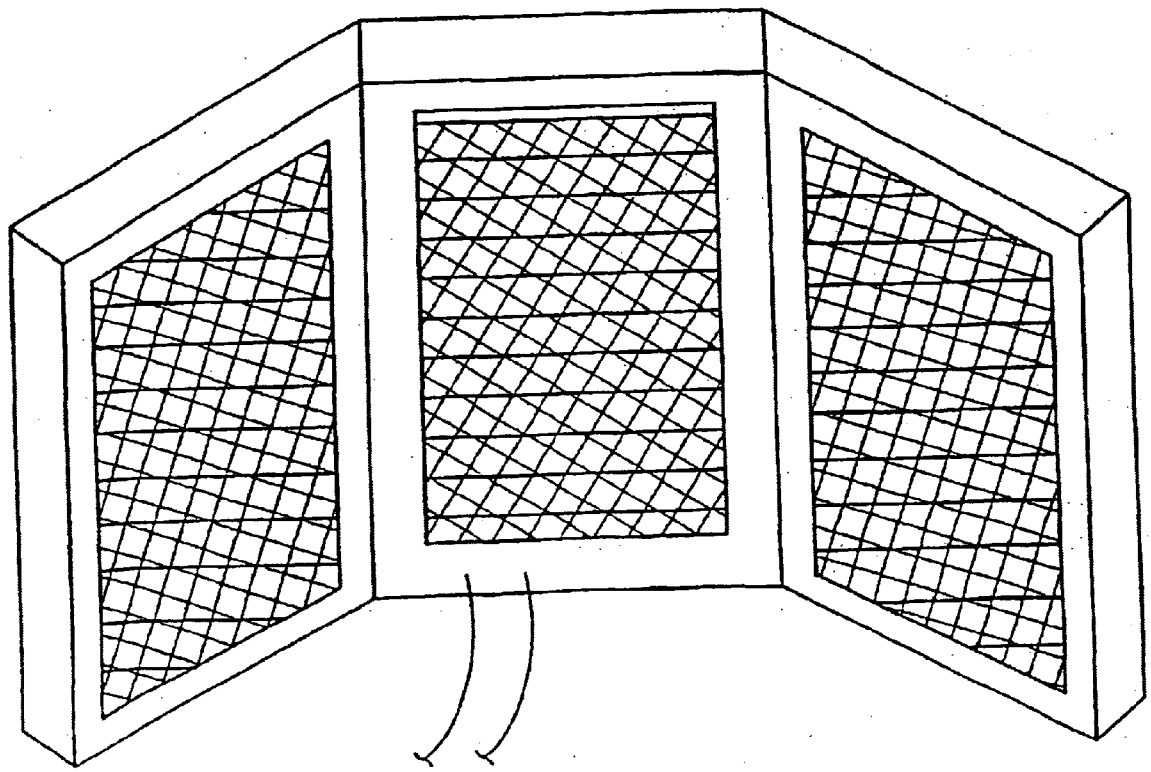
FIGS. 15A–C show an array of optoelectronic devices arranged into three panels. The cross hatched areas represent protective covers. The covers may transmit light or may diffuse light. The set of three panels shown in FIG. 15A are hinged to allow adjustment, so that the arrangement resembles a three panel make-up mirror.
Figure 15B:
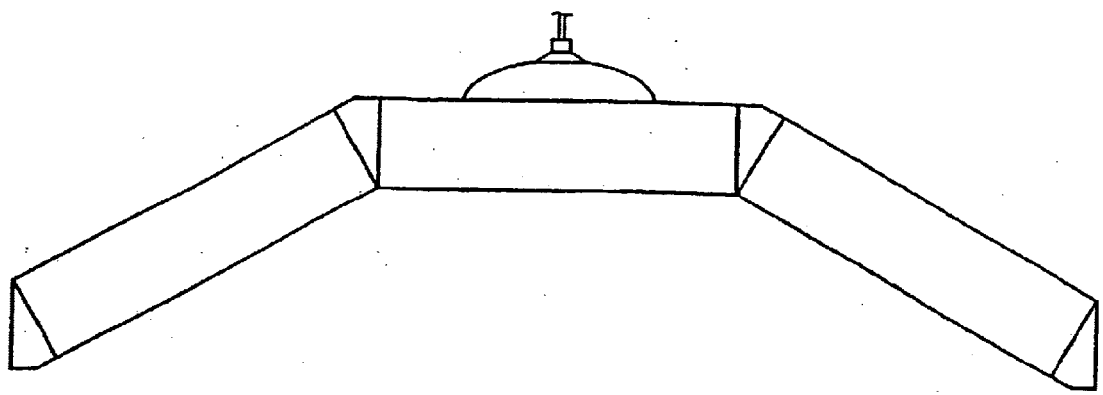
Figure 15C:
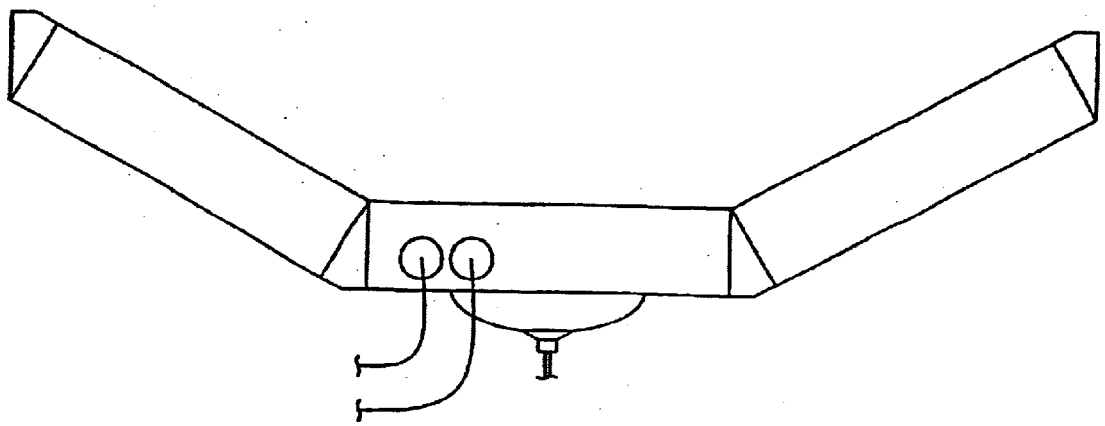
Figure 16:
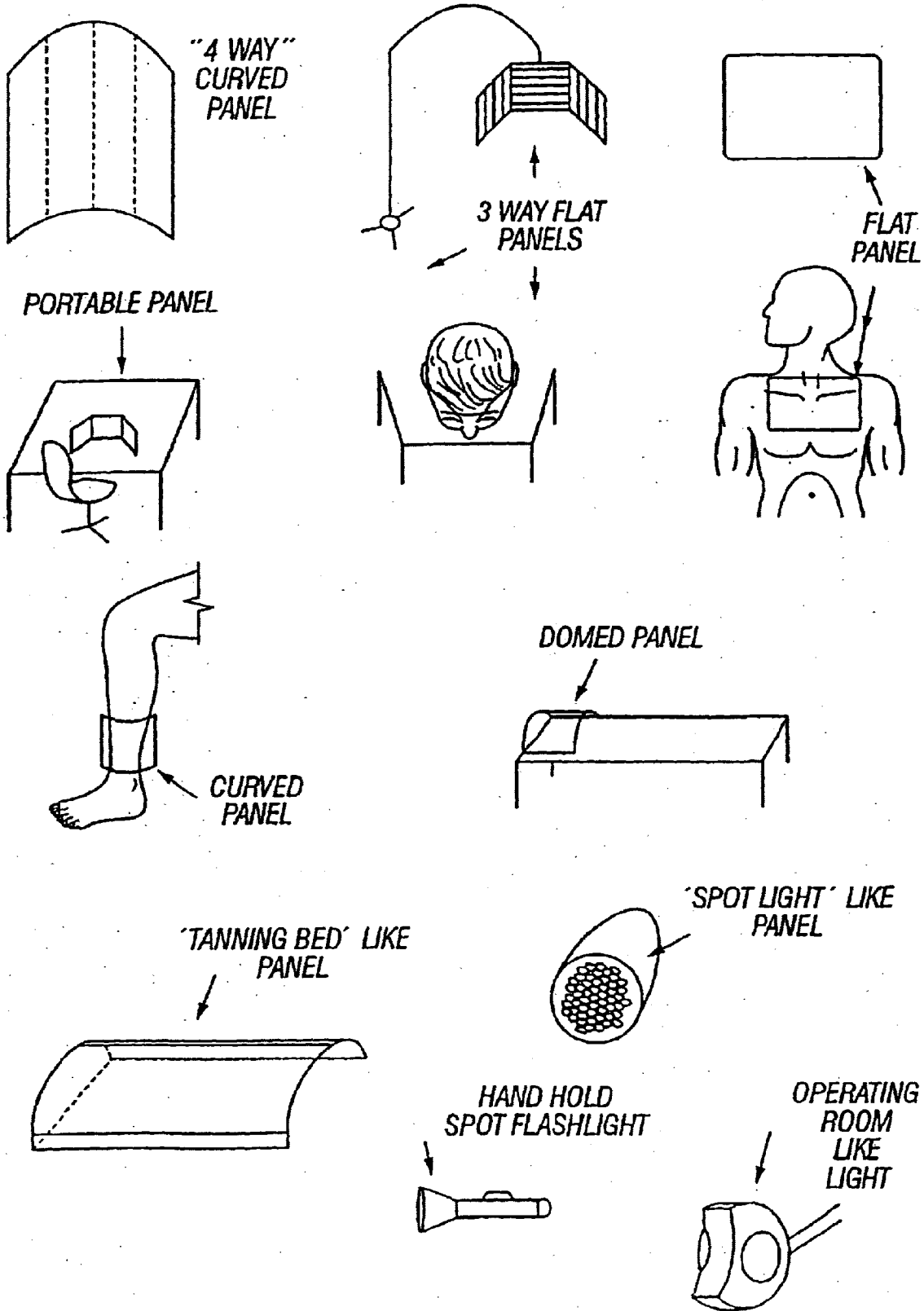
FIG. 16 is an illustration of illustrate examples of possible configurations of arrays for various treatment applications.

In accordance with the present invention the design, configuration, assembly and power of one or more optoelectronic devices may be modified to generate a desired energy and operating parameters in a beam of radiation, i.e., as illustrated in FIG. 14, to accomplish the method and also for the apparatus to deliver the beam. Very low powers (nanowatts) can be used with narrowband, multichromatic devices to produce photomodulation of living tissue, or high power (watts) can be used to mimic the function of traditional laser treatment, if so desired, without the benefits associated with non-ablative treatment. FIG. 15a–c illustrate views of a generic panel-style array suitable for use with any narrowband, multichromatic emitter for electromagnetic radiation suitable for use in accordance with the present invention. FIG. 16 shows alternate embodiments of the mounting apparatus for the radiation emitters to perform various types of medical treatment. FIG. 17a shows the typical divergence of an LED emitter. The overlap of LEDs in the array can affect the seamlessness of skin treatment, i.e., to avoid blotching or unevenness in the treatment that can be caused by "hot spots" of areas of overlap from multiple diverging beams (see FIG. 17b). To improve light focus, the emitter may be coupled with an optical waveguide, such as that shown in FIG. 17c. The waveguide is of the form known in the art and is typically comprised of an optical fiber. Such a device permits the insertion of the waveguide into the the body of a living patient for highly localized internal treatment (tumor inhibition treatment or other internal ailment.) For external treatment using multiple LEDS, a wide variety of beam divergence patterns are possible, as shown in FIGS. 18a–c. The most preferred is that which produces the most even application of radiation to the skin being treated and can vary from patient to patient and for different afflictions being treated.

The invention may be used on human skin for the treatment of wrinkles and other changes related to photo-aging or chronologic aging, for the treatment of diseases including skin diseases, for the reduction of acne and related disorders such as rosacea, folliculitis, pseudofolliculitis barbae or proliferative or papulosquamous disorders such as psoriasis, for treating the pancreas in diabetes, for the stimulation or reduction of hair growth, and for reduction of cellulite, warts, hyperhidrosis, veins, pigment problems, tattoos, vitiligo, hypopigmentation, melasma,scars, stretch marks, fungal infections, bacterial infections, inflammatory, musculoskeletal problems (one example is tendonitis or arthritis), to improve healing of surgical wounds, burn therapy to improve healing and /or to reduce scarring, cellulute reduction, improving circulation within the skin, in vitro fertilization enhancement, other skin cell lines like melanocytes, keratinocytes, adipocytes, etc.

The present invention may interact with another substance to alter the structure or function of the skin, the hair and the nails or any living cell, tissue, organ both human and animal.

The present invention may be useful in improving wound healing, including but not limited to chronic skin ulcers, diabetic ulcers, thermal burn injuries, viral ulcers or disorders, periodontal disease and other dental disease. The present invention may be useful in enhancing the effects of devices which create an injury or wound in the process of performing cosmetic surgery including non-ablative thermal wounding techniques for treating skin wrinkles, scars, stretch marks and other skin disorders. Under such circumstances, it may be preferable to use convention non-ablative thermal treatments in combination with the non thermal photomodulation method of the present invention. The present invention may also be used in conjunction with micro or surface abrasion, dermabrasion or enzymatic or chemical peeling of the skin or topical cosmeceutical applications, with or without ultrasound application to enhance treatment, as the removal of the stratum corneum (and possibly additional epithelial layers) can prove beneficial for some treatment regimen. In one embodiment of the invention, the stratum corneum layer of the skin is at least partially removed to aid in treatment. The stratum corneum is the outermost epithelial layer characterized by a structure, a function, a thickness and a permeability and wherein modifying at least a portion of the stratum corneum comprises at least one of the steps of stripping, removing, thinning and diminishing at least one of the structure, function, thickness and permeability of the stratum corneum by at least one of a mechanical, abrasive, photo acoustic, ablative, thermal, chemical, abrasive and enzymatic wherein the step of modifying at least a portion of the stratum corneum comprises at least one of the steps of solvent stripping, tape stripping, scrubbing, laser ablation, laser vaporization, chemical peeling, micro dermabrasion, and laser treatment using a high peak power, short pulse duration laser.

Biostimulation and bioinhibition are each part of a spectrum of cellular effects that may be produced by a single device or plurality of devices using different parameters. Generally, the term biostimulation can be used interchangeably with the term photoactivation and the term bioinhibition can be used interchangeable with photoinhibition when the biological activity is induced by light. The general term to describe both photoinhibition and photoactivation is photomodulation—meaning that light induces a response by the biological material. Production of the desired cellular effect may depend largely upon the selection of certain parameters. Several of these parameters are described in further detail below.

There are a wide variety of different operating parameters that may comprise conditions effective to produce beneficial cellular effects such as triggering cellular regeneration or photoactivation or photoinhibition which, for example, could reduce the activity of oil glands in the skin, thereby reducing acne bacteria. Also, targeting a natural chromophore for photoactivation or photoinhibition such as acne bacteria, is possible, in addition to targeting exogenous chromophores like carotenoids, chlorophyll and its derivatives including copper chlorophyllin and other dyes such as indocyanine green dye, methylene blue dye, and similar compositions known to those skilled in the art. Exogenous chromophores are substances which absorb light or electromagnetic radiation in at least one narrow band of wavelengths and assist with the treatment method and system of the present invention by applying them to an area of the skin to be treated. Selection of the exogenous chromophore is determined by the absoroption spectra of the chromophores on human fibroblast and is dependent on the wavelength of the narrowband multichromatic emitter used for treatment. In accordance with a preferred embodiment of the invention, the chromophore will aid in treatment by enabling at least the dominant or central wavelength of the narrowband, multichromatic radiation to penetrate at least the stratum corneum layer of the skin and permitting the photomodulated of living tissue below the stratum corneum. In some instances, the photomodulated tissue can be below all of the epithelial layers of the skin.

Some examples of possible operating parameters may include the wavelengths of the electromagnetic radiation to which the living tissue containing cells to be regenerated, stimulated, or inhibited, the duration of pulses (pulse duraction) of the electromagnetic radiation, the number of pulses, the duration between pulses, also referred to as repetition rate or interpulse interval. Intervals between treatments can be as long as hours, days, weeks, months, etc.; and the total number of treatments is determined by the response of the individual patient. Further, treatment regimens using a combination of more than one wavelengths either simultaneous or in sequence may be used. As well, the energy intensity of the radiation as measured at the living tissue (typically measured in Joules per centimeter squared, watts per centimeter squared, etc.), the pH of the cell, tissue or skin, the skin temperature, and time from application to treatment with a light source, if used with exogenous chromophore (which can be topical, injected, driven in with ultrasound, or systemic) is determined by the nature of the treatment and is further illustrated in the Examples.

Wavelength—Each target cell or subcellular component, or molecular bond therein, tends to have at least one unique and characteristic "action spectrum" at which it exhibits certain electromagnetic or light absorption peaks or maxima FIG. 3, for example, shows the absorption spectrum of one line of human fibroblast cells in monolayer tissue culture. Different cell lines (of the same cell—for example fibroblasts from 3 different patients) exhibit some differences in their absorption spectra and thus using narrow band multichromatic light (rather than monochromatic light) is also useful in producing the optimal clinical effect. When these cells or subcellular components are irradiated with wavelengths corresponding to the absorption peaks or maxima, energy is transferred from the light photon and absorbed by the target. The particular features of the delivered energy determine the cellular effects. The complexity of these combinations of parameters has produced much confusion in the prior art. Basically, the wavelength should roughly correlate with an absorption maxima for the target cell or subcellular component or tissue, or exogenous chromophore. In some cases it may be desirable to target more than one maxima—either simultaneously or sequentially on the same or different treatment dates. The presence of multiple maxima action spectra are common for a given cell or subcellular component or exogenous chromophore and different wavelength maxima irradiation may produce different results.

If the wavelength band is overly broad, then the desired photomodulation effects may be altered from those intended. Consequently, use of broad band noncoherent intense light sources may be less desirable than those specified for use with the present invention, in contrast to the use of multiple narrowband emitters. The laser diodes are also multichromatic with narrow wavelength bands around a dominant band, i.e., they are narrowband multichromatic devices—devices which emit electromagnetic in a narrow band of radiation either symetrically or asyinetrically around a dominant wavelength. For purposes of the present invention, any device that emits electromagnetic radiation in a bandwidth of +/− about 1000 nanometers around a dominant wavelength can be considered to be a narrowband, multichromatic emitter. LEDS, while not monochromatic, emit in such a narrow band as to be considered narrowband multichromatic emitters. The narrow band allows photons of slightly different wavelengths to be emitted. This can potentially be beneficial for creating certain desirable multi photon interactions. In contrast, most commercial lasers emit light at a single wavelength of light and are considered monochromatic. The use of lasers, according to the prior art, has relied upon the coherent, i.e., monochromatic, nature of their electromagnetic emissions.

Wavelength may also determine tissue penetration depth. It is important for the desired wavelength to reach the target cell, tissue or organ. Tissue penetration depth for intact skin may be different than the tissue penetration depth for ulcerated or burned skin and may also be different for skin that has been abraded or enzymatically peeled or that has had at least a portion of the stratum corneum removed by any method . It is also important to penetrate any interfering chromophore that also absorbs at this same wavelength (e.g. dark ethnic skin, plastic Petrie dishes for tissue or cell culture, etc.). It is important to penetrate any tissues or organs in its pathway (e.g. capsule of pancreas; or for reaching some nerve tissue, might need to pass through tendons, fascia, bone.)

Thus, selection of the proper wavelength is one of the significant parameters, but others are important as well:

Energy Density—The energy density corresponds to the amount of energy delivered during irradiation and is also referred to as energy intensity and light intensity. The optimal 'dose' is affected by pulse duration and wavelength—thus, these are interrelated and pulse duration is very important—in general high energy produces inhibition and lower energy produces stimulation.

Pulse duration—The exposure time for the irradiation is very critical and varies with the desired effect and the target cell, subcellular component, exogenous chromophore tissue or organ.(e.g. 0.5 microseconds to 10 min may be effective for human fibroblasts, though greater or lesser may also be used successfully).

Continuous Wave (CW) vs. pulsed—e.g. the optimal pulse duration is affected by these parameters. In general, the energy requirements are different if pulsed mode is used compared to continuous (CW) modes. Generally, the pulsed mode is preferred for certain treatment regimen and the CW mode for others.

Frequency (if pulsed)—e.g. higher frequency tends to be inhibitory while lower frequency tends to be stimulatory, but exceptions may occur.

Duty cycle—This is the device light output repetition cycle whereby the irradiation is repeated at periodic intervals, also referred to herein as the interpulse delay (time between pulses when the treatment session comprises a series of pulses).

As an example, human fibroblasts increase production of desirable components such as collagen when photostimulated. The cells themselves also may multiply. During this increased cellular activity they may utilize increased amounts of 'raw materials' to produce the products of their increased activity. (e.g. Vitamin C is needed in the production of collagen, ionic calcium and magnesium may be vital) as well as such things as growth factors, etc. Thus increased amounts of such substances may be needed to achieve the maximal production of substances such as collagen, elastin and dermal matrix or ground substance (GAG) when fibroblasts are stimulated. Analogous situations with different substrates and cofactors exist for almost every living cell type. It is anticipated that in order to reap the maximal benefits from photoactivation of cells, subcellular components, tissues, organs, cultures, transplants, autografts in either animals or plants, that such "raw materials" or cofactors may be needed as supplemental to the method of the present invention in order to achieve the greatest benefit from the invention. Also, genetically altered cells or subcellular components may have specific different requirements as may cells in certain disease states or tumor growths as well as cells affected by certain types of environmental damage. There are also issues of enzymatic stimulation or inhibition; examples of which may include the matrix metalloproteinases (MMPs) and their inhibitors (TIMPs). In the case of increasing or stimulating fibroblast activity to produce proteins such as collagen, elastin, GAGs and other related substances the inhibition of enzymes which degrade or destroy these proteins after they are produced is very useful in increasing the 'net accumulation' of these substances. Thus agents which block or inhibit these MMPs will be useful as agents in the topical enhancing skin formulations or in the nutraceuticals that are ingested orally. Since the activity of such MMPs is frequently elevated above normal baseline levels in many situations where stimulating fibroblast activity is desirable (for example MMPs are elevated in sundamaged skin and in the skin of smokers) the inhibition of these is even more important to achieve maximal results from fibroblast stimulation. The same applies to photoinhibition where substances which block, retard, interrupt or otherwise interfere with the activity of undesirable cells will be useful.

While not wishing to be bound by a particular theory, it is believed that the invention functions by delivering light energy to a group of metal complexes within what is called the cytochrome system which is within the subcellular components called mitochondria (the 'energy power plants' of the fibroblast and other living cells). For plants the corresponding system is also the cytochrome system, but additionally the phtyochrome system may have a role as well.

When irradiated, these produce a cellular response moderated by flow of electrons in the mitochondria respiratory chain. When the interaction with the quanta of energy delivered by these photons to these electrons occurs, complex interactions may result. These interactions may include an alteration of the "energy charge" of the mitochondria. Oxidative phosphorylation may be stimulated to go faster or to become more efficient—or both. One possible mechanism for this increased efficiency would be a change in the conformational shape of the membrane—which may be related to ionic calcium flux across the membrane and also permeability changes in the membrane. This increased efficiency would result in more ATP production per unit of substrate oxidized—this efficiency increase is analogous to getting "more miles per gallon of oxygen" as far as stimulating cell activity and increased energy production by these cells This 'hyperstimulation' of cellular energy production and activity may be transient and also dependent on the supply and proper ratio and bioavailability of all of the appropriate cofactors for a given cell type as described elsewhere in this application. Thus 'too much' stimulation or 'too long' or 'too fast repetition of stimulation' as well as the incorrect parameters of stimulation may be ineffective or less effective or cease as something else becomes the limiting factor for further stimulation. This may be particularly true when using LED sources, due to the variable wavelength present in their narrowband, multichromatic output. This wavelength variability may be manipulated and controlled to some extent by using different energies and different beam patterns.

The overall health and nutrition of cells may also affect the response to treatment in accordance with the present invention. The topical or oral administration of agents may enhance or optimize some desired effects. Such agents may include, for example, vitamins, free fatty acids, pyruvate and its related compounds, antioxidants, glutatione, trace elements in various forms, and any other cofactors or substrates known in the art that are used in cellular and metabolic or biochemical cycles or pathways in living cells, etc. Other issues affecting cell health include chemicals and pollution, diseases, drugs and treatments for diseases such as x-ray exposure, diet and nutrition, hormonal status, chronologic age, factors like telomere/telomorase status, etc.

It is possible to determine some of these by testing in tissue culture on the appropriate cells. Such substances will vary with the cell target and whether bioactivation or bioinhibition is the desired goal. (e.g. use of a topical agent which inhibits or stimulates hair growth in conjunction with the present invention may be much more effective than using just the invention alone. One such example for hair growth inhibition is a derivative of the chaparral plant).

The specific effects of such selective biostimulation can be seen in FIGS. 31A–F. These illustrate an example of scanning electron microscopic images of fibroblasts in culture 5 min after irradiation with one embodiment of the present invention. In the illustrated case, the range of energies was 75–450 micro watts for photoactivation with all other parameters fixed using yellow 590±5 nm LED light. While cytoskeletal changes are seen without destruction, in an adjacent area which was simultaneously irradiated with a much higher dose of light, actual thermal destruction of the cells occurred. This spectrum of producing both non thermal stimulation and thermal destruction of cells with different energy of irradiation may be seen in a single low power image of these fibroblasts where at one end of the view living altered fibroblasts are visible, while at the other end thermally destroyed and dead cells are visible.

Much of the known art is specifically designed and perfected over decades of research to thermally damage or kill (rather than bioactivate or bioinhibit) these cells. This thermal injury may be created by targeting cellular or tissue water or hemoglobin within the blood cells or skin pigment or a variety of natural indirect targets which are heated and then produce injury to these cells or to the surrounding cells or tissues. The 'wound' that is produced and cellular 'debris' and biochemical 'messengers' that are released by such known techniques is aimed at triggering a 'wound healing' process in which, among other things, new collagen, elastin, glycosaminoglycans (GAG), and other substances are produced and/or released. The production and/or release of such products indirectly causes a process which improves or diminishes the outward appearance of skin wrinkles, skin tone, and the visible signs of aging, scars, stretch marks. It may increase the production of desirable or beneficial substances to improve the health or to treat disease states or to prevent disease or aging changes. This thermal mechanism of action relies upon the death or injury of cells or tissues.

Bioactivation or bioinhibition through photomodulation in accordance with the present invention does not require that any cells be killed or thermally injured. This is a basic distinction between the present invention and the prior art where heating living tissue above the threshold for thermal injury was required to achieve changes in tissues.

A wide range of visible, infrared and ultraviolet wavelengths may is potentially be useful. For example, for human fibroblasts wavelengths in the range of the following including, but not limited to, 450 nm, 532 nm, 595 nm, 620 nm, 670 nm, 760 nm, 820 nm, 890 nm, 1060 nm +/–5–15 nm) are of interest.

FIGS. 13A and B illustrate examples of how a plurality of individual optoelectronic devices may be connected in series and in parallel to form a multichromatic, narrowband emitter of electromagnetic radiation, suitable for use according to illustrative, but not exclusive, embodiments of the present invention. Diodes are known to allow current to flow in only one direction, from positive to negative. The directional current flow is illustrated by arrows in FIG. 13A FIG. 13B is a schematic diagram illustrating an example of combined serial and parallel wiring. An example of series wiring is seen in the connections from left to right across the row. An example of parallel wiring is seen between the top and bottom rows. The dome shaped area represents the transparent housing of the LED. The dome may be constructed from an epoxy material.

FIG. 14 illustrates an example of a method of spacing the optoelectronic devices in what may be referred to as a "close packed" spacing in one dimension. Other patterns which allow more space between the LEDs are also possible. Other elements that may be incorporated into the apparatus of the present invention are things such as reflective coatings, special diffusers (such as holographic diffusers that have high forward pass so do not reduce light transmission much), rotating columns studded with LEDs that turn reciprocate—thus reducing the number of LEDs needed.

FIGS. 15A–C show an array of optoelectronic devices arranged into three panels. The cross hatched areas represent protective covers. The covers may transmit light or may diffuse light. Many different materials may be used for the covers. It is also possible to have no cover and to simply have the bare exposed optoelectronic devices. Panels of various sizes and dimensions may be used. The number of optoelectronic devices arranged on the panels may vary from only a few LEDs to thousands of LEDS. The set of three panels shown in FIG. 15A are hinged to allow adjustment, so that the arrangement resembles a three panel make-up mirror. Each panel in the illustrated device may be about 8×10 inches and may include many hundreds of LEDS or laser diodes. The power supply and controls may be connected to the device through wires, or may be built into the device.

FIG. 16 illustrates an example of a parabolic light for providing illumination such as in a surgical operating room. The light may be small, lightweight and may operate from low voltage or from solar panels. Many other configurations not shown are also possible including implantable devices imbedded in appropriate materials.

FIGS. 17A–C illustrate an example of an individual LED in accordance with the present invention and the angle of divergence of an emitted beam. LEDs tend to emit light through a relatively narrow angle. This tends to make the emitted light more directional than light emitted by a typical incandescent light bulb, from which light is emitted in almost all directions.

FIGS. 18A–18C illustrate three different examples or patterns of light energy density the field of illumination. The irradiation illustrated in FIG. 18B is relatively uniform and homogeneous. The irradiation illustrated in FIG. 18C is relatively uneven and non homogeneous. The energy density patterns may vary, depending on the pattern of LEDs, the packing density of the LEDs, the distance from the LEDs, and the angle of divergence of the LEDs. The delivered energy density and the uniformity or homogeneity of light energy may be significantly altered by these pattern choices.

Figure 19:
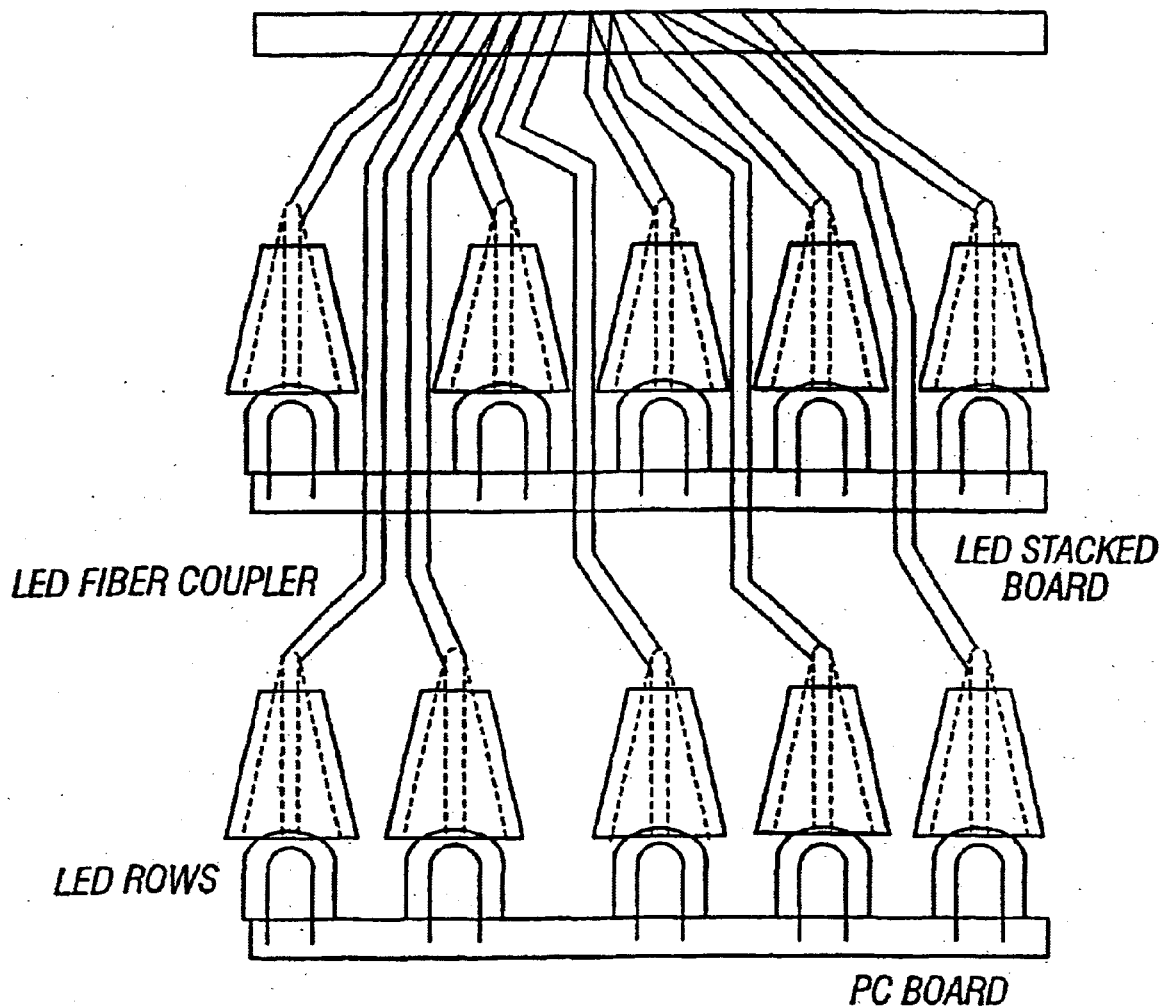
FIG. 19 is a shows a technique for coupling the light output of an optoelectronic device with an optical fiber.

FIG. 19 illustrates an example of a technique for coupling the light output of an optoelectronic device with an optical fiber. In the illustrated example an LED is shown at the bottom with its clear epoxy dome at its top and the wiring at its bottom. A coupler serves as an attaching or mating device that connects the dome portion of the LED to an optical fiber. The optical fiber is suitable for transmitting the particular light wavelength emitted by the LED so that this connection is both secure and also efficient. The efficiency is determined by several factors, including the optimal alignment to mate the optical fiber so that it properly captures the exiting narrow angle of divergence light emitted by the LED. Light energy loss may occur when light crosses surfaces of different optical density. Such energy loss may be minimized by reducing the number of surfaces or interfaces, and by careful selection of the materials themselves so that they match better and in some cases may be additionally coated with anti reflective substances as well.

Figure 20:
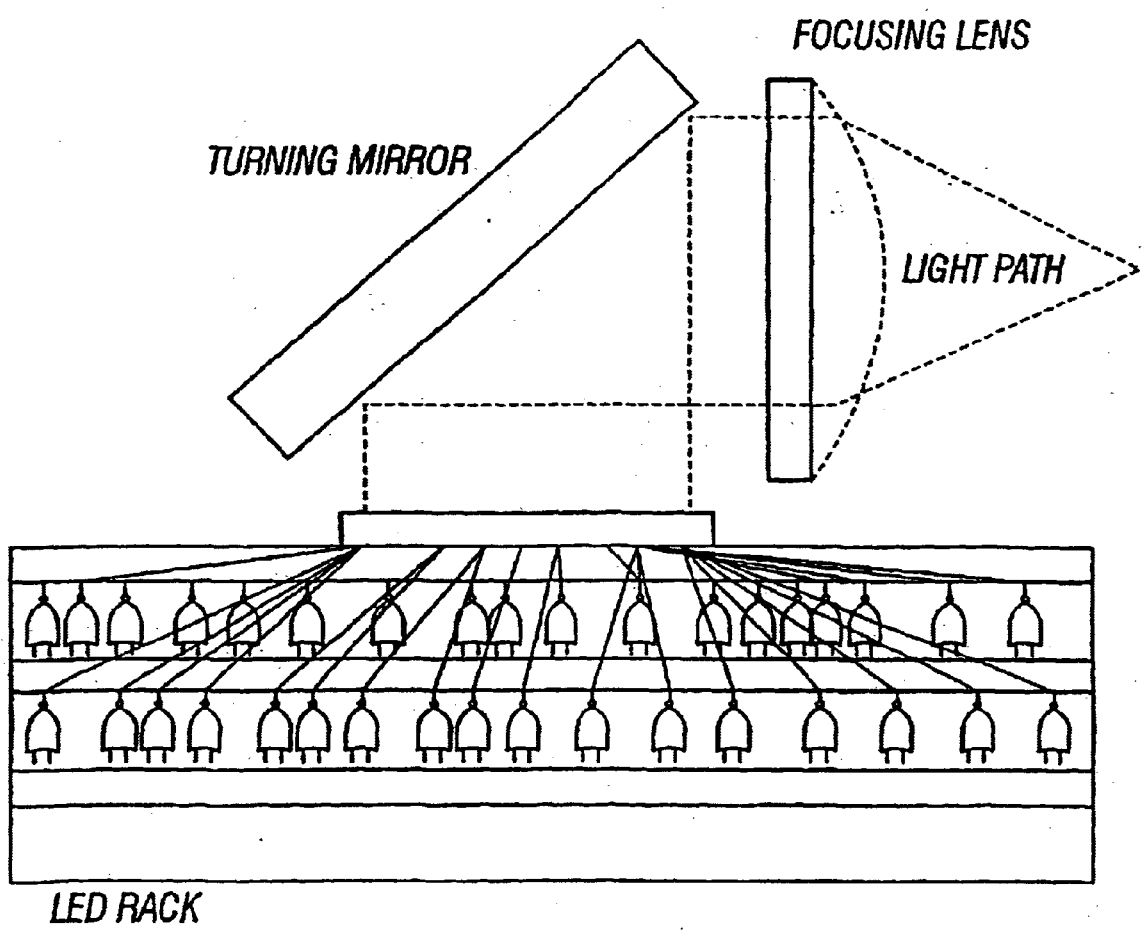
FIG. 20 is a schematic drawing of the output of several individual optoelectronic devices collected into a single beam.

FIG. 20 illustrates an example of how the output of several individual optoelectronic devices may be collected into a single beam. Such an arrangement may be useful when energy output greater than that from a simple flat panel is desired. FIG. 17c illustrates an example of an assemblage of individual LEDs, each of which is coupled to an optical fiber. The optical fibers from the individual LEDs are assembled into fiber bundles. The fibers may then be further combined so that a single, larger fiber or a bundle comprising several fibers transmits the light from all the individual LEDs. The fibers may be coupled to various optical devices or lenses.

Figure 34:
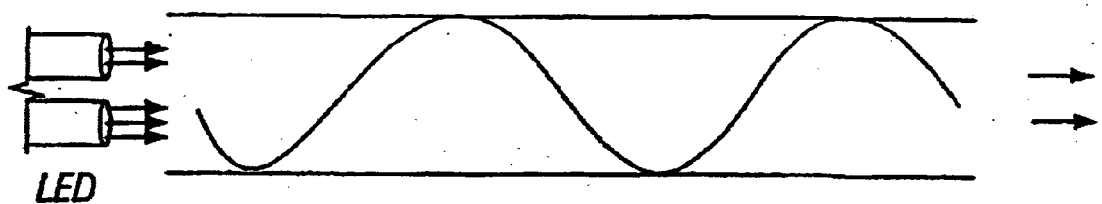
FIG. 34 illustrates an example of an alternative collection mechanism referred to as a "hollow waveguide". This provides an effective mechanism for collecting the output of many individual LEDS without requiring coupling to each LED.

In some instances, the waveguild may be a hollow waveguide as shown in FIG. 34. The hollow waveguide provides an effective mechanism for collecting the output of many individual LEDs without requiring coupling to each LED. The hollow waveguide may be coupled with optical fibers or lens systems, such as those illustrated in FIG. 19 and FIG. 20, or a variety of other devices designed to deliver light.

Figure 21:
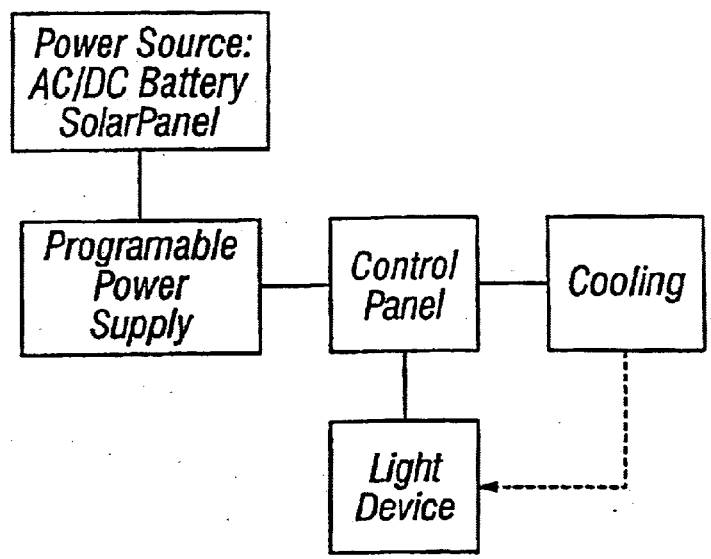
FIG. 21 illustrates a basic schematic of an optoelectronic device in accordance with the present invention.

FIG. 21 illustrates an example of a basic schematic for a simple device. The light source receives power from the power source. The power source is regulated and modulated to provide the desired parameters for various applications of the invention. Power may be from any applicable source as it is converted or regulated to meet the specifications of the LEDs in use. Cooling devices may be used for either the power supply or the light source or both.

Figure 22A:
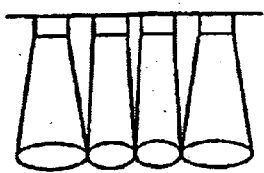
FIGS. 22A–C illustrate alternate illumination patterns achieved by varying the curvature of the substrate supporting the optoeletronic devices and by varying the position and angle of the optoelectronic devices themselves.
Figure 22B:
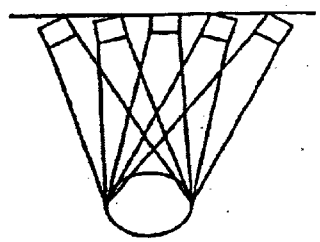
Figure 22C:
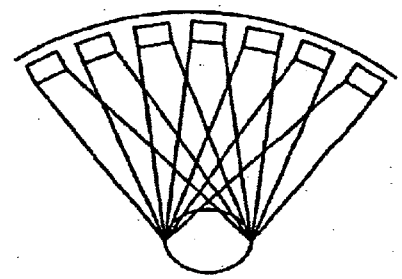

FIGS. 22A–C illustrate examples of three possible configurations to produce three possible illumination patterns. In the illustrated examples the different configurations are achieved by varying the curvature of the substrate supporting the optoeletronic devices and/or by varying the position and angle of the optoelectronic devices themselves. FIG. 22A illustrates an example of a pattern enabling illumination of a broad and generally flat surface area. FIGS. 22B and 22C illustrate examples of more focused patterns on a given surface area. This can also be accomplished through optical fibers or waveguides or lenses as described in earlier figures.

Figure 23A:
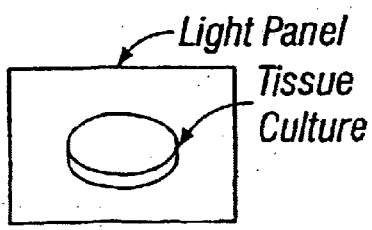
FIG. 23 shows the use of a light panel array in accordance with the present invention for irradiating tissue cultures in the laboratory or in plant materials in cultivation.
Figure 23B:
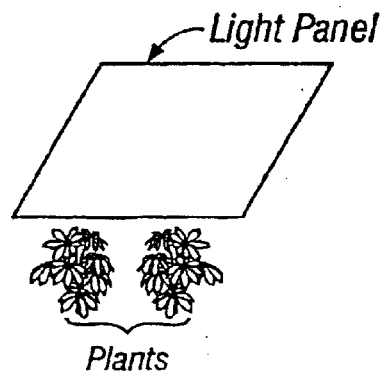

FIG. 23 illustrates an example of using a light panel array in accordance with the present invention for irradiating tissue cultures in the laboratory or in plant materials in cultivation. One application of this might include the in vitro fertilization of a human embryo.

Figure 24:
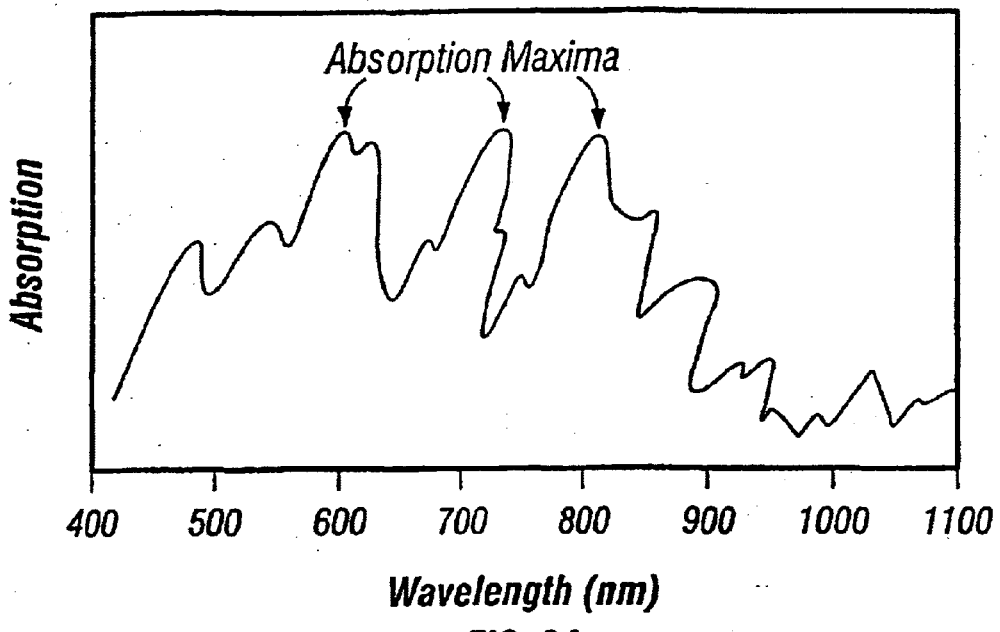
FIG. 24 is a graphical illustration of an representative absorption spectra of human fibroplast cells in monolayer culture.

FIG. 24 illustrates an example of an absorption spectra such as that which might be obtained from a desired target. The illustrated example is similar to the absorption spectrum of human fibroblast cells in culture. Each living organism, cell or subcellular structure has characteristic absorption of various wavelengths of light. Externally applied or exogenous chromophores also have similar properties. When attempting to stimulate, inhibit or modulate such living tissue with light it is desirable to know the absorption properties and characteristics in the wavelength range that includes the light source. One can see the illustration of areas where light is well absorbed (the higher "mountain peaks" areas) or where there is little absorption (the "valleys"). The peaks represent the maximal absorption and indicate that something within the living tissue is absorbing light energy at this wavelength. For example green plants absorb sunlight in their green chlorophyll, but if one extracts and examines chlorophyll it would have a different set of "peaks and valleys" than that of human fibroblast cells.

Figure 25:
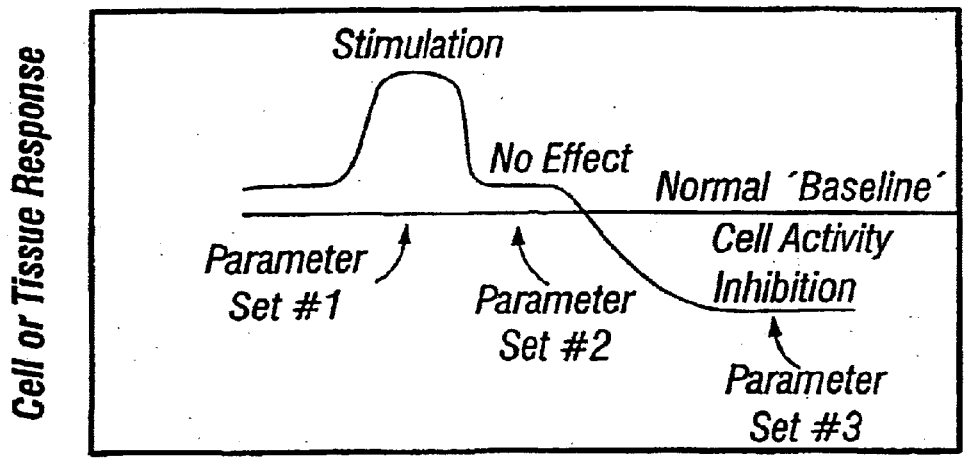
FIG. 25 is a graphical illustration of the difference between photoactivation and photoinhibition and thermal effects on tissue (which may also indirectly produce stimulation or inhibition at a lower level and death and destruction at a higher level).

FIG. 25 is a schematic illustrating an example in which low level energy may produce both biostimulatory and bioinhibitory effects (as well as no effects) when using very similar or identical parameters, but one variable is different. In the illustrated example lower light energy produced stimulation, intermediate energy produced no effect and higher energy levels produced bioinhibitory effects.

It is significant to note that there is an energy level using certain LED configurations higher than the one which produces nonphotomodulation effects which can produce thermal injury. The thermal injury can also have a stimulatory effect though not necessarily the same maginitude or duration or clinical benefit by releasing chemicals which signal that the body has been wounded or injured and thus initiate a well defined sequence of events termed wound healing. The end result of this wound healing mechanism may be the production of new collagen, but this occurs as a result of non-lethal thermal damage to many types of cells. In contrast, the direct bioactivation of a specific cell or subcellular component is triggered by photoactivation without photothermal injury or cell damage. Also, bioactivation tends not to produce uncontrolled wound healing or abnormal wound healing (also termed scarring) as do all thermal events. Finally, there is another even higher level of thermal injury that causes protein denaturation and cell destruction and cell death. Higher levels of thermal injury cause vaporization. In accordance with the present invention, the power of the narrowband multichromatic emitter of electromagnetic radiation is operated to avoid or minimize thermal injury. One way of determining whether thermal injury can occur is by monitoring the intradermal skin temperature of the target tissue during treatment and maintaining a power level to the radiation emitter that does not allow the tissue to exceed the temperature where protein denaturization or vaporization occurs.

Figure 26A:
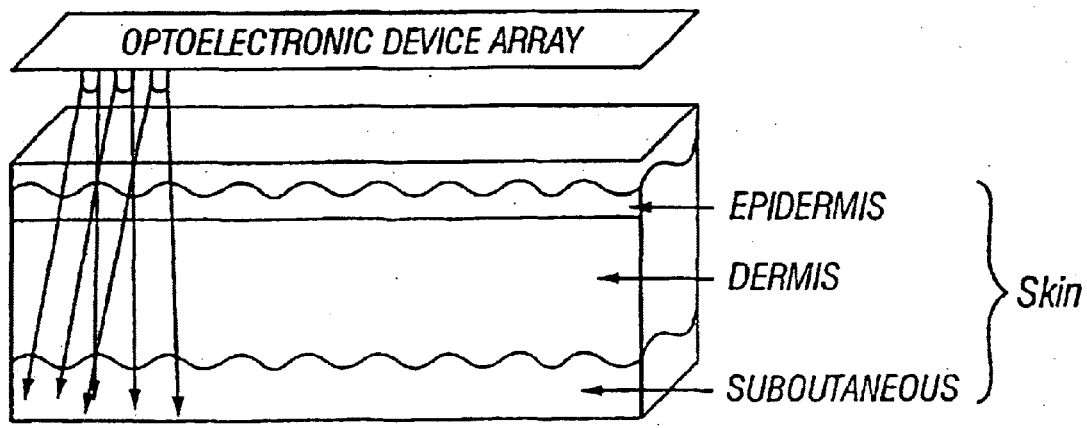
FIG. 26A illustrates an example of an array of devices positioned to illuminate the skin.

FIGS. 27A–F illustrates examples of devices positioned to illuminate the skin for a variety of medical treatments. FIGS. 26B show possible ways that this might be applied for achieving stimulatory effects. A variety of optical events occur as light intersects the skin surface (or any surface). Light energy may be reflected or scattered and thus may not reach its intended target. Various methods exist to reduce such losses. For example, a refractive index matching substance may be applied to the skin surface, or immediately below the surface. Alternatively, a portion of the stratum corneum may be removed from the skin surface. One device useful for removing a portion of the stratum corneum and permitting improved light penetration into the lower layers of the skin is known as a microdermabrader. These devices typically have an array of micron-sized projections (which can be in the form of tiny knives or needles) that can simply remove the topmost epithelial layer or remove the layer of skin and simultaneously deliver a topical composition such as an exogenous chromophore, cosmaceutical, or suitable refractive index matching substance. Another microdermabrasion method involves the use of micron sized abrasive particles of various materials such as various salts, aluminum oxide, diamond particles, etc delivered onto the skin surface by positive or negative pressure, pads, various mechanical devices, etc. Other methods exist for removing stratum corneum such as previously recited.

Numerous veterinary applications are possible including wound healing. An important adjunct to the invention is the use at about the same time and/or as an ongoing separate therapy various topical agents selected to specifically enhance the inhibition or stimulation produced by the LEDs. Such agents might be developed by in vitro testing wherein the target cells for the LED treatment are cultured in vitro and the optimal type and concentration and combination of such active agents alone or in combination with the particular LED light source(s) are determined. The final drawing illustrates an example of one of a wide variety of possible dental and oral surgery applications of this invention: the treatment of periodontal disease wherein damaged or lost gum tissues could be stimulated to become healthier or to regenerate or to be restored by LED therapy or bacterial colonies could be reduced.

FIGS. 27A–F also illustrate examples of possible "inhibitory" effects. FIG. A illustrates an example of use on skin diseases such as psoriasis (a proliferative skin disorder that is known to respond to ultraviolet light therapy). Another application is to delay or inhibit hair growth (alone or in combination with topical active agents which also inhibit or facilitate delaying or reducing hair growth). The treatment of scars or stretch marks is also possible (either to inhibit scar formation preventatively or to reduce scar tissue that has already formed . . . or possibly to stimulate the filling in of depressed scars or stretch marks). One particularly important application is the use of LED light in conjunction with an exogenous chromophore to diminish oil gland activity or to reduce acne. Seen in this figure is an active agent encapsulated in a carrier vehicle of a diameter of about 5 microns (which selectively or non randomly accumulates in oil glands) which is then activated by the LED light (arrows) to biologically inhibit oil gland activity or in another embodiment to injure, damage or destroy the oil gland thus improving acne and other oil gland disorders including oily skin. Another embodiment involves targeting naturally occurring porphyrin compounds (one example of which is protoporphyrin IX) in priopionibacterium acnes wherein the acne bacteria itself is the target chromophore and its destruction or alteration or inactivation reduces acne. Hearing loss and other ear disorders, including but not limited to tinnitus, may be improved by the invention alone or used in combination with locally or systemically administered chromophores or non chromophore substances which enhance the desirable effects of the invention. In this embodiment the LED or other light source could be delivered via fiber optics or waveguides or other methods in the art and could also in one embodiment be a home use device.

FIG. 27E illustrates an example of illumination by the LED of nerve fibers where nerve injuries need to be stimulated, regenerated, or healed. Nail disorders with fungal infection are very common and often unresponsive to topical therapy due to lack of penetration of the agent. The use of LED light to inhibit or destroy the growth of the fungus so that the nail can grow out and the infected portion clipped off is illustrated here (the inhibition of growth is sufficient to eliminate the diseased nail if the growth of the fungus is slowed enough that the nail grows out faster than the fungus grows towards the cuticle and treatment/inhibition continues until the disease portion of the nail is removed). Activation of exogenous chromophores can also be utilized for this treatment (and also disorders such as psoriasis above) and for acne with chlorophyll or copper chlorophyllin or carotenoids or their natural or synthetic derivatives or analogs thereof.

Figure 28:
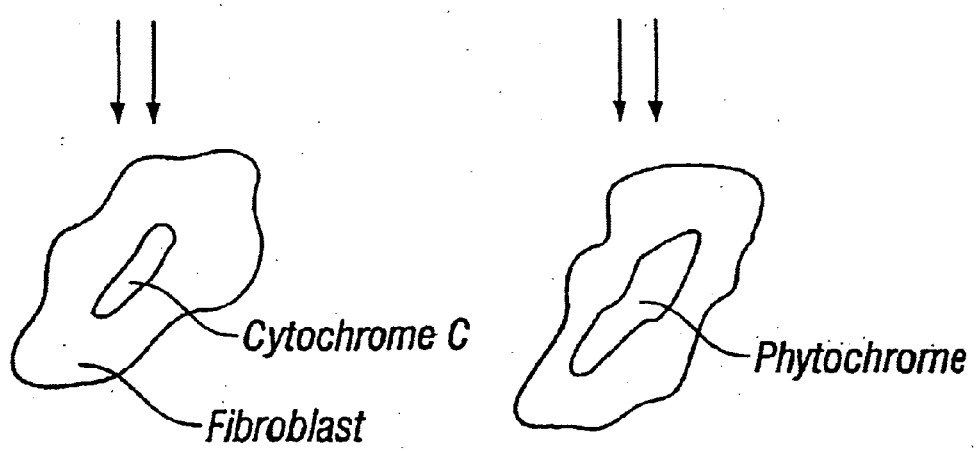
FIG. 28 illustrates an application of the present invention in which subcellular components in animal and plant cells may are targeted.

FIG. 28 illustrates an example in which subcellular components in animal and plant cells may be targeted. Cytochrome and phytochrome are substances which contain certain chemical bonds that absorb selected wavelengths of light. This light energy if of the proper parameters can produce changes that "energize" or "de energize" the mitochondrial activity in the treated cells . . . the mitochondria being the "power plants" of the cells. Thus, in a simplistic manner increasing the power allows the "factory" (cell) to produce more of what it manufactures . . . and reducing the power inhibits production.

In the illustrated fibroblast the "product" is collagen, elastin and ground substance. It is also possible to "signal" a "shift" in the production much as one would make some change on the assembly line in the type of product, but not alter the rate at which the assembly line was producing the product. It is also possible to shift the ratio of the substances which a cell produces—in the case of the fibroblast cell for example more collagen type III could be stimulated and less of collagen type I (this is useful since type III is more desirable for youthful skin than type I since type I is 'stiffer' than type III).

Continuing the analogy, the "factory" needs an ongoing supply of "raw materials" to manufacture its product. Thus, adding topical agents as described previously can be a significant factor in optimizing this process. When the "factory" is stimulated more raw materials are needed. when it is desirable to slow down or inhibit withholding certain raw materials and cofactors (of adding a substance which also inhibits) may be very beneficial. In the illustration one might think of these active agents as applying "fibroblast fertilizers' wherein the production of the 'plants' being "fertilized' are the target cells and their surrounding tissue resources—and just like certain fertilizers are blended or formulated to work better for certain plant types—some with trace elements or other special substances added (for example weed killer may be added to some fertilizers and the analogous additive for fibroblasts is 'MMP killer'—that is an inhibitor of the matrix metalloproteinase enzymes which attack newly formed collagen, elastin, GAGs, etc). The selection of the proper 'fertilizer' composition and its proper application so that it penetrates the soil best are vital for maximizing the growth and productivity of the plants which are being fertilized. Thus it is with the cofactors and enhancing substances used in conjunction with this invention.

Another analogy would be fertilizing plants in a greenhouse and then putting on extra light to stimulate growth (one could also turn up the heat, but that is not necessary and also if it becomes too hot growth will be damaged . . . sort of like pruning plants . . . wound them and they regenerate . . . but if it gets too hot everything dies). This illustrates an example of the critical differences between current and prior art which heats cells such as fibroblasts (as well as surrounding tissues that are not even the target) wherein this invention does not act by a thermal mechanism (though there is a high power embodiment which can also produce controlled thermal effects according to the principles of the theory of selective photothermolysis).

Figure 29A:
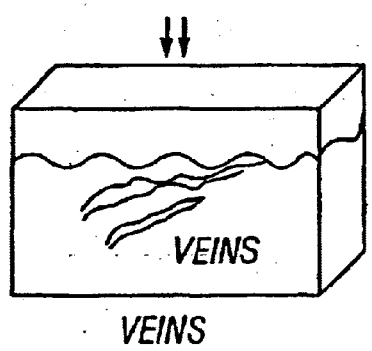
FIG. 29 illustrates a "high power" embodiment of the present invention where the radiation causes destruction (rather than biostimulation or bioinhibition) invloving the treatment of veins (including facial veins, spider leg veins as well as other larger veins), the treatment of unwanted hair growth for the purpose of producing temporary hair reduction or permanent hair removal, and the use of an exogenous chromophore to destroy oil glands in an acne patient.
Figure 29B:
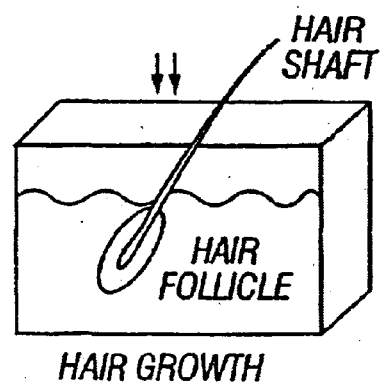
Figure 29C:
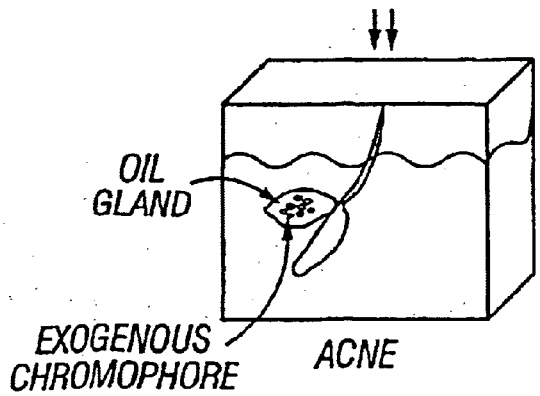

FIG. 29 illustrates an example of a "high power" embodiment where the irradiation results in thermal destruction (rather than photomodulation—bioactivation or bioinhibition). The illustrated example involves the treatment of veins (including facial veins, spider leg veins as well as other larger veins) though may also improve these through bioinhibitory effects. FIG. 29 illustrates an example of the treatment of unwanted hair growth for the purpose of producing temporary hair reduction or permanent hair removal. And also illustrates an example of the use of an exogenous chromophore to destroy oil glands in an acne patient (this is in contrast to the inhibition of oil gland activity demonstrated earlier) by targeting native acne bacteria or exogenous chromophore like chlorophyll or copper chlorophyllin or methylne blue dye or ICG dye, etc.

Figure 30:
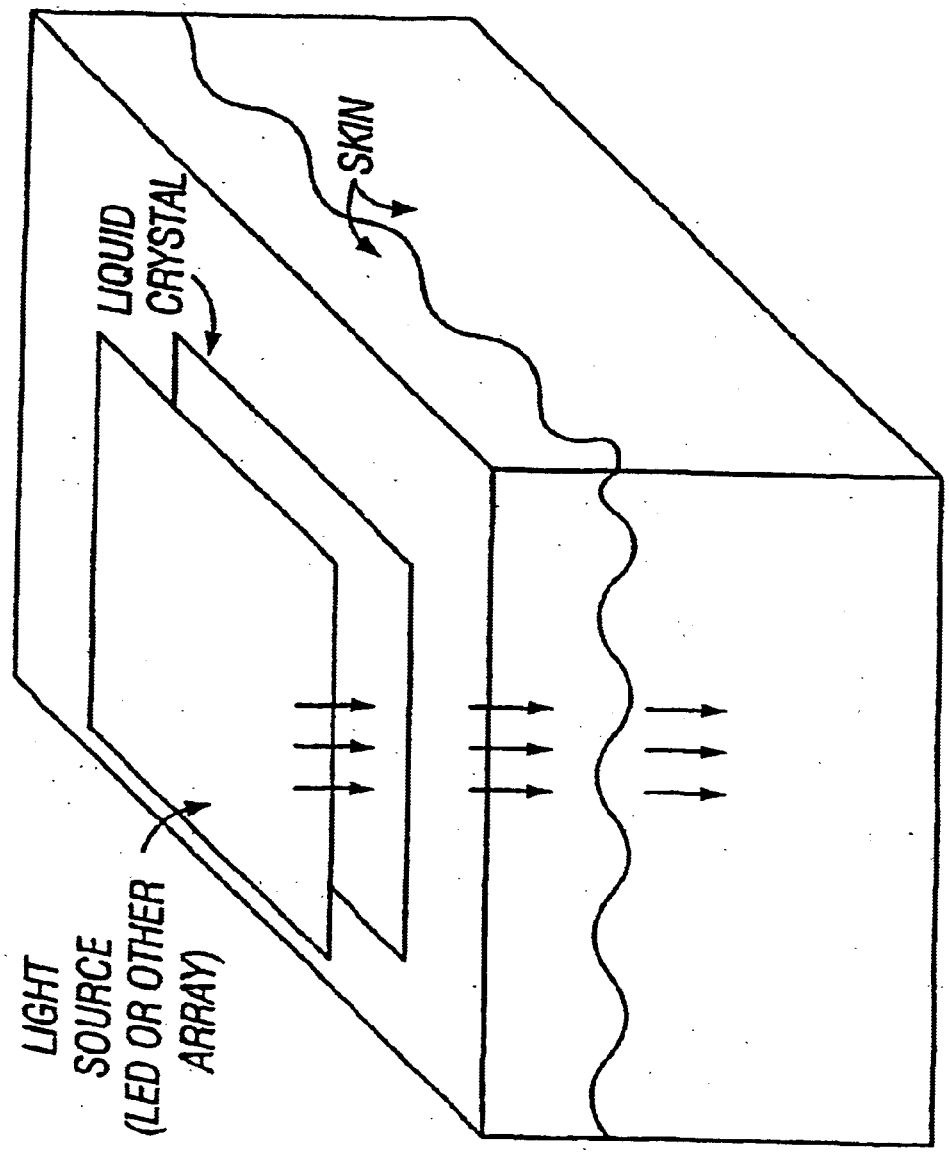
FIG. 30 illustrates use of a liquid crystal interface as a monitoring device for an LED source.
Figure 37:
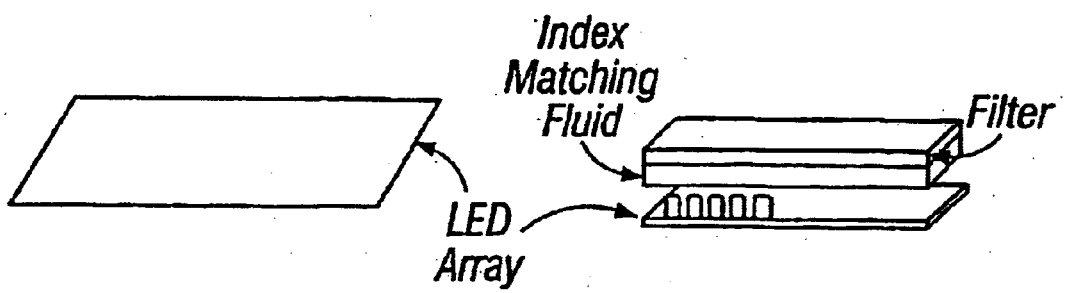
FIG. 37 illustrates an example of one possible design to produce cooling. Cooling may be accomplished by various methods, wherein a cooling apparatus utilizes a sealed chamber and liquid coolant which also function to match the refractive index or to produce diffusion and thus illustrates an example of one way to achieve dual purpose with cooling agents.

FIG. 30 illustrates an example of the use of a liquid crystal interface as a monitoring device. The LED source (but could be any light source including laser or other intense pulsed light source) passes through the LCD which is applied to the surface of the skin. A coupling agent may be applied topically between the LCD and skin to help match the refractive index of the surfaces (and optionally between the LED panel and the LCD). The LCD is connected to a monitoring device (not shown) which measures the percent absorption/reflection and then can be used to adjust the current into the LED (or with other light sources may adjust other appropriate parameters). It is also possible to measure temperature on either side of the LCD which may be useful with different skin tone patients and may also be used in a feedback loop to adjust temperature or cooling devices, such as the one shown in FIG. 37, but also as a safety feature to help prevent undesired thermal injury such as skin damage or blistering.

Figure 31A:
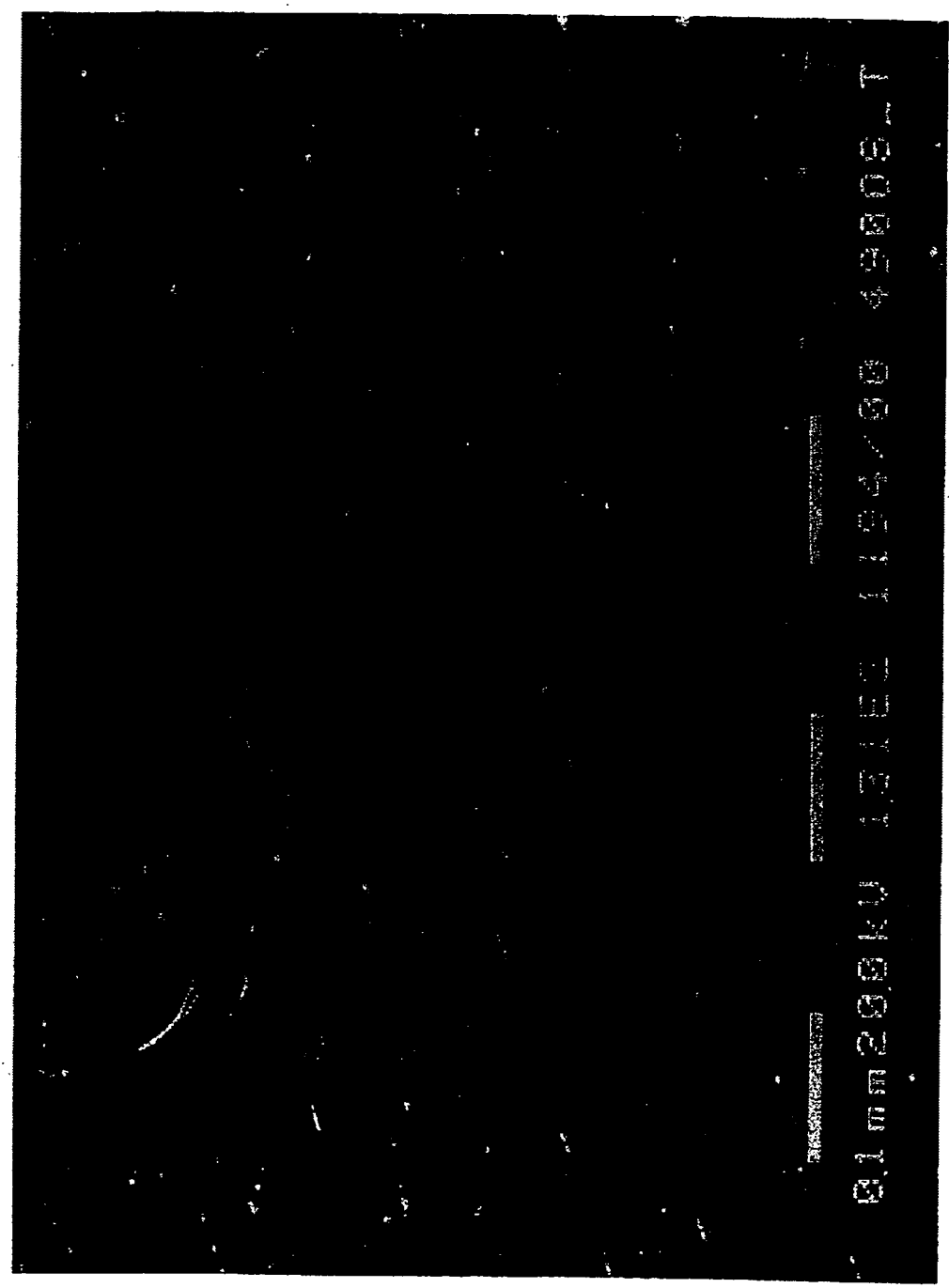
Figure 31B:
Figure 31E:
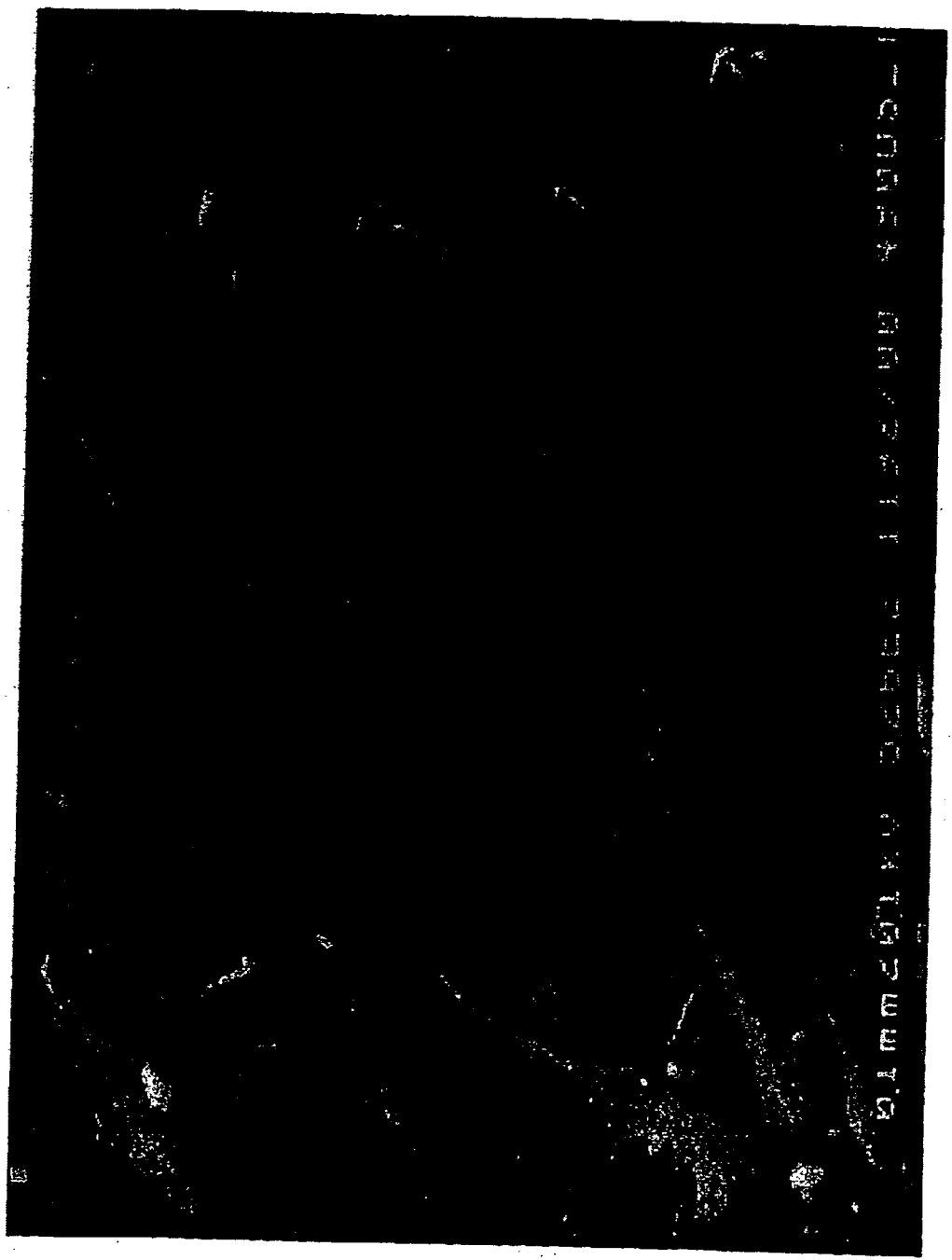
Figure 31F:
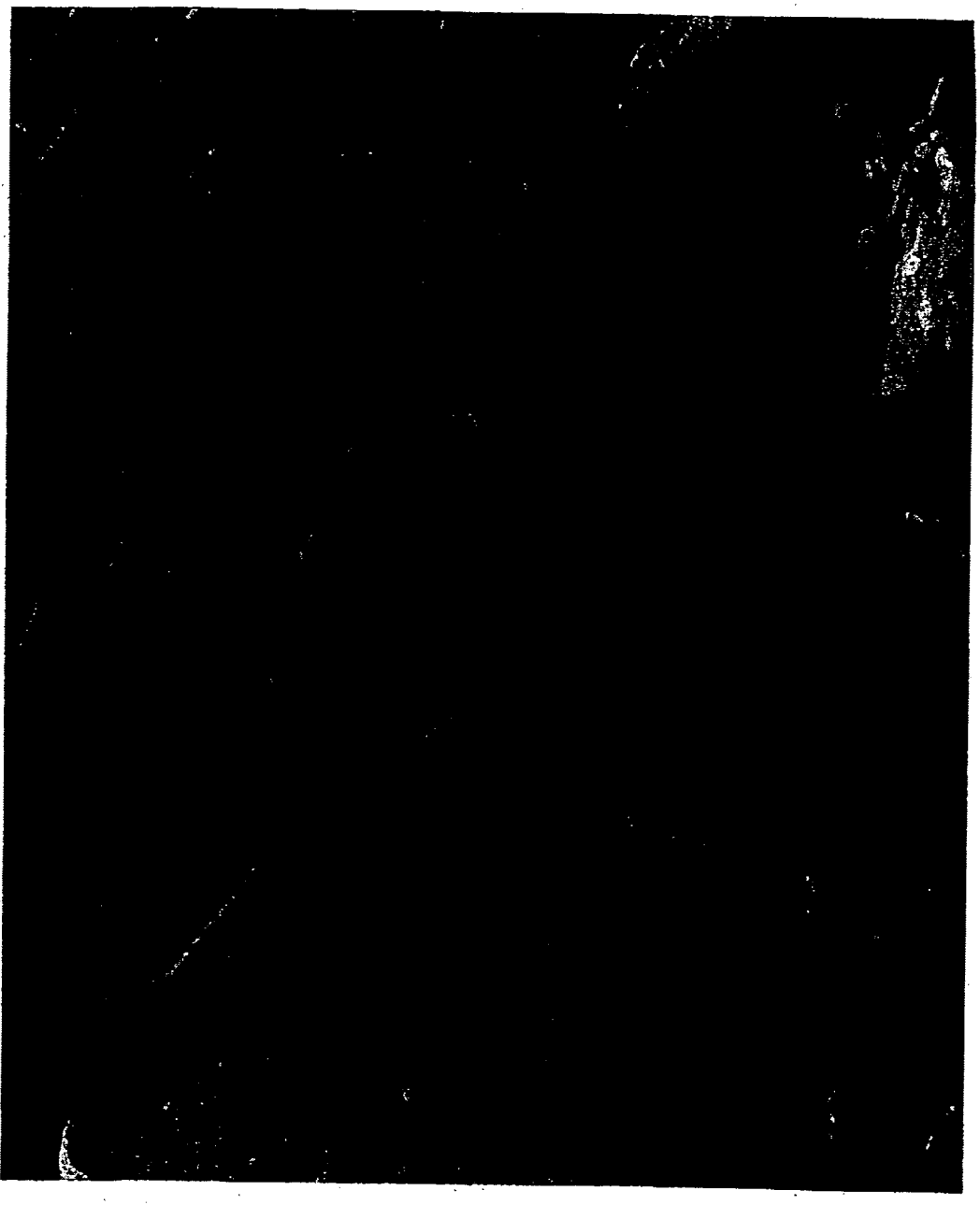

FIGS. 31A–F illustrate examples of electron microscopic photographic images of fibroblasts in culture after irradiation with one embodiment of the present invention using very low levels of light energy produced by a 595 nm yellow LED emitting in the millicandela or microwatt range. FIG. 31A and the left half of FIG. 31B show living but altered cells. The right side of FIG. 31B illustrates an example of dead or dying cells (the latter were exposed to much higher energy levels than the former). These cells are seen again in FIG. 31C with cytoskeletal changes reflecting alteration of the cells but not destruction, FIG. 31D illustrates an example of severely damaged cells. Images "e" and "f" are higher magnification of the altered but living cells in "a" and "c".

The invention will be better illustrated and more fully described by the following examples. Herein, all temperatures are in degrees celsius unless otherwise noted.

EXAMPLE 1

Improvement in Skin Elasticity

Three photo aged females, i.e., females experiencing wrinkles, fine lines, brown pigment splotches, fine capillaries, sagging skin, lost skin elacticity, etc. are tested for improvement in skin elasticity before and after receiving treatment in accordance with the non-ablative method of the present invention. Measurements are taken from their cheeks by utilizing subjective evaluations conducted by trained medical personnel. The LED treatment includes subjecting the target area of the patient's skin to a LED light having a pulse width of 250 msec and a pulse spacing of 250 msec for 90 pulses. Eight treatments over 12 weeks to the entire face with 590 nm multichromatic LED at an intensity ranging from 1.05–2.05 μWatts. Having a bandwidth of +/−5–15 nm, the LED therefore produces light in the wavelength range of from 575 nm to 605 nm. Further, the treatment maintains a skin temperature below the threshold of thermal injury. The average improvement in skin elasticity is shown in Table 1.

TABLE 1

| Skin Elasticity | Pre treatments | Post treatments |
|---|---|---|
| Percent Improvement | 0% | 105% |

EXAMPLE 2

Wrinkle Reduction—Pulsed Treatment

A team of blinded expert graders viewing before and after photos of patients subjected to the non-ablative LILT ("Low Intensity Light Therapy") of the present invention score the global improvement of visible skin wrinkles.

Six photo aged females were tested for reduction of wrinkles. The LED treatment includes subjecting the target area of the patient's skin to a LED light having a pulse width of 250 msec and a pulse spacing of 250 msec for a period of 90 pulses. Eight treatments over 12 weeks to the entire face with 590 nm multichromatic LED at an intensity ranging from 1.0–2.0 μWatts. Having a bandwidth of +/−5–15 nm, the LED therefore produces light in the wavelength range of from 575 nm to 605 nm. Further, the treatment maintains a skin temperature below the threshold of thermal injury. The average reduction in visible wrinkles is shown in Table 2.

TABLE 2

| Week/Value | Averaged Value of Reduction |
|---|---|
| 0 weeks | 0% |
| 4 weeks | 42% |
| 8 weeks | 51% |
| 12 weeks | 48% |

EXAMPLE 3

Wrinkle Reduction—Continuous Wave Treatment

One photo aged female is tested for reduction of wrinkles in accordance with the procedures described in Example 2.

Measurements by expert graders are taken from her cheeks before and after treatment with a single continuous wave pulse for a total of 200 seconds from a 590 mn multichromatic LED at an intensity of 1.05 –2.05 µWatts. Eight treatments spaced evenly over 12 weeks are administered to the patient's entire face.

TABLE 3

| Week/Value | Averaged Value of Reduction |
|---|---|
| 0 weeks | 0% |
| 4 weeks | 22% |
| 8 weeks | 30% |
| 12 weeks | 45% |

EXAMPLE 4

Skin Temperature (Intradermal) Increase Pulsed Dye Laser with Varying Intensity

A coherent 595 nm Pulsed Dye Laser is used on a patient's skin to determine the temperature rise of the skin when subjected to treatment. For measurements, an IT-21 intradermal temperature probe. For this example, a Physiotemp Thermalert model TH-5 monitoring thermometer is inserted mid-dermis via a catheter and then wire taped to secure it to the skin is used to measure the baseline intradermal skin temperate, as well as the intradermal temperature of skin exposed to the laser treatment. The subject has Skin type II and testing is conducted on an untanned left forearm with mid dermis probe placement. The laser is configured for a 10 mm beam width and the skin is exposed to single 0.5 msec pulse at the energy levels, as measured at a calibration port on the radiation emitter, are shown in Table 4. The baseline temperature and intradermal skin temperature after exposure are shown in Table 4, clearly illustrating a rise in intradermal skin temperature after exposure to the laser pulse that varies proportionally to the energy intensity of the laser pulse. (Some absorption by the wire in the probe was attempted to be blanked).

TABLE 4

| Joules/cm$^2$ | Temperature ° C. (baseline) | Temperature ° C. (exposed skin) |
|---|---|---|
| 0.5 | 33.0 | 36.0 |
| 1.0 | 31.0 | 39.0 |
| 2.0 | 32.0 | 43.0 |
| 2.5 | 31.0 | 44.0 |
| 3.0 | 32.0 | 49.0 |
| 4.0 | 32.0 | 51.0 |
| 5.0 | 32.0 | 48.0 |
| 6.0 | 32.0 | 53.0 |

EXAMPLE 5

Skin Temperature (Intrademal) Increase Pulsed Dye Laser with Varying Intensity

A coherent 595 nm Pulsed Dye Laser is used on a patient's skin to determine the temperature rise of the skin when subjected to treatment. For measurements, an IT-21 intradermal temperature probe is used to measure the baseline intradermal skin temperature, as well as the intradermal temperature of skin exposed to the laser treatment. The subject has Skin type II and testing is conducted on an untanned left forearm with mid dermis probe placement. The laser is configured for a 10 mm beam width and the skin is exposed to single 0.5 msec pulse at the energy levels shown in Table 5. The baseline temperature and intradermal skin temperature after exposure are shown in Table 5, clearly illustrating a rise in intradermal skin temperature after exposure to the laser pulse that varies proportionally to the energy intensity of the laser pulse.

TABLE 5

| Joule/cm$^2$ | Temperature ° C. for Base | Temperature ° C. for Test |
|---|---|---|
| 0.5 | 32.0 | 35.0 |
| 1.0 | 31.0 | 37.0 |
| 2.0 | 31.0 | 41.0 |
| 2.5 | 31.0 | 43.0 |
| 3.0 | 31.0 | 47.0 |
| 4.0 | 31.0 | 50.0 |
| 5.0 | 31.0 | 46.0 |
| 6.0 | 31.0 | 52.0 |

EXAMPLE 6

Skin Temperature (Intrademal) Increase Pulsed Dye Laser with Varying Pulse Duration A coherent 595 nm Pulsed Dye Laser is used on a patient's skin to determine the temperature rise of the skin when subjected to treatment. For measurements, an IT-21 intradermal temperature probe is used to measure the baseline intradermal skin temperature as well as the intradermal temperature of skin exposed to the laser treatment. The subject has Skin type II and testing is conducted on an untanned left forearm with mid dermis probe placement. The laser is configured for a 10 mm beam width and the skin is exposed to a single pulse variable duration, as shown in Table 6, at an energy level of 0.5 J/cm$^2$. The baseline temperature and intradermal skin temperature after exposure are shown in Table 6, clearly illustrating a rise in intradermal skin temperature after exposure to the laser pulse that varies proportionally to the energy intensity of the laser pulse.

TABLE 6

| Pulse Duration msec | Temperature ° C. for Base | Temperature ° C. for Test |
|---|---|---|
| 0.5 | 30.0 | 42.0 |
| 2.0 | 30.0 | 44.0 |
| 20.0 | 30.0 | 47.0 |
| 40.0 | 30.0 | 45.0 |

EXAMPLE 7

Absence of Skin Temperature (Intradermal) Increase Led Treatment with Varying Pulse Duration A multichromatic 590 nm+/−15 nm, 5 mm diameter LED produces light at an intensity level of 640 nanowatts/cm2 as measured by a Newport model 1835C multifunction optical meter with a series 818 photodetector. An IT-21 intradermal temperature probe is used to measure the intradermal temperature of the subject who has skin type II. Treatment is applied to the subject's untanned left forearm with mid dermis temperature probe placement. As shown in Table 7, no intradermal temperature rise is perceived by the probe.

TABLE 7

| Pulse Duration msec | Temperature ° C. for Base | Temperature ° C. for Test |
|---|---|---|
| 0.5 | 30.0 | 30.0 |
| 2.0 | 30.0 | 30.0 |
| 20.0 | 30.0 | 30.0 |
| 40.0 | 30.0 | 30.0 |
| 100.0 | 30.0 | 30.0 |

EXAMPLE 8

Pulsed Dye Laser Compared with Light Emitting Diode Skin Temperature Increase

The intradermal temperature for a subject having skin type II is measured on the untanned forearm to compare the skin temperature increase caused by a pulsed dye laser with an LED light source. A coherent 595 nm pulsed dye laser is pulsed for 0.5 msec at varying energy intensities as shown in Table 8. A multichromatic 590 nm LED is pulsed for 0.5 msec with a maximum energy output of 2.0 microWatts/cm2 the comparative intradermal temperature resulting from each light emitter are compared in Table 8.

TABLE 8

(All measurements taken at a radiation intensity of 2 microwatts/cm$^2$)

| J/cm2 | LED (temperature) | Laser (temperature) |
|---|---|---|
| 0.5 | 32.0 | 33.0 |
| 1.0 | 32.0 | 34.0 |
| 1.6 | 32.0 | 34.5 |
| 2.0 | 32.0 | 36.5 |
| 2.5 | 32.0 | 37.5 |
| 3.0 | 32.0 | 36.5 |
| 3.4 | 32.0 | 38.0 |
| 4.0 | 32.0 | 41.0 |
| 4.5 | 32.0 | 42.5 |

EXAMPLE 9

Pulsed Dye Laser Compared with Light Emitting Diode Skin Temperature Increase

The intradermal temperature for a subject having skin type II is measured on the untanned forearm to compare the skin temperature increase caused by a pulsed dye laser with an LED light source. A coherent 595 nm pulsed dye laser is pulsed at an energy intensities of 2.5 J/cm$^2$ for the pulse durations shown in Table 9. A multichromatic 590 nm LED is pulsed at an energy output of 2.0 microWatts for the durations specified in Table 9. The comparative intradermal temperatures resulting from each light emitter are compared in Table 9.

TABLE 9

| Pulse Duration (msec) | LED (temp) | Laser (temp) |
|---|---|---|
| 0.5 | 32.0 | 33.0 |
| 2.0 | 32.0 | 34.0 |
| 20.0 | 32.0 | 34.0 |
| 40.0 | 32.0 | 35.0 |
| 100.0 | 32.0 | |

EXAMPLE 10

Non-ablative Skin Therapy for Wrinkle Reduction

Pulsed Treatment

Human skin is exposed to 180 pulses of a narrowband, multichromatic 590 nm LED at an energy output of 1.05 microwatts to 2.05 microwatts with a pulse duration (the length of each pulse) of 100 milliseconds and an interpulse interval (time between each pulse) of 100 milliseconds. The treatment is repeated 8 times for 12 weeks to the entire faces of a group of 6 photo aged females. The amount of wrinkle reduction as measured by a team of blinded expert graders viewing before and after photos of the treated skin is shown in Table 10.

TABLE 10

| Treament Time (weeks) | Avg. % Reduction (cheeks measured) |
|---|---|
| 0 | 0 |
| 4 | 42 |
| 8 | 53 |
| 12 | 48 |

EXAMPLE 11

Non-ablative Skin Therapy for Wrinkle Reduction

Continuous Wave Treatment

Human skin is exposed to 200 second continuous wave of a narrowband, multichromatic 590 nm LED at an energy output of 1.0 microwatts to 2.0 microwatts. The treatment is repeated 8 times for 12 weeks to the entire face of a single photo aged female. The amount of wrinkle reduction as measured by a team of blinded expert graders viewing before and after photos of the treated skin is shown in Table 11.

TABLE 11

| Treament Time (weeks) | % Reduction (cheeks measured) |
|---|---|
| 0 | 0 |
| 4 | 25 |
| 8 | 33 |
| 12 | 50 |

EXAMPLE 12

Non-ablative Skin Therapy for Wrinkle Reduction

Pulsed Laser Diode

Also suitable for use in accordance with the present invention is a laser diode. Typical pulse durations will be from about 100 milliseconds to about 1 second, for pulsed treatment, and from about 1 second to about 30 minutes for continuous wave treatment. Suitable operating power for the laser diode includes the range of from about 10 milliwatts to about 1 watt with about 200 milliwatts to 800 milliwatts being preferred. Commercially available laser diodes having a wavelength between 400 nm and 1000 nm can be used. For this example, human skin is exposed to 90 pulses from an 810 nm laser diode at an energy output of 2.0 microwatts. An interpulse spacing of 250 milliseconds is used. The treatment is repeated 6 times for 12 weeks to the entire face of a single photo aged female. The amount of wrinkle reduction is shown in Table 12.

TABLE 12

| Treament Time (weeks) | % Reduction (cheeks measured) |
| --- | --- |
| 0 | 0 |
| 4 | 20 |
| 8 | 35 |
| 12 | 30 |

EXAMPLE 13

Crows Feet Reduction—Pulsed Treatment

A team of blinded expert graders viewing before and after photos of patients subjected to the non-ablative LILT ("Low Intensity Light Therapy") of the present invention score the global improvement of visible "crows feet" prominent about the eye region.

Six photo aged females are tested for reduction of crows feet. The laser diode treatment includes subjecting the target area of the patient's skin to a laser diode light having a pulse width of 400 msec using a 10 cm beam diameter and a pulse frequency of 1 hz (1 pulse per second). Three pulses are administered. Three treatments over 12 weeks to the entire face with 810 nm laer diode at an intensity ranging 200 milliwatts/cm2. Thermal injury is produced with blood vessels included among the target chromophores (but no skin wound care is needed). The average reduction in crows feet is shown in Table 13.

TABLE 13

| Week/Value | Averaged Value of Reduction |
| --- | --- |
| 0 weeks | 0% |
| 4 weeks | 15% |
| 8 weeks | 28% |
| 12 weeks | 32% |

EXAMPLE 14

Crows Feet Reduction—Pulsed Treatment

A team of blinded expert graders viewing before and after photos of patients subjected to the non-ablative LILT ("Low Intensity Light Therapy") of the present invention score the global improvement of visible "crows feet" prominent about the eye region.

Six photo aged females are tested for reduction of crows feet. The laser diode treatment includes subjecting the target area of the patient's skin to a laser diode light having a pulse width of 600 msec and a pulse frequency of 1 hz (1 pulse per second). Three pulses are administered. Six treatments over 12 weeks to the entire face with 940 nm laser diode with a 10 cm beam diameter at an intensity ranging 250 milliwatts/cm2. Further, this treatment produces a skin temperature sufficient to produce a non ablative thermal injury. The average reduction in crows feet is shown in Table 13.

TABLE 14

| Week/Value | Averaged Value of Reduction |
| --- | --- |
| 0 weeks | 0% |
| 2 weeks | 17% |
| 7 weeks | 28% |
| 12 weeks | 32% |

EXAMPLE 15

Example 15 is carried out under identical conditions except that a 940 nm diode laser with a power of 10 microw/cm2 exposes the subjects to twenty 250 millisecond pulses with an interpulse interval of 250 milliseconds. Six treatments over 12 weeks are performed with similar results. Mechanism is non thermal photoactivation.

EXAMPLE 16

Example 16 is carried out under identical conditions except that a 810 diode laser with a power of 2000 nanowatts/cm2 and a beam diameter of 10cm exposes the subjects to 60, 100 millisecond pulses with an interpulse interval of 900 milliseconds. Six treatments over 12 weeks are performed with similar results. The mechanism of action is non thermal photoactivation.

EXAMPLE 17

Example 17 is carried out under identical conditions with a 940 nm diode laser with a power of 2mw/cm2 exposes the subjects to a continuous wave for 100 seconds. Four treatments over 12 weeks are performed with similar results. Photoactivation non thermal method.

EXAMPLE 18

Example 18 is carried out under identical conditions with a 595 nm flashlamp pulsed dye laser with a power of 3.0 Joues/cm2 exposes the subjects to 40 millisecond pulses, evenly spaced 4 weeks apart. Four treatments over 16 weeks are performed with similar results. Photothermal non ablative method.

EXAMPLE 19

Example 19 is carried out under identical conditions for the purpose of scar reduction. A 595 nm flashlamp pulsed dye laser with a power of 7.0 Joues/cm2 exposes the subjects to a single 40 millisecond pulse, evenly spaced 4 weeks apart. Five treatments over 20 weeks are performed. Scar visibility is reduced by 57% and scar redness is reduced by 82%. Mechanism is thermal non ablative.

EXAMPLE 20

Example 20 is carried out under identical conditions for the purpose of wrinkle reduction (crow's feet). A 532 Nd:YAG laser with a power of 100 milliwatts/cm2 and a beam diameter of 10 cm exposes the subjects to a single minimally overlapped 30 millisecond pulse, evenly spaced 4 weeks apart. Five treatments over 20 weeks are performed. Wrinkle appearance is reduced by 42%. Method of thermal non ablative technique.

EXAMPLE 21

Example 21 is carried out under the same conditions on 5 photoaged female faces for the purpose of full face photoaging and wrinkle reduction. 590 nm at 250 msec pulses with 250 msec off time and 90 pulses. 8 treatments are performed at 1 week intervals and final assessment is made at 12 weeks. In addition to wrinkle reduction similar to Example 10 several other significant changes are noted including reduction in brown liver spots and freckles, improved skin tone and elasticity, decreased or absent small capillaries, and a consistently observed 'creamy' color to skin which is caused by new collagen formation.

EXAMPLE 22

Example 22 is carried out under identical conditions for the purpose of acne reduction. A 415 nm fluorescent light narrow band multichromatic light source with an energy intensity of 10 milliwatts/cm2 and a large panel design covering the entire face exposes the subjects to continuous wave light for 12 minutes with 4 treatments at 2 week intervals. A topical preparation which includes 1.5% copper chlorophyllin, 2.5% carotenoids and 5% green tea is applied for 5 consecutive nights before each treatment session. Supplemental treatment is provided by a battery-powered, small beam diameter, hand held home use device with a 660 nm LED source which exposes individual acne lesions to 2.0 microwatts/$cm^2$ continuous light for 2 minutes per acne lesion. Active acne is reduced by 64%.

EXAMPLE 23

Example 23 is carried out under identical conditions for the purpose of stimulating hair growth. Subjects have male pattern hair loss and are 20–40 years of age with no scalp diseases. A 644 nm LED device with a power of 2.2 microwatts/cm2 exposes the subjects to 250 msec pulses with 250 msec off time between pulses for total o 50 pulses. 6 treatments over 24 weeks are performed. Increase in appearance of hair growth is 22%.

EXAMPLE 24

Example 24 is carried out on female subjects with visible cellulite involving the outside areas of their thighs. A 940 nm diode laser with a power of 250 milliwatts/cm2 and a 10 cm diameter beam exposes the skin in the affected areas with continuous light for 4 minute exposures. Treatments are performed at 3 week intervals for 18 weeks. The appearance of cellulite is reduced by 32%.

EXAMPLE 25

Example 25 is carried out on acute wounds (non infected bums) for the purpose of stimulating wound healing. A 623 nm LED array exposes a 7 inch by 10 inch rectangular area over the skin to 1.5 microwatts/cm2 for 60 pulses of 250 millisec on time and 250 msec off time. Treatments are performed twice weekly until recovery of intact skin is accomplished. Recovery time is dependent on the depth of the burn.

EXAMPLE 26

An adult male with severe acne scarring was treated with a 590 nm LED at 2.0 microwatts/$cm^2$. Two treatments of 90, 250 millisecond pulses with an interpulse interval of 250 milliseconds were administered one week apart. One week after the final treatment diameter and scar depth was reduced by approximately 70%. A second subject received an identical treatment regimen substituting a 644 nm LED and exhibited a 30% reduction in scar diameter and depth.

EXAMPLE 27

Figure 32:
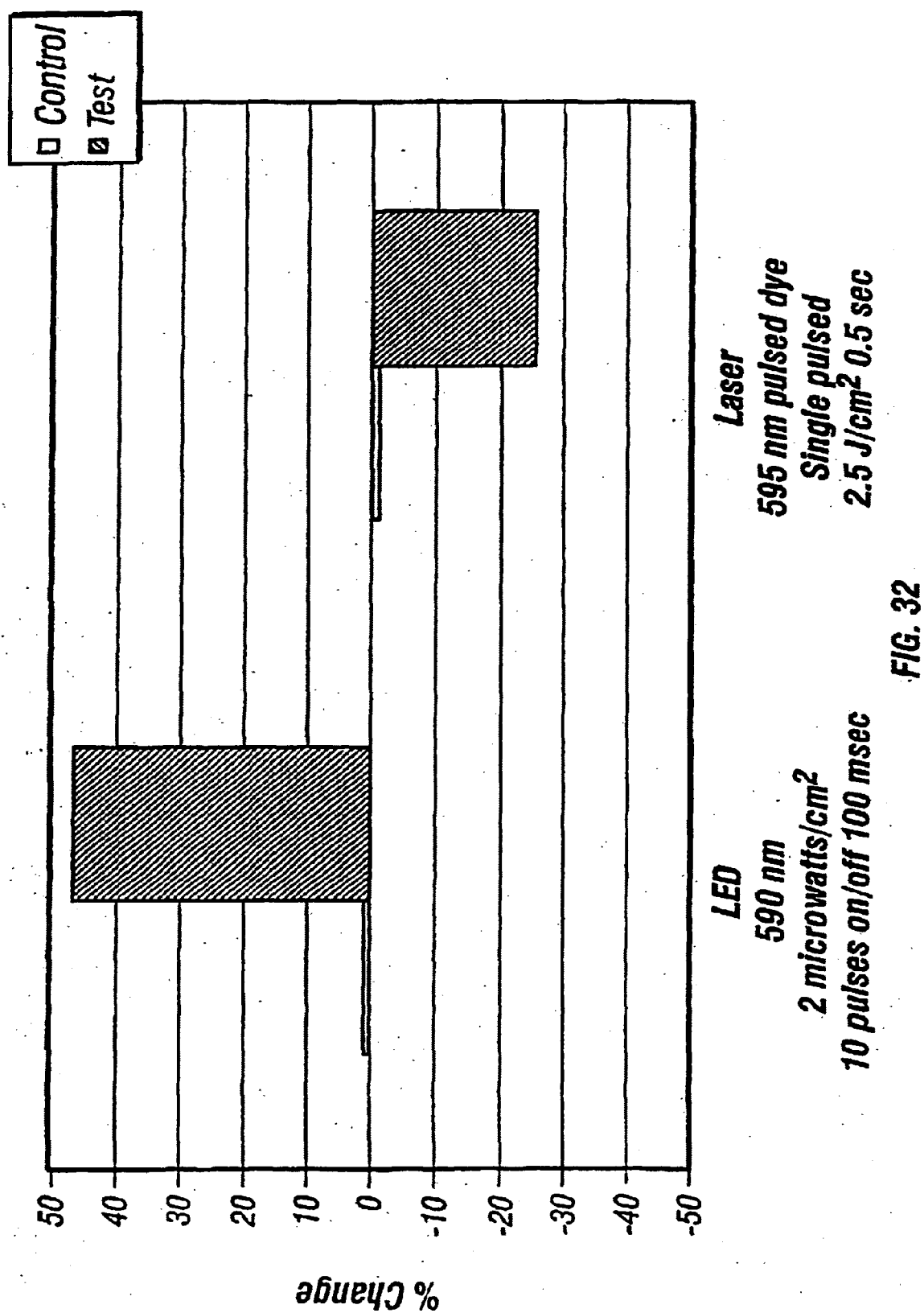
FIG. 32 is a graphical illustration of a percent change of a collagen over control non-thermal photomodulation v. thermal photothermolysis used by narrowband, multichromatic LED emitters and single pulsed laser emitters.

A series of cell tissue cultures containing monolayers of human fibroblast cells were treated in a comparison study to show the difference between treatment efficacy when conducted with a 595 nm pulsed dye laser and a 590 nm LED. The LED was at an energy intensity of 2 microwatts/$cm^2$, pulsed for 100 ms with a 100 ms interpulse interval. The non-thermal photomodulation treatment using the LED used 10 pulses. The 595 nm pulsed dye laser used a single pulse at an energy intensity of 2.5 Joules/$cm^2$ and a pulse length of 0.5 milliseconds for photothermal treatment. Analysis of the collagen I and III production by the fibroblast cells 7 days after treatment had been administered showed no significant change for the controls. The photothermal dye laser treated fibroblast cells exhibited a 25% decrease in collagen I and III production relative to the controls. The fibroblast cells treated with the non-photothermal photomodulation treatment of the present invention exhibited a 46% increase in collagen I and III production relative to the controls. These results are depicted graphically in FIG. 32

What is claimed is:

1. A method for photomodulating living tissue comprising:
   subjecting the living tissue to a narrowband multichromatic source of electromagnetic radiation under conditions effective to stimulate living tissue, wherein the narrowband, multichromatic source emits light within +/−20 nm of a dominant emissive wavelength and a maximum light intensity of no greater than about 4 J/$cm^2$, and wherein the source of narrowband multichromatic electromagnetic radiation is at least one light emitting diode.

2. The method of claim 1 comprising a plurality of light emitting diodes arranged in an array.

3. The method of claim 1 wherein the source of electromagnetic radiation is a plurality of light emitting diodes emitting a dominant emissive wavelength within the range of from about 300 mn to about 1400 nm +/ −5 nm.

4. The method of claim 3 wherein the light emitting diodes emit a wavelength including 590 nm, 644 nm, or 800 nm and have bandwidth of at least +/−5 nm.

5. A method for dermatological treatment comprising:
   exposing human skin to a source of narrowband multichromatic electromagnetic radiation having a maximum light intensity of no greater than about 4 J/$cm^2$;
   photomodulating living tissue within the human skin; and
   maintaining an intradermal skin temperature below the threshold at which thermal injury occurs to the living tissue, wherein the source of narrowband multichromatic electromagnetic radiation is at least one light emitting diode.

6. The method of claim 5 wherein the source of narrowband multichromatic electromagnetic radiation emits a wavelength of from about 300 nm to about 1400 nm.

7. The method of claim 5 wherein the wavelength emitted by the source of narrowband multichromatic electromagnetic radiation is selected from consisting of 300 nm, 415 nm, 585 nm, 590 nm, 595 nm, 600 nm, 630 nm, 644 nm, 810 nm, 940 nm, and 1400 nm.

8. The method of claim 5 wherein the exposure further comprises pulsing the source of narrowband multichromatic electromagnetic radiation for a pulse duration of from about 0.1 ms to about 1×$10^6$ ms.

9. The method of claim 8 wherein the exposure further comprises repeating the pulsing of the source of narrowband multichromatic electromagnetic radiation at an interpulse spacing of from about 1 ms to about 1000 ms for up to 1000 pulses.

10. A method for dermatological treatment comprising:
    applying a topical agent to an area of human skin to enhance the penetration of a wavelength of light chosen for treatment;

exposing the human skin to a source of narrowband multichromatic electromagnetic radiation having a maximum intensity no greater than about 4 J/cm$^2$, wherein the spectrum of electromagnetic radiation emitted by the source of narrowband multichromatic emission includes a wavelength of from about 300 nm to about 1600 nm for a duration of from about 1 millisecond to about 30 minutes;

reexposing the human skin to the source of narrowband multichromatic electromagnetic radiation for a duration of from about 1 millisecond to about 30 minutes up to 1000 times with an interpulse interval of from about 1 millisecond to about 1000 milliseconds; and maintaining an intradermal skin temperature below the threshold at which thermal injury occurs, wherein the source of narrowband multichromatic electromagnetic radiation is at least one light emitting diode.

11. Repeating the treatment method of claim 10 every 1 to 60 days until dermatological treatment is completed.

12. The method of claim 11 wherein the topical agent comprises a topically or orally administered composition have an active agent selected from the group consisting of at least one Vitamin C, Vitamin E, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, an alpha hydroxy acid, a beta hydroxy acid, salicylic acid, antioxidant triad compound, a seaweed derivative, a salt water derivative, an antioxidant, a phytoanthocyanin, a phytonutrient, a botanical product, a herbaceous product, a hormone, an enzyme, a mineral, a genetically engineered substance, a cofactor, a catalyst, an antiaging substance, insulin, trace elements (including ionic calcium, magnesium, etc), minerals, Rogaine, a hair growth stimulating substance, a hair growth inhibiting substance, a dye, a natural or synthetic melanin, a metalloproteinase inhibitor, proline, hydroxyproline, an anesthetic substance, chlorophyll, copper chlorophyllin, carotenoids, and derivatives and analogs of the above items both natural and synthetic.

13. A method for dermatological treatment comprising:

abrading a segment of human skin to be treated to enhance the transmission through the stratum corneum of electromagnetic radiation; exposing the human skin to a source of narrowband multichromatic electromagnetic radiation having a maximum intensity of no greater than about 4 J/cm$^2$, wherein the spectrum of electromagnetic radiation emitted by the source of narrowband multichromatic emission includes a wavelength of from about 300 nm to about 1600 nm for a duration of from about 1 millisecond to about 30 minutes;

reexposing the human skin to the source of narrowband multichromatic electromagnetic radiation for a duration of from about 1 millisecond to about 30 minutes up to 1000 times with an interpulse interval of from about 1 millisecond to about 1000 milliseconds; and maintaining an intradermal skin temperature below the threshold at which thermal injury occurs, wherein the source of narrowband multichromatic electromagnetic radiation is at least one light emitting diode.

14. Repeating the treatment method of claim 13 every 1 to 60 days until dermatological treatment is completed.

* * * * *

UNITED STATES PATENT AND TRADEMARK OFFICE
CERTIFICATE OF CORRECTION

PATENT NO. : 6,663,659 B2  Page 1 of 1
APPLICATION NO. : 09/894899
DATED : December 16, 2003
INVENTOR(S) : David H. McDaniel It is certified that error appears in the above-identified patent and that said Letters Patent is hereby corrected as shown below:

In column 13, lines 19 through 23, replace the sentence:

"For purposes of the present invention, any device that emits electromagnetic radiation in a bandwidth of +/- about 1000 nanometers around a dominant wavelength can be considered to be a narrowband, multichromatic emitter."

with the following sentence:

-- For purposes of the present invention, any device that emits electromagnetic radiation in a bandwidth of +/- about 100 nanometers around a dominant wavelength can be considered to be a narrowband, multichromatic emitter. --

Signed and Sealed this
Fifteenth Day of November, 2011

David J. Kappos
*Director of the United States Patent and Trademark Office*